(12) United States Patent  
Weissgerber

(10) Patent No.: US 7,578,173 B2  
(45) Date of Patent: Aug. 25, 2009

(54) CHROMATOGRAPHY SYSTEM WITH FLOW SENSING

(75) Inventor: Hans-Georg Weissgerber, Straubenhardt (DE)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 11/418,231

(22) Filed: May 4, 2006

(65) Prior Publication Data

US 2007/0000308 A1    Jan. 4, 2007

Related U.S. Application Data

(63) Continuation of application No. PCT/EP03/050794, filed on Nov. 5, 2003.

(51) Int. Cl.  
*G01N 30/38* (2006.01)

(52) U.S. Cl. ..................................... 73/61.56

(58) Field of Classification Search ................ 73/40, 73/61.55, 168, 61.56; 417/62  
See application file for complete search history.

(56) References Cited

U.S. PATENT DOCUMENTS

| | | | |
|---|---|---|---|
| 2,968,589 A * | 1/1961 | Saunders et al. ............. | 162/19 |
| 4,422,151 A * | 12/1983 | Gilson ........................ | 700/283 |
| 4,775,943 A * | 10/1988 | Chamberlin et al. .......... | 702/30 |
| 5,108,264 A * | 4/1992 | Abdel-Rahman ............ | 417/20 |
| 5,807,525 A * | 9/1998 | Allen et al. ................. | 422/131 |
| 6,460,420 B1 * | 10/2002 | Paul et al. ................. | 73/861.52 |
| 2007/0000313 A1 * | 1/2007 | Weissgerber ............... | 73/61.56 |

* cited by examiner

*Primary Examiner*—John Fitzgerald

(57) ABSTRACT

A variety of methods for operating a chromatography system are presented. Specifically, methods for operating a pumping system within a chromatography system are presented. The methods presented are directed to pumping apparatus in which very small amounts of fluid are pumped through the system. A number of techniques for detecting and compensating for leaks are presented as well as a number of techniques for operating the pumping system.

11 Claims, 34 Drawing Sheets

CHROMATOGRAPHY SYSTEM WITH FLOW SENSING

CROSS-REFERENCE APPLICATIONS

This application is a continuation of PCT Application No. PCT/EP2003/050794, filed on Nov. 5, 2003.

BACKGROUND

1. Field of the Invention

Chromatography systems perform a broad range of analysis methods to separate and/or analyze complex mixtures. There are a number of different types of chromatography systems, such as gas chromatography systems, Ion exchange chromatography systems, affinity chromatography systems, liquid chromatography systems, etc. In each type of chromatography system, components of a mixture are separated and distributed between two phases known as a mobile phase and a stationary phase.

2. Discussion of the Background Art

During operation, a mixture of various components is processed through a chromatography system at different rates. The different rates of migration through the chromatography system facilitate the separation of the mixture. Once the separation is accomplished, the different components of the mixture may be analyzed.

One conventional type of chromatography system is a High Pressure Liquid Chromatography system (HPLC). HPLC is a form of liquid chromatography used to separate compounds that are dissolved in a liquid. A conventional HPLC system is shown in FIG. 1. A reservoir 100 stores a liquid. The liquid in the reservoir 100 is considered as the mobile phase. The liquid is drawn (i.e., pumped) out of the reservoir 100 using a pump 102. A variety of pumps may be implemented, such as syringe pumps, reciprocating pumps, etc. A sample is introduced by an injector 104. The mixture of the initial liquid held in the reservoir 100 and the sample is then pushed through a column 106 packed with material. The column 106 is known in the art as the stationary phase. Different components of the mixture move through the column 106 at different rates and as a result, may be analyzed by a detector 108. Final analysis of the mixture is then performed using a computer 110. The mixture ultimately is deposited as waste 112.

A significant component of a chromatography system is the pumping system. A conventional pumping system includes at least one pump. The pump includes a chamber with a reciprocating piston disposed in the chamber. Each pump typically includes an input valve positioned at an input side of the chamber and an output valve positioned at an output side of the chamber. The input valve throttles the flow of liquid into the pump (i.e., chamber) and the outlet valve throttles the flow of liquid out of the pump (i.e., chamber). One substantial feature that distinguishes the pumping systems is whether they are low-pressure gradient pumping systems or high-pressure gradient pumping systems. In a low-pressure gradient pumping system, liquid mixing (i.e., mixing of the mobile phase if more than one solvent is used) occurs before the pump. In a high-pressure gradient pumping system, liquid mixing occurs after the liquid is processed through the pump.

Since a chromatography system separates and quantifies a sample (i.e., mixtures of compounds) based on the rate a liquid is processed through a column, controlling and managing the flow of liquid through the chromatography system is critical to performing the proper analysis of the sample (i.e., mixtures). A central component used to manage the flow of liquid through a chromatography system is the pumping system. In addition, since the liquid (i.e., flow rate, volume) that is processed through a chromatography system is extremely small, an incredible amount of precision and control must be applied to properly manage the flow of liquid through the chromatography system.

However, there are a number of problems that arise when processing liquid through the chromatography system. The problems impact the flow of liquid through the chromatography system and as a result, impact the analysis of the sample (i.e., mixtures of components). For example, varying the flow of liquid through a pump affects the analysis of the sample in a chromatography system; leaks may affect the flow of liquid through a chromatography system; incorrectly calibrated devices, such as sensor(s), may affect the flow of liquid through a chromatography system; cross over of liquids in a pumping system with multiple channels may affect the flow of liquid through a chromatography system; discontinuities in a liquid may affect the flow of liquid through a chromatography system; the intake operation of the pump may affect the flow of liquid through a chromatography system; and the piston timing of a pump may affect the flow of liquid through a chromatography system.

Thus, there is a need for a method and apparatus for managing the flow of liquids in a chromatography system. There is a need for a method and apparatus for managing the flow rate of liquids processed through a pumping system deployed in a chromatography system. There is a need for a method and apparatus for detecting and compensating for leaks within a pump. There is a need for a method and apparatus for attaining and retaining desired flow rates. There is a need for a method and apparatus for calibrating flow sensors. There is a need for a method and apparatus for avoiding channel cross over in multiple channel pumping systems. There is a need for a method and apparatus for optimizing delay volume in a pumping system. There is a need for a method and apparatus for optimizing the intake stroke in a pumping system. Lastly, there is a need for a pumping system with improved piston timing.

SUMMARY OF THE INVENTION

It is an object of the invention to provide an improved chromatography system. A variety of methods and apparatus for operating a pumping system are presented. Among these methods and apparatus are a pumping apparatus with a variable concept for flow generation dependent on a required flow rate; a method for determining and compensating for leaks in piston pumps; a method for calibrating a mass flow sensor; a method for avoiding channel cross flow in multiple channel pumping systems; a pumping method and apparatus with optimized delay volume; a pumping method and apparatus with optimized intake stroke; and a pumping method and apparatus with improved piston timing.

Embodiments of the invention can be partly or entirely embodied or supported by one or more suitable software programs, which can be stored on or otherwise provided by any kind of data carrier, and which might be executed in or by any suitable data processing unit.

One embodiment of a pumping system may comprise: means for configuring the pumping system with at least one sensor means; means for sensing a flow rate of fluid in the pumping system in response to configuring the pumping system with at least one sensor means; and means for determining leaks in the pumping system in response to sensing the flow rate of the fluid.

One embodiment of a pumping system may comprise: means for configuring the pumping system with at least one flow sensor; means for reconfiguring the at least one flow sensor within the pumping system; and means for determining leaks in the pumping system in response to reconfiguring the pumping system with the at least one flow sensor.

One embodiment of a pumping system may comprise: means for characterizing the pumping system to determine leaks in the pumping system; means for metering fluid through the flow sensor; and means for determining a calibration factor in response to characterizing the pumping system to determine leaks and in response to metering fluid through the flow sensor.

One embodiment of a pumping system may comprise: a pumping unit means; a flow sensor means positioned after the pumping unit means; means for characterizing the pumping unit means; means for metering fluid from the pumping unit means through the flow sensor means; and means for determining a calibration factor in response to metering fluid from the pumping unit means through the flow sensor means.

One embodiment of a pumping system may comprise: a channel; an output; means for pumping fluid at a flow rate in the pumping system; means for determining if the flow rate is below a predefined threshold; means for operating at least one first flow sensor at the output of the pumping system if the flow rate is below a predefined threshold; and means for determining if the flow rate is above the predefined threshold; and means for operating at least one second flow sensor within the channel if the flow rate is above the predefined threshold.

One embodiment of a pumping system may comprise: at least one channel, the channel including pumping units and an output; means for pumping fluid at a flow rate in the channel; means for determining if the flow rate is below a predefined threshold; means for operating at least one first flow sensor at the output of the channel if the flow rate is below a predefined threshold; and means for determining if the flow rate is above the predefined threshold; means for operating at least one second sensor within the channel if the flow rate is above the predefined threshold, wherein the at least one second flow sensor is positioned between the pumping units.

One embodiment of a pumping system may comprise: a conveyance; a pressure sensor coupled to the conveyance; a chamber coupled to the conveyance; means for compressing fluid in the chamber; means for monitoring pressure on the conveyance in response to compressing the fluid in the chamber; and means for determining a leak in response to monitoring the pressure on the conveyance.

One embodiment of a pumping system may comprise: a conveyance; a flow sensor coupled to the conveyance and to a valve, the valve further coupled to a chamber including a piston disposed therein, the chamber coupled to the conveyance; means for closing the valve; means for performing an intake stroke with the piston; means for monitoring for flow of fluid with the flow sensor in response to closing the valve and in response to performing an intake stroke with the piston; and means for determining a leak in response to monitoring for the flow of the fluid.

One embodiment of a pumping system may comprise: a pumping unit, the pumping unit comprising a chamber, and a pressure sensor coupled to the chamber; means for pressurizing the chamber; means for testing pressure in the chamber in response to pressurizing the chamber; means for determining a leak in response to testing the pressure in the chamber; and means for compensating for the leak in response to determining the leak.

One embodiment of a pumping system may comprise: an intake tube; a pressure sensor coupled to the intake tube and a chamber coupled to the intake tube; means for filling the chamber with fluid by conveying fluid through the intake tube; means for monitoring pressure on the intake tube in response to conveying fluid on the intake tube; and means for determining if the pressure has dropped below a predefined level in response to monitoring pressure on the intake tube.

One embodiment of a pumping system may comprise: an intake tube; a conveyance; a switching valve coupling the intake tube to the conveyance; a flow sensor coupled to the conveyance and a chamber, the chamber including a piston disposed therein; means for closing the switching valve; means for attempting to convey fluid on the conveyance subsequent to closing the switching valve; means for measuring fluid flow with the flow sensor in response to attempting to convey the fluid on the conveyance; and means for determining a leak in response to measuring the fluid flow with the flow sensor.

One embodiment of a pumping system may comprise: a chamber including an outlet and a piston disposed therein; an outlet valve coupled to the outlet of the chamber; a flow sensor coupled to the outlet valve; means for closing the outlet valve; means for moving the piston upward in the chamber; means for measuring fluid flow with the flow sensor in response to moving the piston upward in the chamber; and means for determining a leak in response to measuring the fluid flow with the flow sensor.

One embodiment of a pumping system may comprise: a conveyance coupled to a pumping unit; means for conveying fluid on the conveyance, the fluid including discontinuities; and means for operating the pumping unit to limit the discontinuities in the fluid.

One embodiment of a pumping system may comprise: means for metering at a flow rate; means for determining a leak in response to metering at the flow rate; and means for compensating for the leak by metering at a new flow rate.

One embodiment of a pumping system may comprise: means for monitoring the pumping system with a flow sensor; means for determining a change in flow rate in response to monitoring the pumping system with the flow sensor; and means for identifying a leak in response to determining a change in the flow rate.

One embodiment of a pumping system may comprise: means for monitoring a flow rate; means for determining a leak rate in response to monitoring the flow rate; and means for compensating for the leak rate in response to determining the leak rate.

One embodiment of a pumping system may comprise: means for monitoring a flow rate; means for determining a leak rate in response to monitoring the flow rate; and means for adjusting the flow rate in response to determining the leak rate.

One embodiment of a pumping system may comprise: a first pumping unit capable of generating a first volume of fluid and a second pumping unit capable of generating a second volume of fluid, wherein the first volume of fluid has a relationship with the second volume of fluid; means for operating the first pumping unit; means for operating the second pumping unit; means for identifying a change in the relationship between the first volume of fluid and the second volume of fluid in response to operating the first pumping unit and in response to operating the second pumping unit; and means for identifying a leak in response to identifying the change in the relationship between the first volume of fluid and the second volume of fluid.

One embodiment of a pumping system may comprise: first and second pumping units coupled together and a flow sensor located between the first and second pumping units; means for metering a flow rate; means for measuring a flow rate; means for comparing the measured flow rate to the metered flow rate; and means for determining a leak in response to comparing the measured flow rate to the metered flow rate.

One embodiment of a pumping system may comprise: a first pumping unit comprising a first chamber, a pressure sensor coupled to the first chamber; a second pumping unit including a second chamber, the second pumping unit in series with the first pumping unit; a valve positioned between the first pumping unit and the second pumping unit; means for delivering solvent with the second pumping unit; means for intaking solvent into the first chamber; means for compressing the solvent in the first chamber; means for opening the outlet valve in response to compressing the solvent in the first chamber while the second pumping unit is delivering solvent; means for delivering a small amount of solvent with the first pumping unit until the second pumping unit must be refilled; and means for measuring system pressure in response to delivering solvent with the first pumping unit and opening the outlet valve.

One embodiment of a pumping system may comprise: a first channel transporting first fluid; a second channel transporting second fluid; a waste output having a valve coupled to the first channel and coupled to the second channel via a conveyance, the waste output adapted for transporting waste, a system output coupled to the first channel via the conveyance and coupled to the second channel, the system output adapted for transporting system fluid; means for opening the valve; means for flushing the second channel in response to opening the valve; means for flushing the first channel in response to flushing the second channel; means for closing the valve in response to flushing the first channel; and means for pumping solvent from the first channel through the conveyance.

One embodiment of a pumping system may comprise: a first channel pumping first fluid; a second channel pumping second fluid; a system output coupled to the first channel and coupled to the second channel, the system output transporting system fluid in response to the first fluid and in response to the second fluid and a flow sensor coupled to the output of the first channel to measure the flow of the first fluid; means for stopping the first channel pumping the first fluid; means for sensing backflow with the flow sensor in response to stopping the first channel pumping the first fluid; and means for determine a leak in response to sensing the backflow.

DETAILED DESCRIPTION OF THE PREFERRED EMBODIMENT

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

Figure 1:
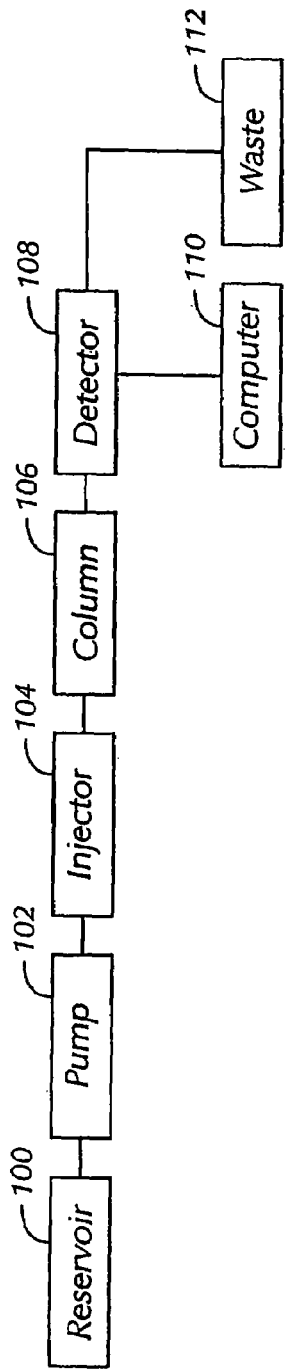
FIG. 1 is a block diagram of a prior art chromatography system.
Figure 2:
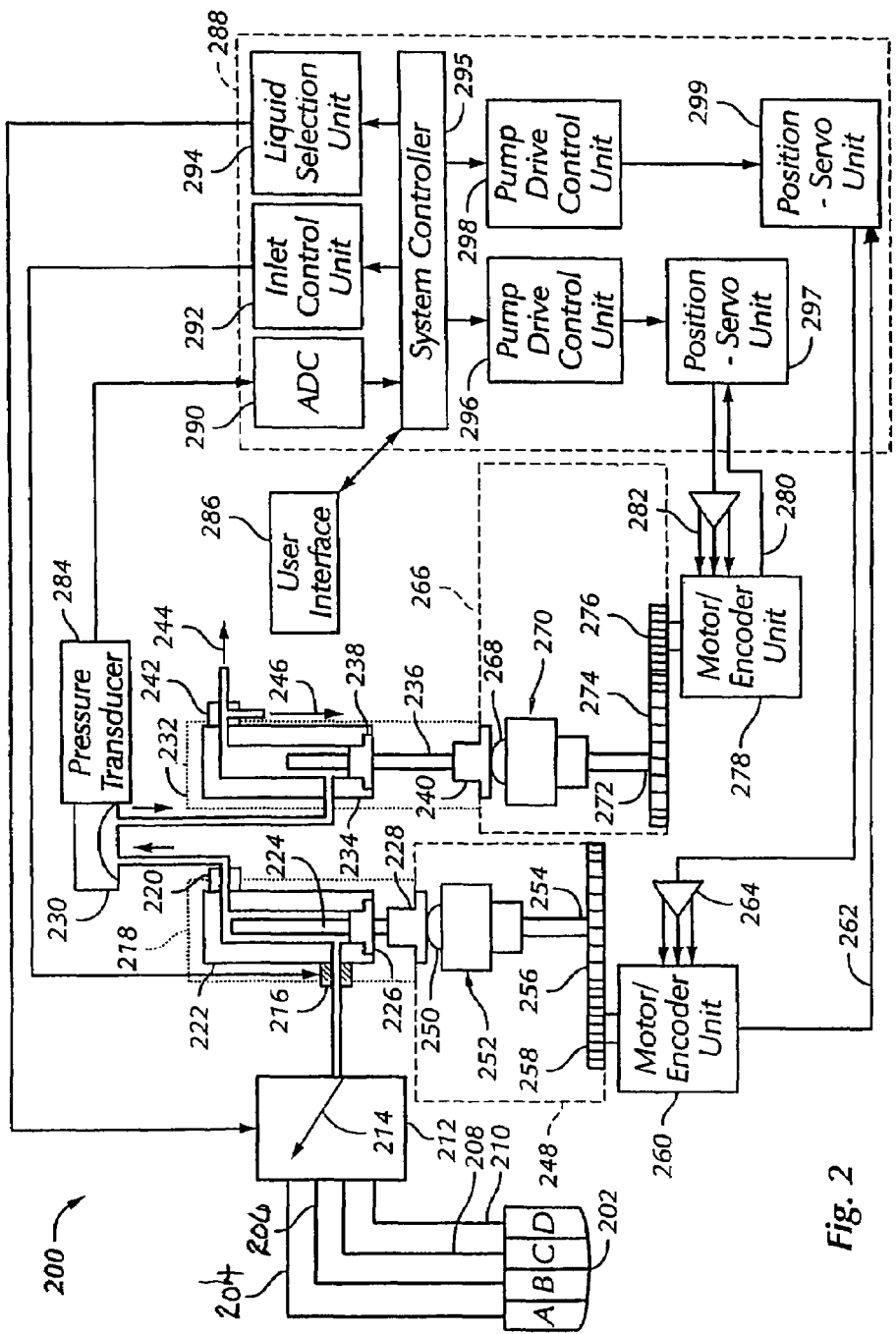
FIG. 2 is a schematic diagram of an embodiment of an isocratic pumping system with additional liquid selection.

FIG. 2 is a schematic diagram of an embodiment of an isocratic pumping system with additional liquid selection at a pump inlet. It should be appreciated that the methods presented in the instant application may be implemented on a pumping system, such as a pumping system 200 displayed in FIG. 2. Pumping system 200 displays two pumping units 218 and 232 positioned in series. Pumping unit 218 includes an inlet valve 216 on an input side of pumping unit 218 and an outlet valve 220 on an output side of the pumping unit 218. Pumping unit 232 includes a purge valve 242 on an output side of pumping unit 232.

A liquid reservoir 202 stores liquids denoted as A, B, C, and D.

Input conveyances 204, 206, 208, and 210 provide pathways and convey liquids A, B, C and D, respectively, from liquid reservoir 202 to a liquid selection valve 212. A selector 214 selects which input conveyance (204, 206, 208, 210) is connected to inlet valve 216. Liquid selection valve 212 is controlled by a liquid selection unit 294. It should be appreciated that in another embodiment of the present invention, a low-pressure gradient pumping system may be implemented by implementing liquid selection valve 212 as a proportioning valve and implementing liquid selection unit 294 as a gradient control unit. Pumping unit 218 includes a chamber 222, a piston 224, a seal 226, and a piston holder 228. Liquid A, B, C, or D is drawn through inlet valve 216 into chamber 222 by a downward motion (i.e., intake stroke) of piston 224. Outlet valve 220 throttles a pathway to a damper unit 230. It should be appreciated that while damper unit 230 and a pressure transducer 284 are shown in pumping system 200, either damper unit 230 and/or pressure transducer 284 may be removed.

Liquid A, B, C, or D flows through damper unit 230 to pumping unit 232. Pumping unit 232 includes a chamber 234, a piston 236, a seal 238, and a piston holder 240. Piston 236 performs an intake stroke and draws liquid A, B, C, or D into chamber 234. On a delivery stroke (i.e., upward movement) of piston 236, liquid A, B, C, or D leaves chamber 234 and is pushed through a valve, such as purge valve 242. Purge valve 242 provides a pathway 244 to a downstream system (not shown in FIG. 2) or a pathway 246 to waste. It should be appreciated that throughout the disclosure, while a specific pumping unit (i.e., 218, 232) may be described and discussed, various modifications of the pumping unit (i.e., 218, 232) may be performed and still remain within the scope of the present invention. In addition, while pumping units with chambers and pistons are implemented, other types of pumping units, such as pumping units with impellers, etc., are anticipated and are within the scope of the present invention. In addition, valves, such as inlet valves 216, outlet valve 220, or purge valve 242, may be implemented as active valves or passive valves.

In one embodiment, a gear system 248 includes a ball 250, an actuator 252, a shaft 254, a gear 256, and a gear 258. Ball 250 is housed in actuator 252 and is in contact with piston holder 228. Shaft 254 causes ball 250 and piston 224 to move upward (i.e., delivery stroke) and downward (i.e., intake stroke), as gear 256 is rotated clockwise and then counterclockwise. In one embodiment, gear 256 is a toothed gear, which is interlocked with gear 258, which is connected to a motor/encoder unit 260. In one embodiment, motor/encoder unit 260 includes a combined motor and encoder coupled to the motor. A position-servo unit 299 communicates information to motor/encoder unit 260 through a position-servo interface 264 and receives feedback via feedback line 262.

A gear system 266 includes a ball 268 positioned within an actuator 270. Ball 268 makes contact with piston holder 240. A shaft 272 causes ball 268 and piston 236 to reciprocate in an upward and downward motion as a gear 274 is rotated clockwise and then counterclockwise. Gear 274 is interlocked with a gear 276, which is connected to a motor/encoder unit 278. A position-servo unit 297 communicates information to motor/encoder unit 278 through a position-servo interface 282 and receives feedback via a feedback line 280.

In one embodiment, a pump control chip 288 is implemented to control pumping system 200. A pump drive control unit 298 controls position-servo unit 299. Position-servo unit 299 controls motor/encoder unit 260 through position-servo interface 264 and receives feedback through feedback line 262. A pump drive control unit 296 controls position-servo unit 297. Position-servo unit 297 controls motor/encoder unit 278 through position-servo interface 282 and receives feedback on the position and movement of motor/encoder unit 278 through feedback line 280.

Pump drive control unit 296 and pump drive control unit 298 interface with an analog-to-digital converter (ADC) 290, an inlet control unit 292, and liquid selection unit 294 through a system controller 295. In addition, users may use a user interface 286 to interface with pumping system 200 through system controller 295.

ADC 290 interfaces with and receives a signal from pressure transducer 284. Inlet control unit 292 interfaces with and controls inlet valve 216, and liquid selection unit 294 interfaces with and controls liquid selection valve 212. A more thorough explanation of the operation of a pumping system such as pumping system 200 may be found in European Patent EP0309596, entitled "Pumping apparatus for delivering liquid at high pressure," published Apr. 5, 1989, which is herein incorporated by reference.

During operation, one of the liquid containers for liquids A, B, C, or D, shown collectively as liquid reservoir 202, is connected to inlet valve 216 so that liquid A, B, C, or D can be delivered. This can be accomplished by either holding selector 214 in a fixed position so that liquid selection valve 212 is connected to one of the liquid containers for liquids A, B, C, or D in liquid reservoir 202. Alternatively, liquid selection valve 212 may be operated as a proportioning valve by moving selector 214 across each input conveyance 204, 206, 208, and 210 so that one of the liquid containers for liquids A, B, C, or D proportions the amount of liquid A, B, C, or D drawn in from liquid reservoir 202.

During a start-up period, piston 224 is moved to a predefined distance referred to as the upper dead center (UDC). Under the control of pump control chip 288, piston 224 moves upward into chamber 222 until piston holder 228 abuts the lower end of chamber 222. Once this end position has been reached, piston 224 moves back downward a predefined distance. In addition, a corresponding angular setting of motor/encoder unit 260 is registered and stored to recreate the movement of piston 224 to the UDC position. In one embodiment, moving a piston, such as piston 224, to a predefined position based on the corresponding angular setting of motor/encoder unit 260 is referred to as metering. In another embodiment of the present invention, any change of piston position or rate of motion, which results in a change in a flow rate of liquid entering and exiting a chamber, such as chamber 222, is considered metering. Metering may be performed by operating piston 224 in combination with motor/encoder unit 260 and pump control chip 288. A similar procedure may be performed to record a piston position where piston 224 moves to a lowest point in the chamber 222 required to draw liquid A, B, C, or D into chamber 222. The lowest point is known as the lower dead center (LDC).

After identifying and setting the UDC position and the LDC position in both pumping units 218 and 232, pumping system 200 begins nominal operation. Inlet valve 216 is opened under the control of inlet control unit 292, and piston 224 moves down from the UDC position to the LDC position. As piston 224 moves from the UDC position to the LDC position, liquid A, B, C, or D is drawn into chamber 222.

In one embodiment, user operates position-servo interface 282 to specify a flow rate for pumping system 200. A corresponding stroke length, which is defined as the distance piston 224 travels between the UDC position and the LDC position, is then implemented in both pumping units 218 and 232 to accomplish the flow rate. Based on the flow rate input by the user, pump control chip 288 computes a corresponding stroke length using a predetermined mathematical relationship between flow rate and stroke length (or stroke volume, which is proportional to the stroke length). In an alternate embodiment of the present invention, pump control chip 288 may be modified to permit a variable or changing selection of the stroke length or volume.

Once piston 224 has traveled the stroke length determined by pump control chip 288 from the UDC position to the LDC position, motor/encoder unit 260 stops movement to stop the flow of liquid into chamber 222 and inlet valve 216 is closed. Motor/encoder unit 260 is restarted, moving in the opposite direction as before until it again reaches the UDC position. Once this is completed, the sequence repeats with piston 224 reciprocating in chamber 222 (i.e., moving down from the UDC position to the LDC position and back again). Piston 236 performs a similar sequence of motions and delivers liquid A, B, C, or D to other parts of the chromatography system (i.e., column) via pathway 244. In one embodiment of the present invention, the movement of piston 224 and piston 236 is synchronized in such a way that the flow through the system is constant over time.

Figure 3:
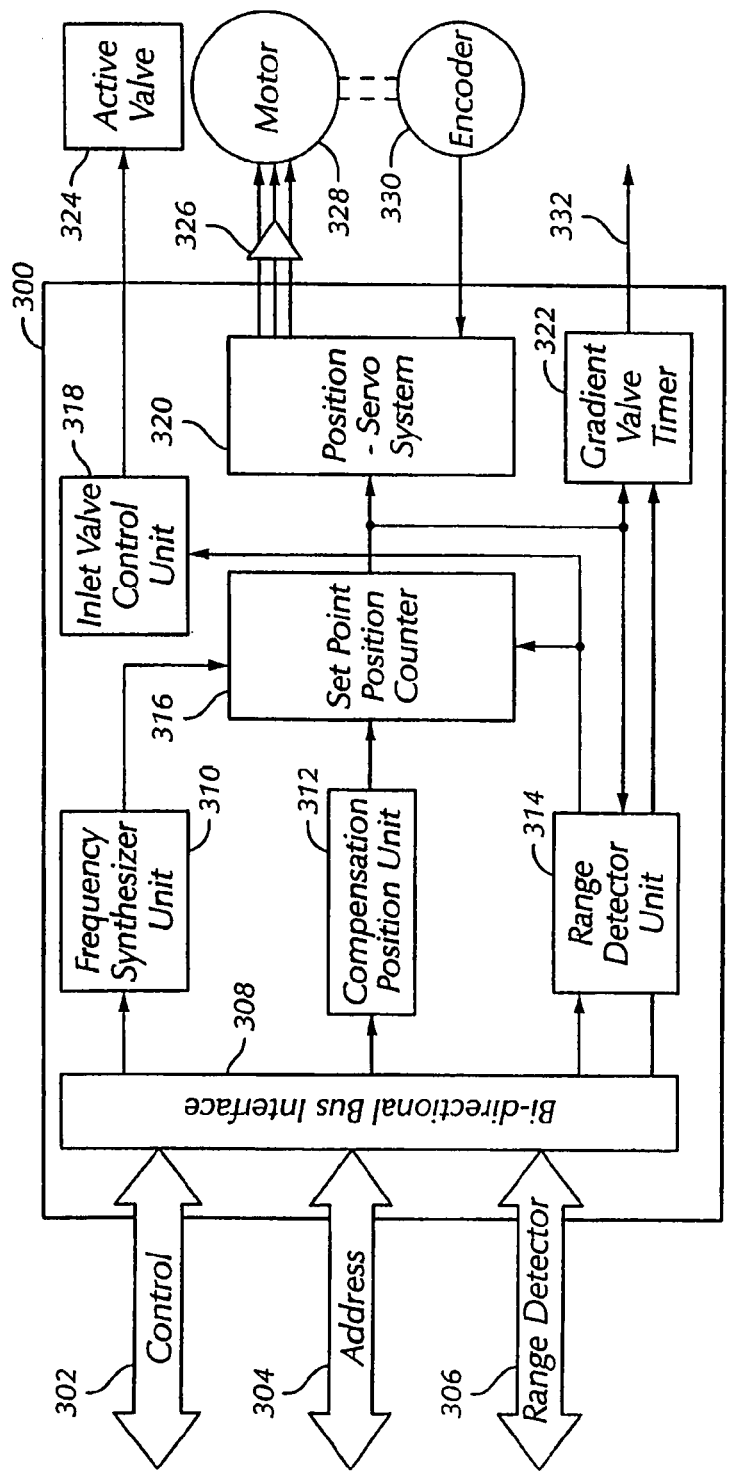
FIG. 3 is a block diagram of an embodiment of a pump control chip.

FIG. 3 is a block diagram of a pump control chip. In one embodiment, pump control chip 300 represents an implementation of pump control chip 288, shown in FIG. 2. In another embodiment, pump control chip 300 is implemented in a pumping system. In another embodiment, pump control chip 300 may be implemented in a computer that interfaces with a pumping system. Input signaling, such as control signals 302, address signals 304, and range detector signals 306, are received by a bi-directional bus interface 308. Bi-directional bus interface 308 provides an interface between the input signaling (i.e., 302, 304, and 306) and a frequency synthesizer unit 310, a compensation position unit 312, and a range detector unit 314. Frequency synthesizer unit 310 provides frequency and counting direction information based on the movement of a piston. Compensation position unit 312 calculates an amount of piston movement necessary in a pre-compression phase of piston operation. Range detector unit 314 defines the upper dead center (UDC) and lower dead center (LDC) of a piston and is responsible for defining the total stroke length of the piston. A set point position counter 316 maintains the position of the piston. For example, if a piston reaches the UDC or LDC, a signal is sent to set point position counter 316, the number of steps for pre-compression are transferred to set point position counter 316 as soon as the piston begins to move upwards, etc.

Range detector unit 314 provides an input to an inlet valve control unit 318, which controls an active valve 324. Range detector unit 314 and set point position counter 316 provide input to a position-servo system 320, which interfaces with a motor 328 through a position-servo interface 326. Motor 328 is coupled to an encoder 330, which provides feedback to position-servo system 320. Lastly, set point position counter 316, range detector unit 314, and bi-directional bus interface 308 provide input to a gradient valve timer 322, which provides an output 332 to a gradient valve (not shown in FIG. 3). It should be appreciated that while a specific embodiment of pump control chip 300 is presented in FIG. 3 and discussed herein, a variety of embodiments may be implemented and still remain within the scope of the present invention.

Figure 4:
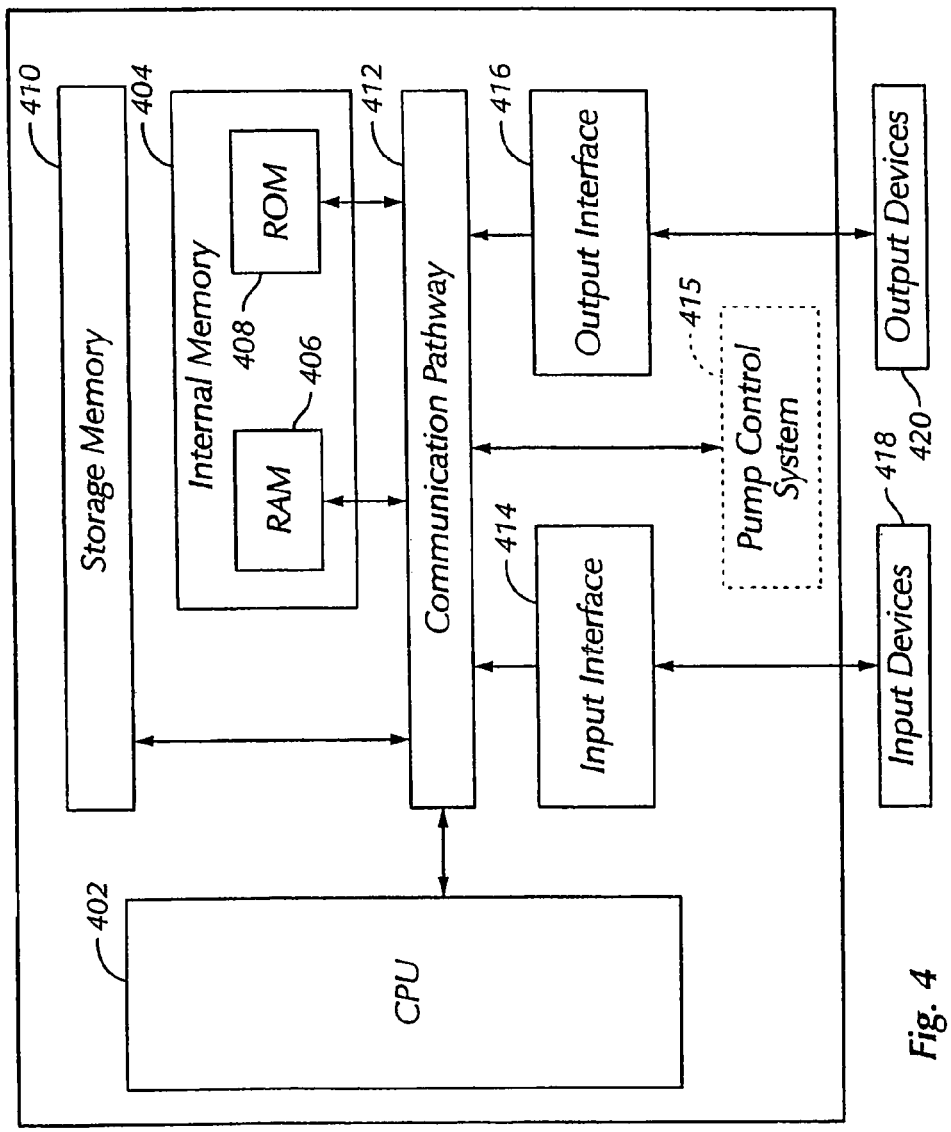
FIG. 4 is a block diagram of an embodiment of a computer.

FIG. 4 is a block diagram of a computer 400 implemented in accordance with the teachings of the present invention. A central processing unit (CPU) 402 functions as a brain of computer 400. An internal memory 404 includes a short-term memory and a long-term memory. The short-term memory may be implemented as a Random Access Memory (RAM) 406 or a memory cache used for staging information. The long-term memory may be implemented as a Read Only Memory (ROM) 408 or an alternative form of memory used for storing information. In one embodiment of the present invention, a short-term memory, such as RAM 406, may be a display memory and used for storing a GUI for display on a monitor.

Computer 400 includes a storage memory 410, such as a hard drive. Computer 400 also includes a pump control system 415, such as pump control chip 288 of FIG. 2 or pump control chip 300 of FIG. 3. In another embodiment, pump control system 415 may be implemented using the other components of computer 400, such as CPU 402, storage memory 410, internal memory 404, a communication pathway 412, an input interface 414, an output interface 416, etc. For example, the logic implementing the functionality of pump control system 415 may be implemented in RAM 406 or in ROM 408. In yet another embodiment, input devices 418 and output devices 420 may be combined in a pump control system, such as pump control system 415. In this configuration, pump control system 415 may be implemented in a pump system and controlled by computer 400. Communication pathway 412 is used to communicate information between RAM 406, ROM 408, storage memory 410, input interface 414, output interface 416, CPU 402, and pump control system 415.

Input devices 418 may include devices such as a joystick, a keyboard, a microphone, a communication connection, servo motor inputs, inlet control inputs, outlet control inputs, gradient control inputs, ADC inputs, a mouse, etc. Input devices 418 interface with the system through input interface 414. Output devices 420 may include devices such as a monitor, speakers, communication connections, servo motor outputs, inlet control outputs, outlet control outputs, gradient control outputs, ADC outputs, etc. Output devices 420 communicate with computer 400 through output interface 416.

In one embodiment of the present invention, routines used to operate a pumping system, such as pumping system 200 of FIG. 2, may be stored in internal memory 404, storage memory 410, or in pump control system 415. CPU 402 may operate under the control of these routines and control pumping system 200 of FIG. 2 by communicating with input devices 418 and output devices 420.

Figure 5:
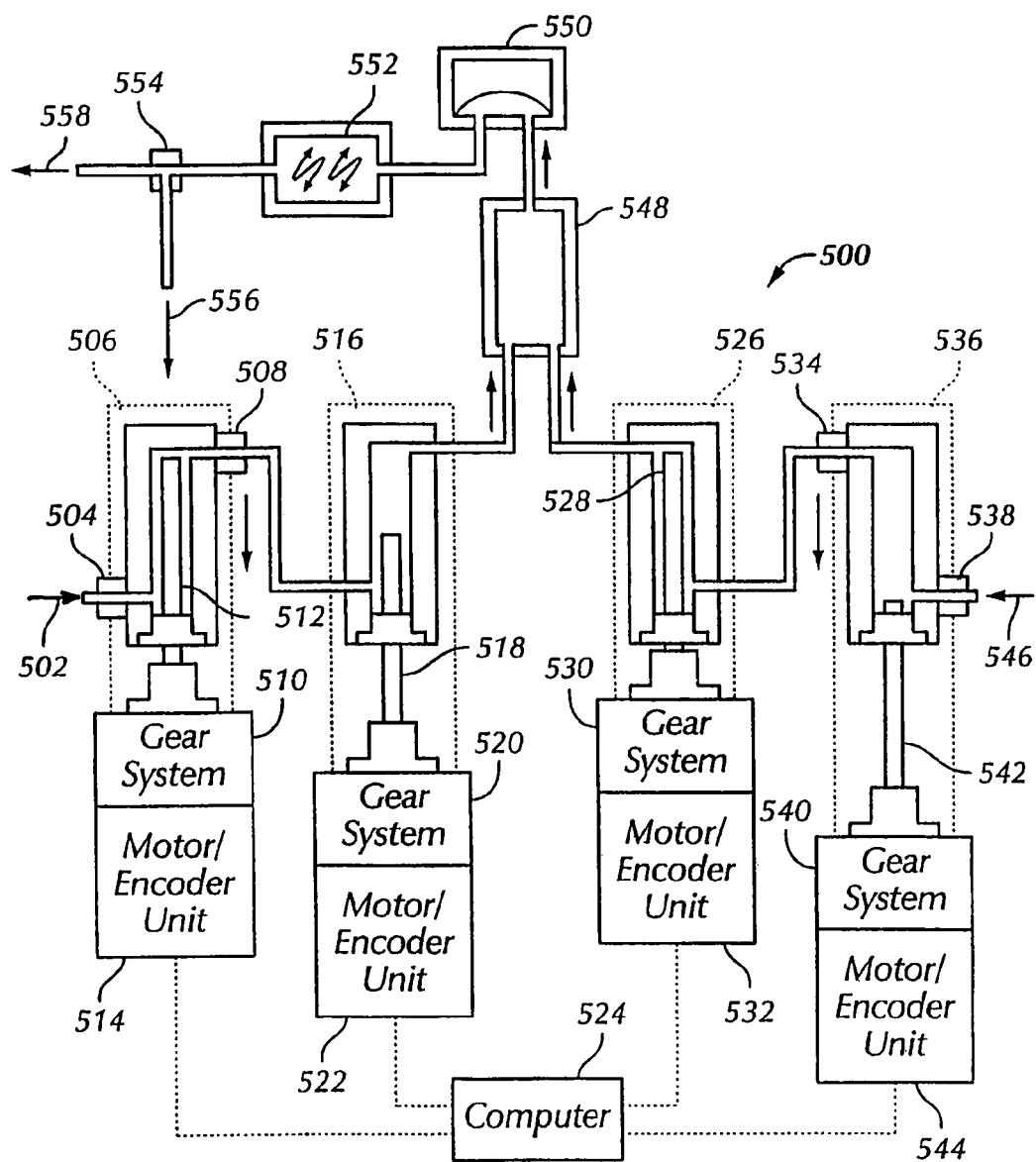
FIG. 5 is a schematic diagram of an embodiment of a high-pressure gradient pumping system.

FIG. 5 is a schematic diagram of an embodiment of a high-pressure gradient pumping system, such as a binary pumping system. A pumping system 500 includes two channels. The first channel includes a pumping unit 506 positioned in series (i.e., coupled to/in liquid communication) with a pumping unit 516. The second channel includes a pumping unit 526 positioned in series (i.e., coupled to/in liquid communication) with a pumping unit 536. Pumping unit 506 receives liquid through an inlet valve 504 and outputs liquid through an outlet valve 508. Pumping unit 536 receives liquid through an inlet valve 538 and outputs liquid through an outlet valve 534. Each pumping unit 506, 516, 526, and 536, interfaces with a gear system 510, 520, 530, and 540, respectively. Further, each gear system 510, 520, 530, and 540 interfaces with a motor/encoder unit 514, 522, 532, and 544, respectively. Lastly, each motor/encoder unit 514, 522, 532, and 544 is in communication with a computer 524. It should be appreciated that throughout the disclosure a gear system, such as gear system 510, and a motor/encoder unit, such as motor/encoder unit 514, may be considered a drive system used to drive a pumping unit, such as pumping unit 506. It should also be appreciated that alternative forms of pumping units, such as syringe pumping units, etc., and alternative forms of drive systems may be implemented in each of the disclosed embodiments and may still remain within the scope of the present invention. For example, any conventional system (i.e., drive system) used to drive a pumping apparatus is within the scope of the present invention.

The first channel and the second channel are in parallel with each other, and liquid flows from pumping unit 516 and pumping unit 526 into a mixing chamber 548. Mixing chamber 548 is connected to a damper 550. Damper 550 is connected to a mixer 552, which in turn is connected to a purge valve 554. Liquid flows from purge valve 554 out as waste 556 or as output 588 to a remainder of the chromatography system (not shown in FIG. 5).

Each motor/encoder unit 514, 522, 532, and 544 is connected to computer 524. As a result, each pumping unit 506, 516, 526, and 536 may be controlled. In one embodiment of the present invention, metering of liquid and delivery of the liquid to the chromatography system are performed by individually controlling the operation of pumping units 506, 516, 526, and 536 with the motor/encoder units 514, 522, 532, and 544 in conjunction with the computer 524.

During operation, liquid flows from liquid reservoirs through inlet valve 504 and inlet valve 538, as shown by arrows 502 and 546, respectively. Motor encoder unit 514 interfaces with gear system 510 to individually control pumping unit 506. Motor/encoder unit 522 interfaces with gear system 520 to individually control pumping unit 516. Motor/encoder unit 532 interfaces with gear system 530 to individually control pumping unit 526. Lastly, motor/encoder unit 544 interfaces with gear system 540 to individually control pumping unit 536.

Pumping unit 506 includes a piston 512. Pumping unit 516 includes a piston 518. Pumping unit 526 includes a piston 528. Pumping unit 536 includes a piston 542.

In one embodiment, motor/encoder unit 514 and motor/encoder unit 522 are synchronized via computer 524 to enable and piston 518 to operate at variable speeds relative to each other. In one embodiment, piston 512 may operate at some multiple of piston 518. For example, piston 512 may operate at a continuous multiple of 2x, 4x, 7x, etc. of piston 518. In an alternative embodiment, piston 512 may operate at a varying multiple of piston 518. It should also be appreciated that the piston (i.e., 512, 518, 528, and 542) in each pumping unit (i.e., 506, 516, 526, 536) may operate at an equal speed, a speed that is a continuous multiple or varying multiple relative to another piston. Operating a pumping unit relative to another pumping unit controls and/or manages the metering of liquid into and out of each pumping unit (i.e., 506, 516, 526, 536).

In one embodiment, during operation, liquid enters the pumping unit (i.e., 506, 516, 526, 536) in the bottom of a chamber and leaves the unit close to the top of a chamber. However, it should be appreciated that in alternate embodiments, liquid may enter and exit the chamber at different locations. In one embodiment, each chamber includes a piston, which has an outer diameter, which is smaller than the inner diameter of the chamber. As a result, liquid can fill the gap in between the outer diameter of the piston and the inner diameter of the chamber. In one embodiment, a piston has a stroke volume in the range of 20-100 ul as a function of the flow rate. A pump chip located in computer 524 controls the flow rates in a range of nano-liters to milliliters. However, it should be appreciated that a wide range of stroke volumes and flow rates may be implemented and remain within the range of the present invention.

During operation, pumping system 500 performs an initialization procedure to determine the upper dead center (UDC) and the lower dead center (LDC) for each of pistons 512, 518, 528, and 542. In addition, during initialization, motor/encoder units 514, 522, 532 and 544 are monitored to determine feedback movements, reference position signals are monitored, and assemblies are tested and monitored. Each piston 512, 518, 528, and 542 moves upward slowly into a mechanical stop of a chamber and from there it moves back a defined path length. Computer 524 stores these piston positions in memory. After this initialization, pumping system 500 starts operation with a set parameters for each pumping unit.

Inlet valves 504 and 538, are opened. Piston 512 and piston 542 each perform an intake stroke to draw liquid into pumping units 506 and 536, respectively. At the same time, pistons 518 and 528 move upward delivering liquid to mixing chamber 548. After a controller-defined stroke length (depending on the flow rate), each motor/encoder unit 514, 522, 532, and 544 is stopped and inlet valves 504 and 538 are closed. The direction of each motor/encoder unit 514, 522, 532, and 544 is reversed and pistons 512 and 542 move upward until they reach the stored upper limit (i.e., UDC), and at the same time, pistons 518 and 528 move downward.

The sequence repeats itself moving pistons 512, 518, 528, and 542 up and down between the two limits (i.e., UDC and LDC). During the upward movement of pistons 512 and 542, the liquid in pumping units 506 and 536 is pressed through outlet valves 508 and 534, respectively, into pumping units 516 and 526, respectively. Pistons 518 and 528 each draw in a portion of a volume displaced by pistons 512 and 542, and a remaining volume is directly delivered to the system. During the drawing stroke of pistons 512 and 542, pistons 518 and 528 deliver the drawn volume into the system.

Figure 6:
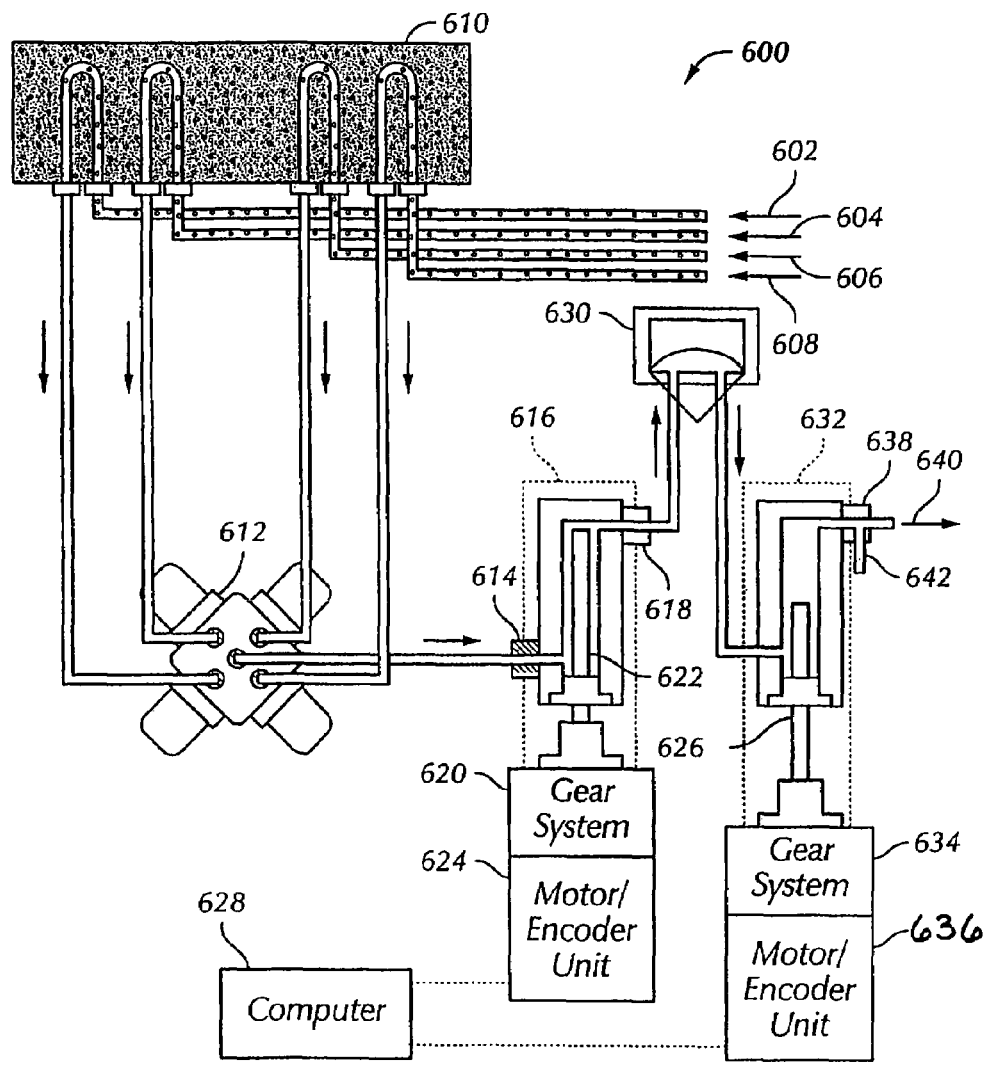
FIG. 6 is a schematic diagram of an embodiment of a low-pressure gradient pumping system.

FIG. 6 is a schematic diagram of an embodiment of a low-pressure gradient pumping system, such as a quaternary pumping system. A pumping system 600 includes two pumping units (616, 632) positioned in series. Liquids 602, 604, 606, and 608 are processed through a vacuum chamber 610 and through a proportioning valve 612. Proportioning valve 612 is in series with pumping unit 616, which is in series with a damper unit 630, which is further in series with pumping unit 632. A purge valve 638 provides an outlet via a path 640 to the system (not shown in FIG. 6) and to waste 642. A gear system 620, 634 and a motor/encoder unit 624, 636 are connected to each pumping unit 616, 632, respectively. Each motor/encoder unit 624, 636 is coupled to a computer 628, which controls pumping units 616 and 632.

Pumping system 600 is based on a dual-pump configuration. Metering of liquid and delivery are regulated by operating (a) pumping unit 616 individually using gear system 620, motor/encoder unit 624, and computer 628, and (b) pumping unit 632 individually using gear system 634, motor/encoder unit 636, and computer 628. Degassing of liquids is performed in vacuum chamber 610, and liquid compositions are generated by proportioning valve 612. In one embodiment, the pumping unit 616 includes an active inlet valve 614 and an outlet valve 618. Damper unit 630 is connected between pumping units 616 and 632.

When turned on, the pumping system 600 runs through an initialization procedure to determine the upper dead center (UDC) of piston 622. Piston 622 moves slowly upward into a mechanical stop of the chamber and from there it moves back a predetermined path length. Computer 628 stores the position of piston 622 in memory. The lower dead center (LDC) varies as a function of the flow rate, stroke length, etc. After initialization, pumping system 600 starts operation with the parameters acquired during the initialization procedure. Active inlet valve 614 is opened and piston 622, while moving down, draws liquid into the chamber. At the same time, piston 626 is moving upward delivering liquid into the system. After a controller-defined stroke length (depending on the flow rate), motor/encoder unit 624 is stopped and active inlet valve 614 is closed. Motor/encoder unit 624 is reversed and moves piston 622 up until it reaches the stored upper limit and at the same time, motor/encoder unit 636, which controls piston 626, moves piston 626 downward. The sequence then repeats itself with pistons 622 and 626 moving up and down between the two limits (i.e., reciprocating). During the up movement of piston 622, the liquid in the chamber of pumping unit 616 is delivered through outlet valve 618 into damper unit 630. Piston 626 draws in, from damper unit 630, a portion of the volume displaced by piston 622, and the remaining amount of the volume is delivered to the system. During the intake stroke (i.e., drawing stroke) of piston 622, piston 626 delivers the drawn volume to the system via path 640. For liquid compositions that require percentages of liquids 602, 604, 606, and 608, computer 628 controls and divides the length of the intake stroke into fractions and coordinates with proportioning valve 612 to connect the specified liquid channel to pumping units 616 and 632 to acquire the liquid in the proper percentages.

Figure 7:
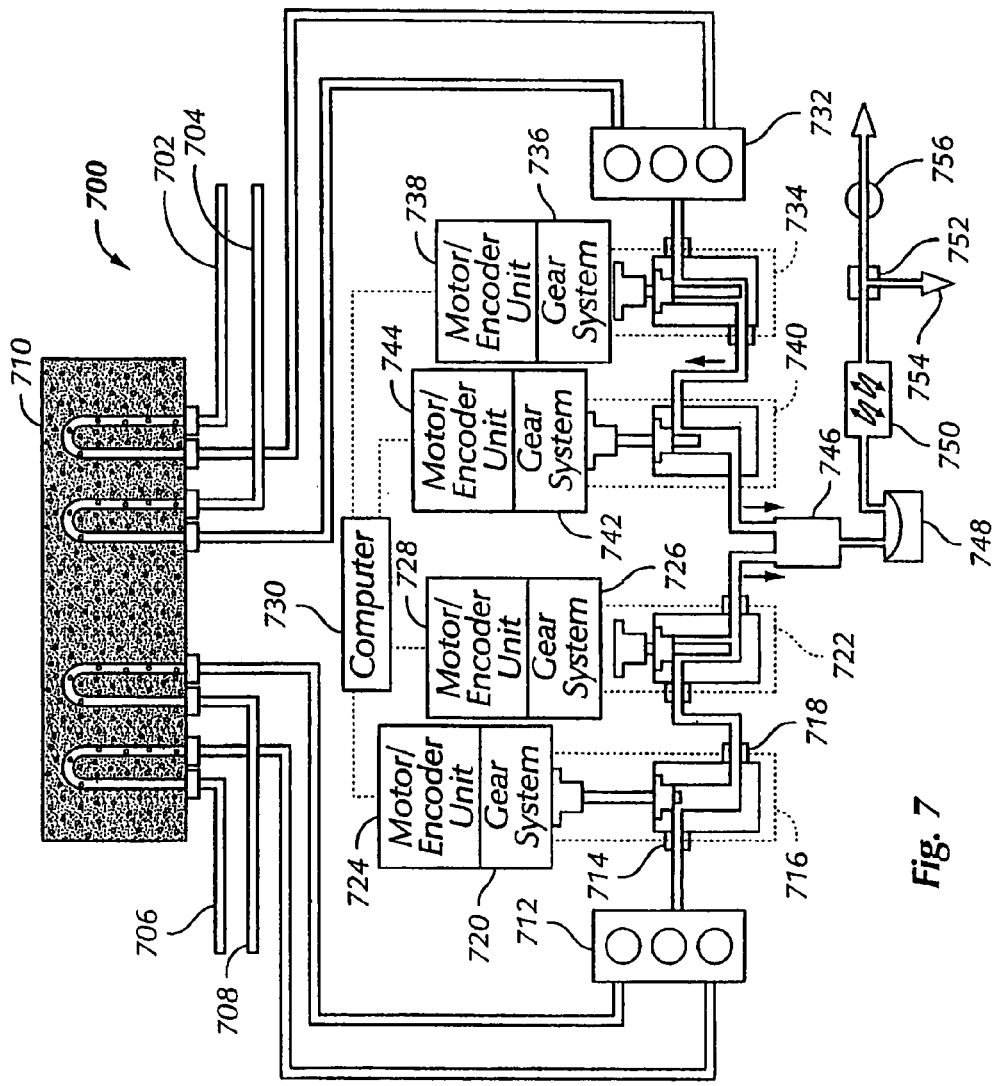
FIG. 7 is a schematic diagram of an embodiment of a high-pressure gradient pumping system.

FIG. 7 is a schematic diagram of a pumping system, such as a capillary pumping system. In FIG. 7, liquid flows into a pumping system 700 through a conveyance or inlet tubes 702, 704, 706, and 708. The liquid flows through a vacuum chamber 710. The liquid then flows through a solvent selection valve (SSV) 712 and a solvent selection valve (SSV) 732. SSV 712 is in series with a pumping unit 716, which includes an inlet valve 714 and an outlet valve 718. Pumping unit 716 is controlled by a gear system 720, which is connected to a motor/encoder unit 724. Pumping unit 716 is in series with a pumping unit 722, which is controlled by a gear system 726 that is connected to a motor/encoder unit 728.

SSV 732 is connected to a pumping unit 734, which is connected to a gear system 736, which interfaces with a motor/encoder unit 738. A pumping unit 740 is connected to a gear system 742, which is connected to motor/encoder unit 744. Each motor/encoder unit 724, 728, 744 and 738 is in communication with a computer 730. Pumping unit 722 and pumping unit 740 are connected to a mixing chamber 746. Mixing chamber 746 is in series with a damper 748, which is in series with a mixer 750. A variable nozzle 752 is positioned in series with mixer 750. Variable nozzle 752 controls a split ratio of a total flow between the flow of a flow sensor 756 and the flow to a waste 754. Flow sensor 756 is positioned on an output of pumping system 700.

Figure 8:
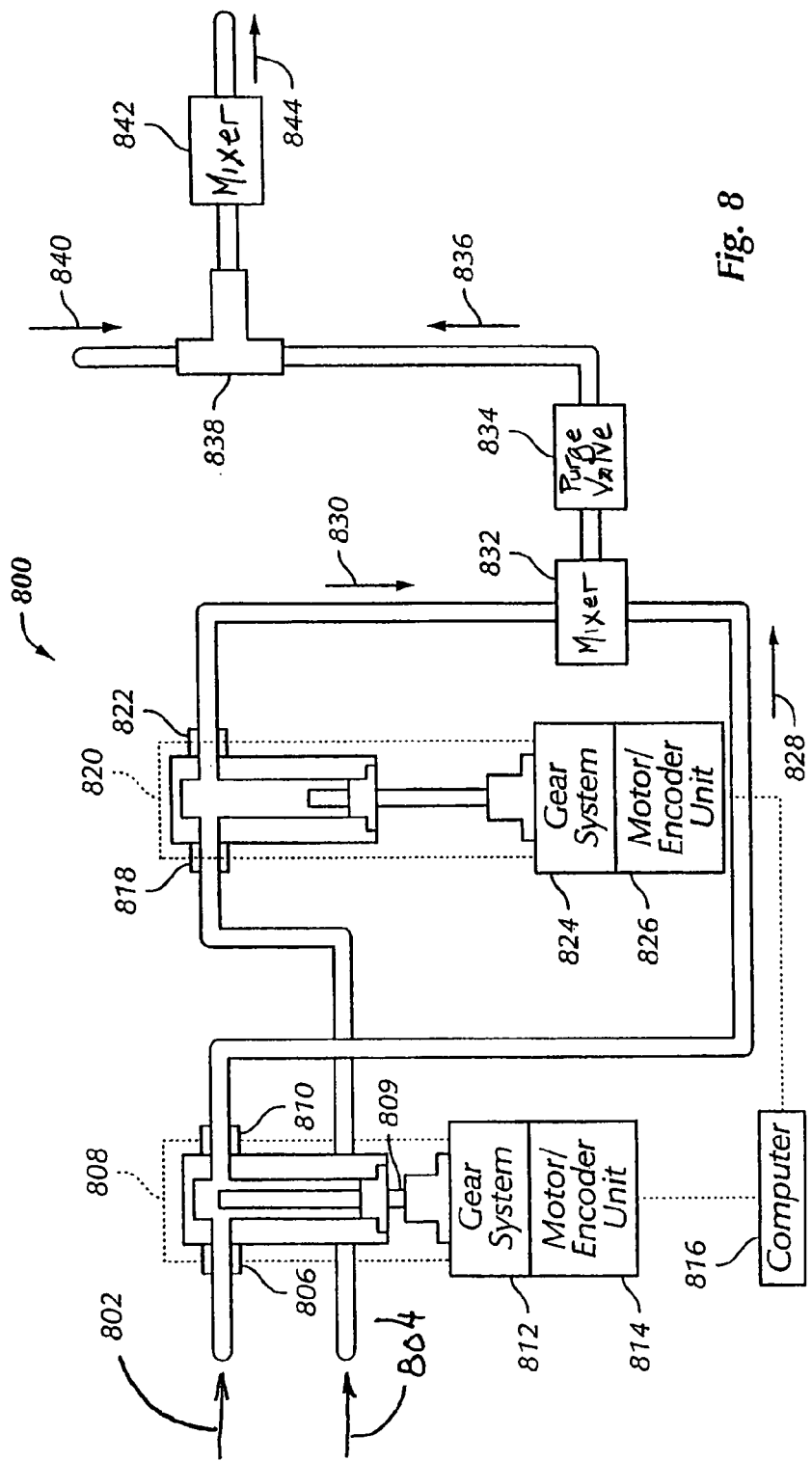
FIG. 8 is a schematic diagram of an embodiment of a high-pressure gradient pumping system.

FIG. 8 is a schematic diagram of an embodiment of a pumping system 800 being employed as a high-pressure gradient pumping system, such as a preparative pumping system. To reduce the complexity of the description of pumping system 800, a single channel is depicted in FIG. 8. A liquid 802 is input into a pumping unit 808, which is coupled to an inlet valve 806 and an outlet valve 810. In addition, a liquid 804 is input into a pumping unit 820, which is coupled to an inlet valve 818 and outlet valve 822. Pumping unit 808 interfaces with a gear system 812, which is controlled by a motor/encoder unit 814.

In one embodiment of the high-pressure gradient pumping system 800, pumping unit 820 interfaces with a gear system 824, which is controlled by a motor/encoder unit 826. Pumping unit 808 includes a piston 809, and produces an output 828. Pumping unit 820 produces an output 830. Output 828 and output 830 combine in a mixer 832. Mixer 832 is in series with a purge valve 834. Purge valve 834 is in series with, and provides a liquid output 836 to, a T-junction 838. T-junction 838 also receives liquid 840 from a second channel (not shown) of pumping system 800. It should be appreciated that FIG. 8 displays one channel of pumping system 800. A second channel of pumping system 800, which is not shown, replicates the first channel shown in FIG. 8. The output of the second channel, i.e., liquid 840, is shown. A mixer 842 is in series with T-junction 838, and mixes liquid 840 and provides an output 844.

In another embodiment, pumping system 800 is implemented without gear systems 812 and 824. In an alternative configuration, the pistons (e.g., piston 809) are coupled and driven by an encoder controlled motor.

Figure 9A:
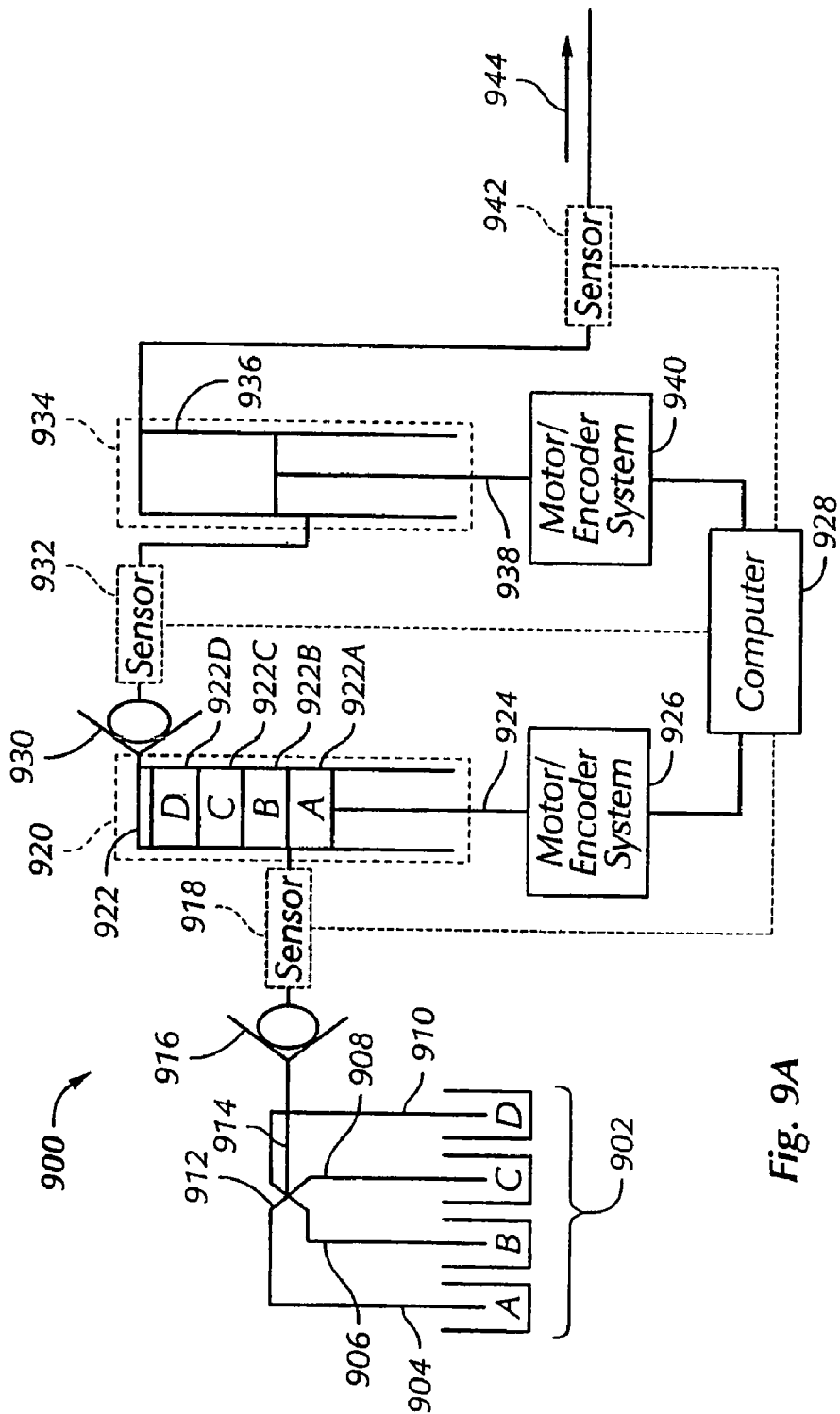
FIG. 9A is a schematic diagram of a pumping system, such as a single-channel pumping system, where the pumping units are positioned in series.

FIG. 9A is a schematic diagram of a pumping system 900, such as a single-channel pumping system, where the pumping units are positioned in series. In one embodiment, pumping system 900 is a low-pressure gradient pumping system, where mixing occurs prior to a routing of the liquid through a pumping unit. In one embodiment, a switch 912 may represent a selection switch. In another embodiment, switch 912 may represent a proportioning valve. It should be appreciated that the schematic diagram shown in FIG. 9A may be used to represent an isocratic pump as shown in FIG. 2, a single channel of a binary pump as shown in FIG. 5, a quaternary pump as shown in FIG. 6, a single channel of a capillary pump as shown in FIG. 7, or a preparative pump as shown in FIG. 8. It should also be appreciated that the methods presented in this application may be implemented on each of these pumping system configurations and, therefore, implementing any one of the methods presented in the instant application on any one of the pumping system configurations is within the scope of the present invention.

A variety of conventions have been employed in presenting the instant application. Throughout the instant application many figures include components that are outlined with dashed lines. Components outlined with dashed lines are used to display where the components may be positioned within the pumping system. However, each component may not be used in every configuration. For example, the pumping system 900 includes a flow sensor 918, a flow sensor 932, and a flow sensor 942. Each flow sensor 918, 932 and 942 is outlined with dashed lines. Therefore, some of the methods presented below may utilize one of the flow sensors (i.e., 918, 932, 942) or a combination of the flow sensors (i.e., 918, 932, 942). For example, a method may utilize an individual flow sensor 918, 932, or 942. In the alternative, a method may utilize a combination of flow sensors, for example, 918 and 932, 932 and 942, 918 and 942, or 918, 932, and 942. Flow sensors 918, 932, and 942, when implemented, detect liquid flow within pumping system 900, and are coupled to a computer 928, to provide to computer 928, an indication of the detected liquid flow. Below, to identify which components are configured and/or implemented in pumping system 900 during a discussion of a method being employed in pumping system 900, referencing text explaining the method will identify the components that are configured and operating in pumping system 900 during the performance of the method.

Pumping units, such as pumping units 920 and 934, are also outlined with dashed lines. The dashed lines presented around the pumping units (i.e., 920, 934) are provided to refer to the pumping units (i.e., 920, 934) with a single label (i.e., pumping unit). Although the methods presented in the instant application operate with at least two pumping units, variations and modifications of the methods may be performed to work with a single pumping unit, and are still within the scope of the present invention. Any discussion of methods that utilize pumping units will identify the pumping unit configuration.

FIG. 9A shows two pumping units (i.e., 920, 934) in series. In one embodiment, pumping units 920 and 934 comprise a channel. An inlet valve 916 is in series with flow sensor 918, which is in series with pumping unit 920. An outlet valve 930 is in series with flow sensor 932, which is in series with pumping unit 934. Lastly, flow sensor 942 is in series with pumping unit 934. Liquid flows from pumping unit 934, through sensor 942, to produce an output 944.

As mentioned previously, flow sensors 918, 932, and 942 are represented in dashed lines, which depicts that different combinations of flow sensors 918, 932 and 942 may be implemented when performing the methods presented in the instant applications. Therefore, a specific flow sensor (i.e., 918, 932, and 942) will be discussed and described when the flow sensor is configured and operating during the performance of the method.

Pumping system 900 includes a variety of liquids (i.e., A, B, C, D) stored in a liquid reservoir 902. Each liquid (i.e., A, B, C, D) is conveyed through a conveyance 904, 906, 908 or 910, respectively, to switch 912. When switch 912 is implemented as a proportioning valve, the liquids (i.e., A, B, C, D) are mixed. The liquids (i.e., A, B, C, D) are then drawn through a conveyance 914 and inlet valve 916 into pumping unit 920. Pumping unit 920 includes a chamber 922 and a piston 924, which performs a reciprocating motion (i.e., performs a piston stroke which consist of an intake stroke and a delivery stroke). Outlet valve 930 is in series with pumping unit 920. Flow sensor 932 is in series with outlet valve 930. Pumping unit 934 is in series with flow sensor 932, which is in series with outlet valve 930. Pumping unit 934 includes a chamber 936 and a piston 938. Throughout the discussion of the figures in the present invention, inlet valves and outlet valves will be described and discussed. It should be appreciated that the inlet valves, such as inlet valve 916, and the outlet valves, such as outlet valve 930, may be implemented as active valves or passive valves. In addition, the flow sensors, such as flow sensor 918, may be positioned before inlet valve 916 or after inlet valve 916, and flow sensor 932 may be positioned before outlet valve 930 or after outlet valve 930. A wide variety of flow sensors may be implemented in accordance with the teachings of the present invention. One specific flow sensor that may be implemented in the present invention is flow sensor model SLG 1430 implemented by Sensirion, Switzerland.

A motor/encoder system 926 and a motor/encoder system 940 each includes gears (i.e., gear system), a motor, and encoders required to individually operate pumping unit 920 and pumping unit 934, respectively. Computer 928 is coupled to both of motor/encoder system 926 and motor/encoder system 940.

During initialization, procedures are performed to identify a upper dead center (UDC) and a lower dead center (LDC) of piston 924 and piston 938 using motor/encoder systems 926 and 940, respectively. Additional activities, such as opening and closing inlet valve 916 and outlet valve 930, may also be performed during initialization.

During operation, inlet valve 916 is opened. An intake stroke of piston 924 draws liquid (i.e., A, B, C, D) through switch 912 and fills chamber 922. In one embodiment, liquids 922A, 922B, 922C, and 922D are drawn into chamber 922. Liquids 922A, 922B, 922C, and 922D correspond to the liquids A, B, C and D; respectively, that are stored in liquid reservoir 902. Various percentages of liquids A, B, C and D are mixed together when switch 912 is implemented as a proportioning valve. On the delivery stroke of piston 924, liquid (i.e., 922A, 922B, out of chamber 922 at different flow rates and then measured by a flow sensor that we are attempting to calibrate. From step 1134, the method progresses to step 1135.

Figure 11A:
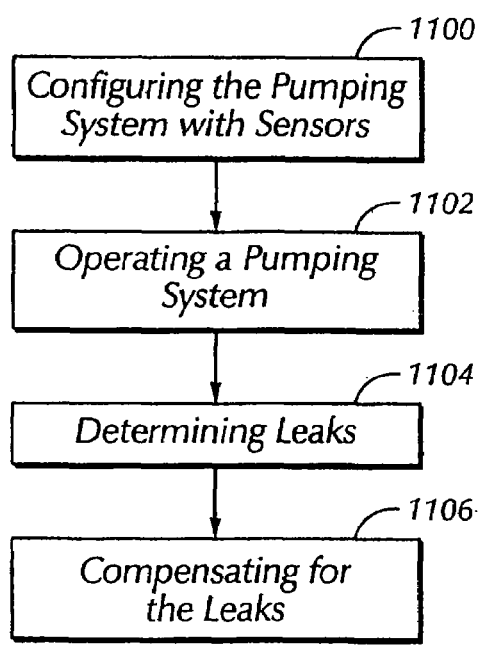
FIG. 11A is a flowchart of a method of determining leaks in a pumping system.
Figure 11B:
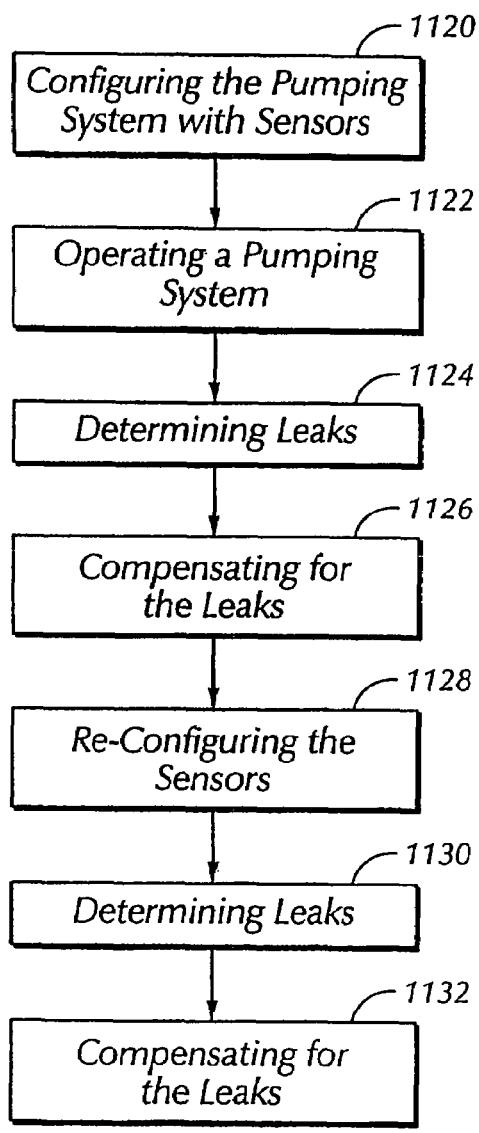
FIG. 11B is a flowchart of a method of reconfiguring sensors in a pumping system.

At step 1135, a calibration factor is determined. To determine the calibration factor, a graph, such as the graph shown in FIG. 11D, may be used. The graph shown in FIG. 11D presents voltage on the y-axis and flow rate on the x-axis. The graph also includes a calibration curve 1136, a voltage 1140, and a voltage 1138. Calibration curve 1136 is a calibration curve for a know solvent, and is provided (e.g., by the manufacturer).

Voltage 1138 is a voltage of the known solvent at a known flow rate, i.e., a flow rate 1142. An unknown solvent (i.e., a solvent in a chamber) is then processed through a flow sensor at flow rate 1142. Voltage 1140 is a voltage of the unknown solvent at flow rate 1142. A calibration factor 1144 is then defined by a relation between the voltage of the unknown solvent, i.e., voltage 1140, and the voltage of the known solvent, i.e., voltage 1138. In one embodiment, the calibration factor 1144 is equivalent to the voltage of the unknown solvent, i.e., voltage 1140, divided by the voltage of the known solvent, i.e., voltage 1138. This method may be performed at different flow rates.

Figure 11C:
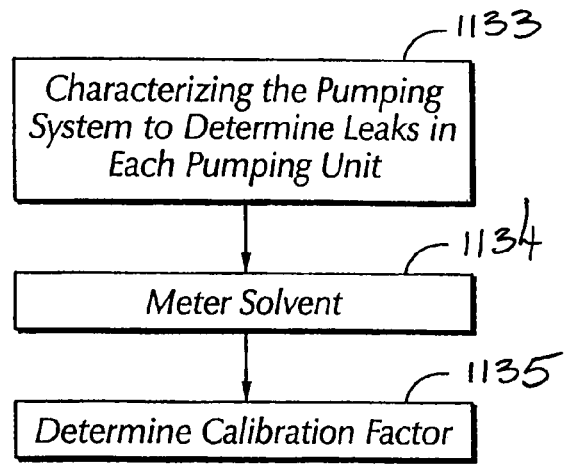
FIG. 11C is a flowchart of a method of calibrating sensors.
Figure 11D:
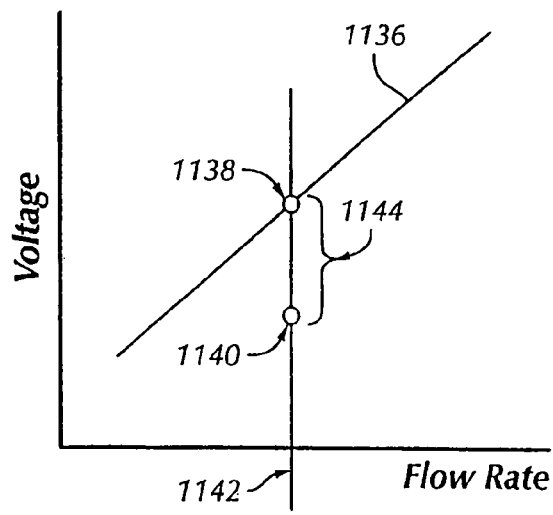
FIG. 11D is a graph of voltage versus flow rate.

An alternate method of calibrating a flow sensor is presented using the flowchart depicted in FIG. 11C, the graph presented in FIG. 11D, and the pumping unit depicted in FIG. 9A. In the alternate embodiment, a method of calibrating solvents in a low-pressure gradient pump is presented. The method commences with step 1133.

At step 1133 of FIG. 11C, the operation of a pumping system is characterized to determine leaks or the tightness of each pumping unit. For example, using FIG. 9A as an example, piston 924 performs an intake stroke to draw liquid into chamber 922. In the alternate embodiment of the present invention, switch 912 is switched to allow liquids conveyed on conveyances 904, 906, 908, and 910 to be accessed from reservoir 902 and transported via conveyance 914. The liquid is then stacked in chamber 922 as shown by liquid 922A, liquid 922B, liquid 922C, and liquid 922D. Inlet valve 916 and outlet valve 930 are then closed. Piston 924 moves through part of a delivery stroke to pressurize chamber 922. Lastly, chamber 922 is monitored for a decrease in pressure. In one embodiment, the decrease in pressure may be measured using a pressure sensor (not shown) positioned to measure the pressure in chamber 922. It should be appreciated that a pressure sensor may be deployed in each chamber of the pumping units presented in FIGS. 9A, 9B, and 10. The pressure for the chamber in each of the pumping units may then be measured by the pressure sensor using methods presented in the instant application. Lastly, additional methods of determining a decrease in the pressure of the chamber may be implemented and are within the scope of the present invention. If there is a decrease in pressure, this signals a leak in the pumping unit. If there is no pressure decrease, then there are no leaks (i.e., the pumping unit is tight). This process may be performed for each pumping unit in the pumping systems shown in FIGS. 9A, 9B, and 10 to determine the tightness of each pumping unit. From step 1133, the method progresses to step 1134.

At step 1134 of FIG. 11C, the liquid is then metered out of the pumping unit. Metering the liquid involves individually controlling and recording the movement of an encoder found in the motor/encoder system to determine the exact amount of liquid that is being delivered out of a chamber in a pumping unit. For example, metering the liquid may involve recording the movement of an encoder found in motor/encoder system 926 to determine the amount of liquid output from chamber 922. In an alternate embodiment, the liquid may be metered out of chamber 922 at different flow rates and then measured by a flow sensor that we are attempting to calibrate.

In one embodiment, metering is performed to deliver each liquid, and then calibration is performed relative to each liquid. For example, liquid 922A, liquid 922B, liquid 922C, and liquid 922D are each metered out of the chamber and used to calibrate flow sensor 918 and/or flow sensor 932.

From step 1134, the method progresses to step 1135.

At step 1135, a calibration factor is determined. To determine the calibration factor, a graph, such as the graph shown in FIG. 11D, may be used. As mentioned above, in FIG. 11D, calibration curve 1136 is a calibration curve for a known solvent, and voltage 1138 is a voltage of the known solvent at a known flow rate 1142. An unknown solvent, such as liquid 922A, liquid 922B, liquid 922C, and liquid 922D, is then processed through the flow sensor at flow rate 1142. Voltage 1140 is the voltage of the unknown solvent at flow rate 1142. Calibration factor 1144 is then defined as a ratio of the voltage of the unknown solvent, i.e., voltage 1140, to the voltage of the known solvent, i.e., voltage 1138. This method may be performed at different flow rates.

In the following, the method of calibrating a flow sensor depicted in FIG. 11B will be described with respect to several configurations in FIG. 9A. For example, a method of calibrating flow sensor 918 is presented. A method of calibrating flow sensor 932 is presented, and a method of calibrating flow sensor 942 is presented.

To calibrate flow sensor 918, a test as described above is performed to determine the tightness of pumping unit 920. Inlet valve 916 is then opened and outlet valve 930 is closed, and the liquid stored in chamber 922 is metered out of chamber 922 and through flow sensor 918. The voltage of a known solvent at a known flow rate is identified, i.e., voltage 1138 is identified for flow rate 1142. An unknown solvent, such as liquid 922A, liquid 922B, liquid 922C, and liquid 922D, is then processed through flow sensor 918 at flow rate 1142. Voltage 1140 is the voltage of the unknown solvent at flow rate 1142. Calibration factor 1144 is then defined as a ratio of the voltage of the unknown solvent, i.e., voltage 1140, to the voltage of the known solvent, i.e., voltage 1138. This method may be performed at different flow rates.

To calibrate flow sensor 932, a test as described above is performed to determine the tightness of pumping unit 920. Outlet valve 930 is then opened, inlet valve 916 is closed, and the liquid (i.e., unknown solvent) stored in chamber 922 is metered out of chamber 922 and through flow sensor 932. The voltage of a known solvent at a known flow rate is identified, i.e., voltage 1138 is identified for flow rate 1142. An unknown solvent, such as liquid 922A, liquid 922B, liquid 922C, and liquid 922D, is then processed through flow sensor 932 at flow rate 1142. Voltage 1140 is the voltage of the unknown solvent at flow rate 1142. Calibration factor 1144 is then defined as a ratio of the voltage of the unknown solvent, i.e., voltage 1140, to the voltage of the known solvent, i.e., voltage 1138. This method may be performed at different flow rates.

To calibrate flow sensor 942, a test as described above is performed to determine the tightness of pumping unit 920 and pumping unit 934. A variety of testing methods may be used to calibrate a flow sensor placed on an output of a low-pressure gradient pumping system. In one embodiment, pumping unit 920 is used to calibrate flow sensor 942. In a second embodiment, pumping unit 934 is used to calibrate flow sensor 942. In a third embodiment, a combination of pumping unit 920 and pumping unit 934 are used to test flow sensor 942.

In one embodiment, to calibrate flow sensor 942, a test is made to determine the tightness of pumping unit 920 and pumping unit 934. Liquid stored in pumping unit 920 is metered out of chamber 922, through flow sensor 932, through chamber 936, and through flow sensor 942. The voltage of a known solvent at a known flow rate is identified, i.e., voltage 1138 is identified for flow rate 1142. An unknown solvent, such as liquid 922A, liquid 922B, liquid 922C, and liquid 922D, is then processed through flow sensor 942 at flow rate 1142. Voltage 1140 is the voltage of the unknown solvent at flow rate 1142. Calibration factor 1144 is then defined as a ratio of the voltage of the unknown solvent, i.e., voltage 1140, to the voltage of the known solvent, i.e., voltage 1138. This method may be performed at different flow rates.

In a second embodiment, to calibrate flow sensor 942, a test is made to determine the tightness of pumping unit 934. The liquid stored in pumping unit 934 is metered out of chamber 936 and through flow sensor 942. The voltage of a known solvent at a known flow rate is identified, i.e., voltage 1138 is identified for flow rate 1142. An unknown solvent, such as liquid 922A, liquid 922B, liquid 922C, and liquid 922D, is then processed through flow sensor 942 at flow rate 1142. Voltage 1140 is the voltage of the unknown solvent at flow rate 1142. Calibration factor 1144 is then defined as a ratio of the voltage of the unknown solvent, i.e., voltage 1140, to the voltage of the known solvent, i.e., voltage 1138. This method may be performed at different flow rates.

In a third embodiment, to calibrate flow sensor 942, a test is made to determine the tightness of pumping unit 920 and pumping unit 934. The liquid stored in pumping unit 920 is metered out of chamber 922 and through flow sensor 932, through chamber 936, and through flow sensor 942. The liquid stored in pumping unit 934 is metered out of the chamber 936 and through flow sensor 942. The voltage of a known solvent at a known flow rate is identified, i.e., voltage 1138 is identified for flow rate 1142. An unknown solvent, such as liquid 922A, liquid 922B, liquid 922C, and liquid 922D, is then processed through flow sensor 942 at flow rate 1142. Voltage 1140 is the voltage of the unknown solvent at flow rate 1142. Calibration factor 1144 is then defined as a ratio of the voltage of the unknown solvent, i.e., voltage 1140, to the voltage of the known solvent, i.e., voltage 1138. This method may be performed at different flow rates.

Figure 9B:
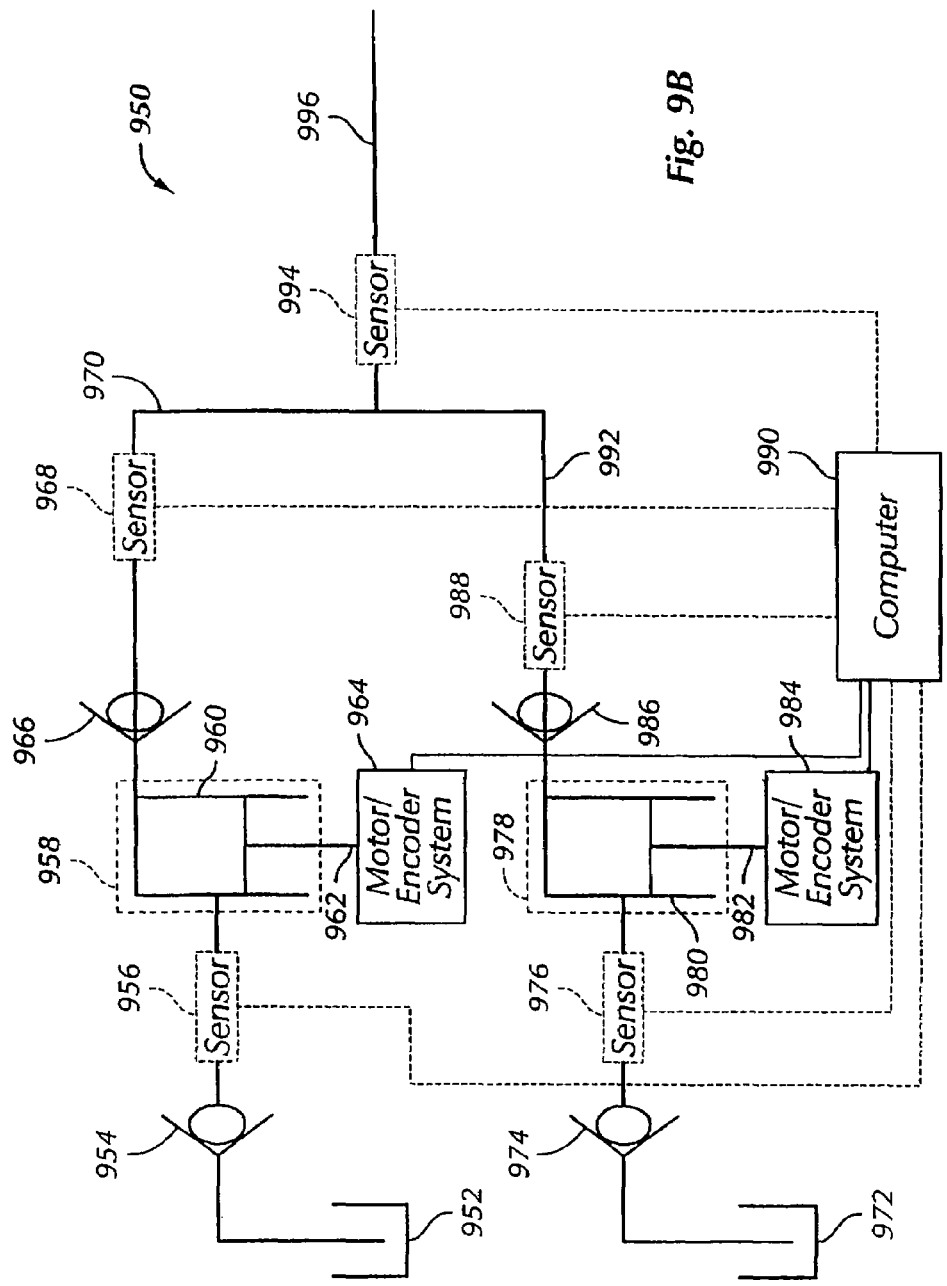
FIG. 9B is a schematic diagram of a channel of a pumping system with pumping units configured in parallel.

FIG. 9B will be discussed in conjunction with FIG. 11C. The method commences with step 1133.

At step 1133 of FIG. 11C, the operation of a pumping system is characterized to determine leaks or the tightness of each pumping unit. For example, using FIG. 9B as an example, piston 962 and/or piston 982 perform(s) an intake stroke to draw liquid into chamber 960 and/or chamber 980. Inlet valve 954 and/or inlet valve 974, and outlet valve 966 and/or outlet valve 986 are then closed. Piston 962 and/or piston 982 may each move through part of a delivery stroke to pressurize chamber 960 and/or chamber 980. Lastly, chamber 960 and/or chamber 980 is/are monitored for a decrease in pressure. If there is a decrease in pressure, this signals a leak in the pumping unit (i.e., 958, 978). If there is no pressure decrease, then there are no leaks (i.e., the pumping unit is tight). This process may be performed for each pumping unit (i.e., 958, 978) in pumping system 950 shown in FIG. 9B to determine the tightness of each pumping unit (i.e., 958, 978). From step 1133, the method progresses to step 1134.

At step 1134 of FIG. 11C, the liquid is then metered out of the pumping unit. Metering the liquid involves individually controlling and recording the movement of an encoder found in the motor/encoder system to determine the exact amount of liquid that is being delivered out of a chamber in a pumping unit. For example, metering the liquid may involve recording movement of an encoder found in the motor/encoder system 964 and/or motor/encoder system 984 to determine the amount of liquid output from the chamber 960 and/or chamber 980. In an alternate embodiment, the liquid may be metered out of chamber 960 and/or chamber 980 at different flow rates and then measured by a flow sensor that we are attempting to calibrate. From step 1134, the method progresses to step 1135.

At step 1135, a calibration factor is determined. To determine the calibration factor, a graph, such as the graph shown in FIG. 11D, may be used. The voltage of a known solvent at a known flow rate is identified, i.e., voltage 1138 is identified for flow rate 1142. An unknown solvent, such as liquid stored in reservoir 952 or reservoir 972, is then processed through a flow sensor (i.e., 956, 968, 976, 988, 994) at flow rate 1142. Voltage 1140 is the voltage of the unknown solvent at flow rate 1142. Calibration factor 1144 is then defined as a ratio of the voltage of the unknown solvent, i.e., voltage 1140, to the voltage of the known solvent, i.e., voltage 1138. This method may be performed at different flow rates.

The method of calibrating a sensor depicted in FIG. 11C will be described with respect to several configurations in FIG. 9B. For example, a method of calibrating flow sensor 956 is presented, a method of calibrating flow sensor 968 is presented, a method of calibrating flow sensor 976 is presented, a method of calibrating flow sensor 988 is presented, and a method of calibrating flow sensor 994 is presented.

To calibrate flow sensor 956, pumping system 950 is characterized to determine leaks in pumping system 950. Inlet valve 954 is then opened and outlet valve 966 is closed, and the liquid stored in chamber 960 is metered out of chamber 960 and through flow sensor 956. The voltage of a known solvent at a known flow rate is identified, i.e., voltage 1138 is identified for flow rate 1142. An unknown solvent, such as liquid stored in reservoir 952, is then processed through a flow sensor 956 at flow rate 1142. Voltage 1140 is the voltage of the unknown solvent at flow rate 1142. Calibration factor 1144 is then defined as a ratio of the voltage of the unknown solvent, i.e., voltage 1140, to the voltage of the known solvent, i.e., voltage 1138. This method may be performed at different flow rates.

To calibrate flow sensor 968, pumping system 950 is characterized to determine the tightness of pumping units 958 and 978. Outlet valve 966 is then opened, inlet valve 954 is closed, and the liquid stored in chamber 960 is metered out of chamber 960 and through flow sensor 968. The voltage of a known solvent at a known flow rate is identified, i.e., voltage 1138 is identified for flow rate 1142. An unknown solvent, such as liquid stored in reservoir 952, is then processed through flow sensor 968 at flow rate 1142. Voltage 1140 is the voltage of the unknown solvent at flow rate 1142. Calibration factor 1144 is then defined as a ratio of the voltage of the unknown solvent, i.e., voltage 1140, to the voltage of the known solvent, i.e., voltage 1138. This method may be performed at different flow rates. In one embodiment of the present invention, the foregoing methods may also be used to calibrate flow sensors 976 and 988.

A variety of testing methods may be used to calibrate a flow sensor placed on an output, such as flow sensor 994, which is positioned on the output of pumping system 950. In one embodiment, pumping unit 958 is used to calibrate flow sensor 994. In a second embodiment, pumping unit 978 is used to calibrate flow sensor 994. In a third embodiment, a combination of pumping unit 958 and pumping unit 978 is used to calibrate flow sensor 994.

To calibrate flow sensor 994, pumping system 950 is characterized to determine the tightness of pumping unit 958 and pumping unit 978. Liquid stored in pumping unit 958 is metered out of chamber 960, through flow sensor 968, and through flow sensor 994. The voltage of a known solvent at a known flow rate is identified, i.e., voltage 1138 is identified for flow rate 1142. An unknown solvent, such as liquid stored in reservoir 952, is then processed through flow sensor 994 at a known flow rate 1142. Voltage 1140 is the voltage of the unknown solvent at flow rate 1142. Calibration factor 1144 is then defined as a ratio of the voltage of the unknown solvent, i.e., voltage 1140, to the voltage of the known solvent, i.e., voltage 1138. This method may be performed at different flow rates. It should be appreciated that flow sensors 968 and 994 may both be calibrated using the foregoing methods and then compared to provide a more accurate calibration factor 1144 for each flow sensor (i.e., 968, 994).

In a second embodiment, to calibrate flow sensor 994, pumping system 950 is characterized to determine the tightness of pumping unit 958 and the pumping unit 978. Liquid stored in pumping unit 978 is metered out of chamber 980 through flow sensor 988 and through flow sensor 994. The voltage of a known solvent at a known flow rate is identified, i.e., voltage 1138 is identified for flow rate 1142. An unknown solvent, such as liquid stored in reservoir 972, is then processed through flow sensor 994 at flow rate 1142. Voltage 1140 is the voltage of the unknown solvent at flow rate 1142. Calibration factor 1144 is then defined as a ratio of the voltage of the unknown solvent, i.e., voltage 1140, to the voltage of the known solvent, i.e., voltage 1138. This method may be performed at different flow rates. It should be appreciated that flow sensors 988 and 994 may both be calibrated using the foregoing methods and then compared to provide a more accurate calibration factor 1144 for each flow sensor (i.e., 988, 994).

In a third embodiment, to calibrate flow sensor 994, pumping system 950 is characterized to determine the tightness of pumping unit 958 and pumping unit 978. The liquid stored in pumping unit 958 is metered out of chamber 960 through flow sensor 968 and through flow sensor 994. The liquid stored in pumping unit 978 is metered out of chamber 980 through flow sensor 988 and through flow sensor 994. The voltage of a known solvent at a known flow rate is identified, i.e., voltage 1138 is identified for flow rate 1142. An unknown solvent, such as liquid stored in reservoir 952, is then processed through flow sensor 994 at flow rate 1142. Voltage 1140 is the voltage of the unknown solvent at flow rate 1142. Calibration factor 1144 is then defined as a ratio of the voltage of the unknown solvent, i.e., voltage 1140, to the voltage of the known solvent, i.e., voltage 1138. This method may be performed at different flow rates.

The method of calibrating a flow sensor depicted in FIG. 11C will be described with respect to several configurations in FIG. 10. The calibration method depicted in FIG. 11C is applied to each configuration to calibrate one of the flow sensors. In the following discussion, methods are presented for calibrating flow sensors 1005, 1018, 1030, 1032, 1038, 1043, and 1054.

To calibrate flow sensor 1005, pumping system 1000 is characterized to determine the tightness of pumping units 1006, 1020, 1044, and 1056. Outlet valve 1016 is closed and inlet valve 1004 is opened. Flow sensor 1005 may be positioned before or after inlet valve 1004. Liquid stored in pumping unit 1006 is metered out of chamber 1008 through flow sensor 1005. The voltage of a known solvent at a known flow rate is identified, i.e., voltage 1138 is identified for flow rate 1142. An unknown solvent, such as liquid stored in liquid reservoir 1002, is then processed through flow sensor 1005 at flow rate 1142. Voltage 1140 is the voltage of the unknown solvent at flow rate 1142. Calibration factor 1144 is then defined as a ratio of the voltage of the unknown solvent, i.e., voltage 1140, to the voltage of the known solvent, i.e., voltage 1138. This method may be performed at different flow rates.

To calibrate flow sensor 1018, pumping system 1000 is characterized to determine the tightness of pumping units 1006, 1020, 1044, and 1056. Inlet valve 1004 is closed and outlet valve 1016 is opened. Flow sensor 1018 may be positioned before or after outlet valve 1016. Liquid stored in pumping unit 1006 is metered out of chamber 1008 through flow sensor 1018. The voltage of a known solvent at a known flow rate is identified, i.e., voltage 1138 is identified for flow rate 1142. An unknown solvent, such as liquid stored in reservoir 1002, is then processed through flow sensor 1018 at flow rate 1142. Voltage 1140 is the voltage of the unknown solvent at flow rate 1142. Calibration factor 1144 is then defined as a ratio of the voltage of the unknown solvent, i.e., voltage 1140, to the voltage of the known solvent, i.e., voltage 1138. This method may be performed at different flow rates.

To calibrate flow sensor 1043, pumping system 1000 is characterized to determine the tightness of pumping units 1006, 1020, 1044, and 1056. Outlet valve 1052 is closed and inlet valve 1042 is opened. Flow sensor 1043 may be positioned before or after inlet valve 1042. Liquid stored in pumping unit 1044 is metered out of chamber 1046 through flow sensor 1043. The voltage of a known solvent at a known flow rate is identified, i.e., voltage 1138 is identified for flow rate 1142. An unknown solvent, such as liquid stored in reservoir 1040, is then processed through flow sensor 1043 at a known flow rate 1142. Voltage 1140 is the voltage of the unknown solvent at flow rate 1142. Calibration factor 1144 is then defined as a ratio of the voltage of the unknown solvent, i.e., voltage 1140, to the voltage of the known solvent, i.e., voltage 1138. This method may be performed at different flow rates.

To calibrate flow sensor 1054, pumping system 1000 is characterized to determine the tightness of pumping units 1006, 1020, 1044, and 1056. Inlet valve 1042 is closed and outlet valve 1052 is opened. Liquid stored in pumping unit 1044 is metered out of chamber 1046 through flow sensor 1054. The voltage of a known solvent at a known flow rate is identified, i.e., voltage 1138 is identified for flow rate 1142. An unknown solvent, such as liquid stored in reservoir 1040, is then processed through flow sensor 1054 at flow rate 1142. Voltage 1140 is the voltage of the unknown solvent at flow rate 1142. Calibration factor 1144 is then defined as a ratio of the voltage of the unknown solvent, i.e., voltage 1140, to the voltage of the known solvent, i.e., voltage 1138. This method may be performed at different flow rates.

To calibrate flow sensors 1030, 1032, or 1038, pumping system 1000 is characterized to determine the tightness of pumping units 1006, 1020, 1044, and 1056. A variety of testing methods may be used to test a flow sensor placed on an output of pumping system 1000. In one embodiment, pumping unit 1006 is used to test flow sensors 1030, 1032, or 1038. In a second embodiment, pumping unit 1020 is used to test the flow sensors 1018, 1030, or 1032. In a third embodiment, a combination of the pumping unit 1006 and the pumping unit 1020 is used to test flow sensors 1030, 1032, or 1038.

In one embodiment, a pumping unit in a second channel may be used to calibrate a flow sensor positioned on the output of the second channel. In another embodiment, a pumping unit in a first channel in combination with a pumping unit in the second channel may be used to calibrate a flow sensor positioned on the output of the second channel. For example, when calibrating flow sensor 1038, piston 1024 may be used in combination with piston 1060 or piston 1060 may be used individually to calibrate flow sensor 1038. When using piston 1024 in combination with piston 1060, piston 1024 performs a delivery stroke and piston 1060 performs an intake stroke to calibrate flow sensor 1038. When using piston 1060 individually to calibrate flow sensor 1038, piston 1060 performs an intake stroke for backward calibration or piston 1060 performs a delivery stroke for forward calibration. It should be appreciated that a similar approach may be used to calibrate flow sensor 1030 using piston 1060 in combination with piston 1024 or piston 1024 individually.

In one embodiment, pumping unit 1006 is used to test flow sensors 1030, 1032, and 1038. A test is made to determine the tightness of the pumping unit 1006, pumping unit 1020, and pumping unit 1056. The liquid stored in pumping unit 1006 is metered out of chamber 1008 through flow sensor 1018, through chamber 1022, and through flow sensors 1030, 1032, and/or 1038. The voltage of a known solvent at a known flow rate is identified, i.e., voltage 1138 is identified for flow rate 1142. An unknown solvent, such as liquid stored in reservoir 1002, is then processed through a flow sensor(s) 1030, 1032, and/or 1038 at flow rate 1142. Voltage 1140 is the voltage of the unknown solvent at flow rate 1142. Calibration factor 1144 is then defined as a ratio of the voltage of the unknown solvent, i.e., voltage 1140, to the voltage of the known solvent, i.e., voltage 1138. This method may be performed at different flow rates. It should be appreciated that a similar approach may be performed to test flow sensors 1030, 1038, and 1032 using pumping unit 1044.

In a second embodiment, pumping unit 1020 is used to test flow sensors 1030, 1032, and 1038. A test is made to determine the tightness of pumping unit 1020 and pumping unit 1056. The liquid stored in the pumping unit 1020 is metered out of chamber 1022 and through flow sensors 1030, 1032, and/or 1038. It should be appreciated that in the case of flow sensor 1038, piston 1060 moves through an intake stroke to draw in solvent as piston 1024 performs a delivery stroke. The voltage of a known solvent at a known flow rate is identified, i.e., voltage 1138 is identified for flow rate 1142. An unknown solvent, such as liquid stored in reservoir 1002, is then processed through a flow sensor 1030, 1032, and/or 1038 at flow rate 1142. Voltage 1140 is the voltage of the unknown solvent at flow rate 1142. Calibration factor 1144 is then defined as a ratio of the voltage of the unknown solvent, i.e., voltage 1140, to the voltage of the known solvent, i.e., voltage 1138. This method may be performed at different flow rates. It should be appreciated that a similar method may be used to test flow sensors 1030, 1038, and 1032 using pumping unit 1056.

In a third embodiment, pumping unit 1006 and pumping unit 1020, in combination, are used to test flow sensors 1030, 1032, and 1038. A test is made to determine the tightness of pumping unit 1006 and pumping unit 1020. The liquid stored in pumping unit 1006 is metered out of chamber 1008 and through flow sensor 1018, through chamber 1022, and through flow sensors 1030, 1032, or 1038. The liquid stored in pumping unit 1020 is metered out of chamber 1022 and through flow sensors 1030, 1032, or 1038. Any combination of pumped solvent from pumping unit 1006 and 1020 is possible. It should be appreciated that in the case of flow sensor 1038, piston 1060 moves through an intake stroke to draw in solvent as piston 1024 performs a delivery stroke.

The voltage of a known solvent at a known flow rate is identified, i.e., voltage 1138 is identified for flow rate 1142. An unknown solvent, such as liquid stored in reservoir 1002, is then processed through flow sensors 1030, 1032, and/or 1038 at flow rate 1142. Voltage 1140 is the voltage of the unknown solvent at flow rate 1142. Calibration factor 1144 is then defined as a ratio of the voltage of the unknown solvent, i.e., voltage 1140, to the voltage of the known solvent, i.e., voltage 1138. This method may be performed at different flow rates. It should be appreciated that a similar method may be used to test flow sensors 1030, 1038, and 1032 using pumping unit 1044 in combination with pumping unit 1056.

Figure 10:
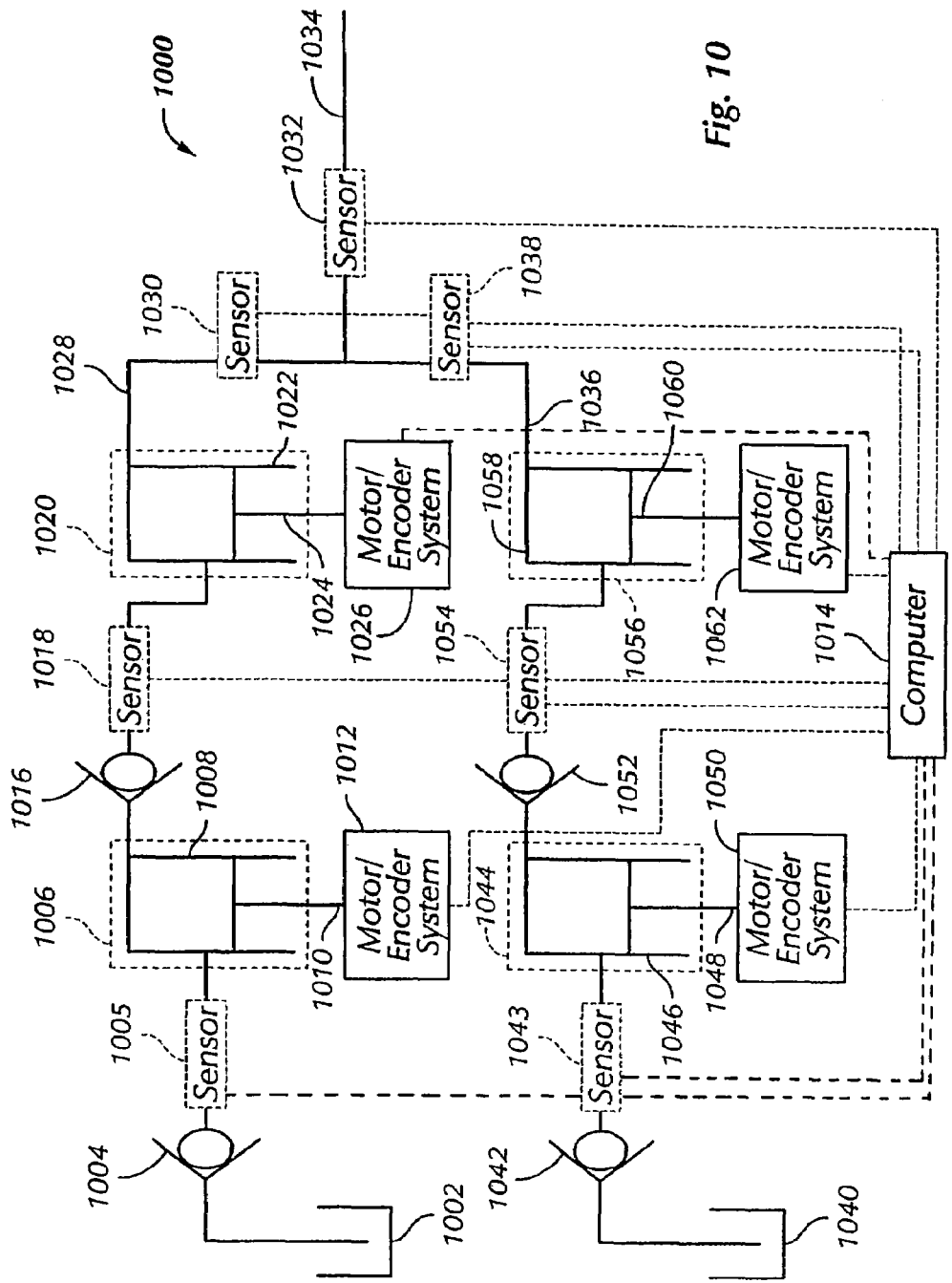
FIG. 10 is a schematic diagram of a high-pressure gradient pumping system, such as a dual-channel pumping system.
Figure 11E:
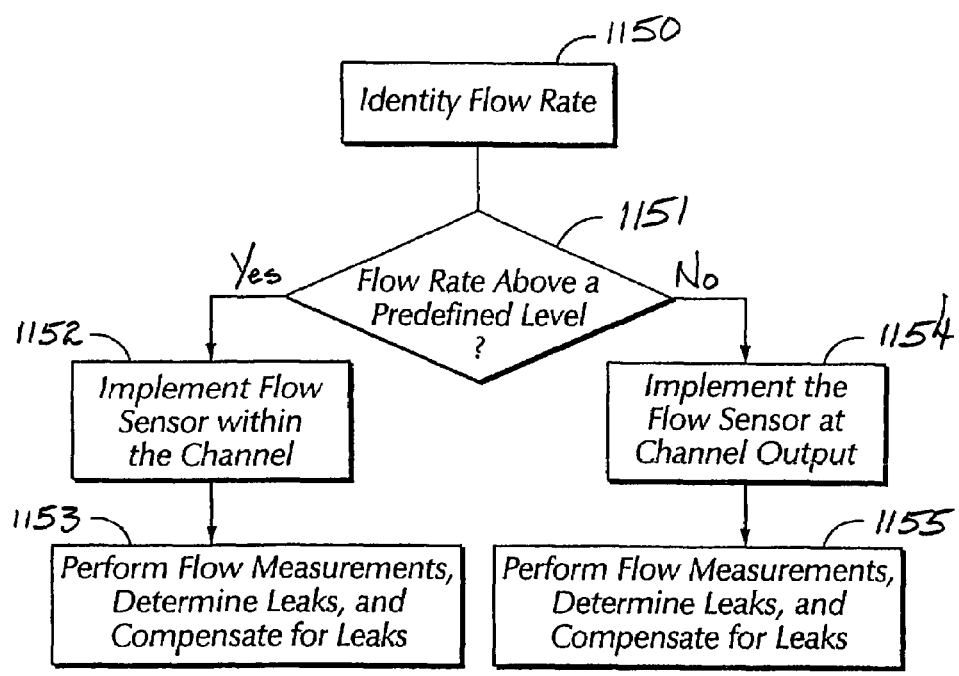
FIG. 11E is a flowchart of a method of producing a variable flow rate.

FIG. 11E is a flowchart depicting a method of producing a variable flow rate. FIG. 11E will be discussed in conjunction with FIG. 9A, 9B, and FIG. 10. In the method of producing a variable flow rate, flow sensors are positioned at various locations within a pumping system depending on the required flow rate of the pumping system. In one embodiment, the total flow rate of the pumping system is measured at low flow rates. In another embodiment, a portion of the total flow rate is measured at high flow rates. In both cases, leaks in the pumping system are identified and compensated for. For a channel having a high flow rate, the flow sensors are connected within the channel. For a channel having a low flow rate, the flow sensors are connected at the output of the channel. The method commences with step 1150.

At step 1150, a flow rate is identified. The flow rate may be identified by reading a flow sensor, or may be identified based on a metering system, or may be identified by inputting a predefined flow rate into a computer for operations. From step 1150, the method progresses to step 1151.

At step 1151, a test is performed to determine whether the flow rate is above or below a predefined level. In one embodiment, the predefined level corresponds to the maximum measuring capability of the flow sensor. If the flow rate is above the predefined level, then the method progresses to step 1152. If the flow rate is below the predefined level, then the method progresses to step 1154.

In step 1152, the flow sensor is implemented within the channel. From step 1152, the method progresses to step 1153.

In step 1153, the flow sensor is used to perform flow measurement, determine leaks, and compensate for leaks.

In step 1154, the flow sensor is implemented at the output of the channel as stated at step 1154. From step 1154, the method progresses to step 1155.

In step 1155, the flow sensor at the output of the channel is used to characterize the total flow measurement of the pumping system.

Step 1152 and 1154 each involve implementing a flow sensor. In one embodiment, implementing the flow sensor may include configuring or implementing a flow sensor into a pumping system during operations. For example, when the pumping system is operating with a low flow rate, the flow sensors at the output of the channel may be turned on and operating, and when the pumping system is operating to produce a high flow rate, the flow sensors positioned within the channel of the pumping system may be turned on and operating. It should be appreciated that the same flow sensor can be used for both positions.

The method of producing a variable flow rate presented in FIG. 11E will be discussed with respect to FIGS. 9A, 9B, and 10. In FIG. 9A, flow sensor 918 and/or flow sensor 932 may be implemented in pumping system 900 when pumping system 900 is operating to produce a high flow rate, and flow sensor 918 and/or flow sensor 942 may be implemented when the pumping system 900 is operating at a low flow rate. Further, at a high flow rate, flow sensor 918 and/or flow sensor 932 may indicate a portion of a total flow rate of the pumping system, where the total flow rate is measured at output 944. At a low flow rate, flow sensor 942 is implemented and used to operate pumping system 900. Using a method presented in the present application, leaks are detected and compensated for by metering the flow of liquid out of chamber 922, chamber 936, or chamber 922 in combination with chamber 936.

The method of producing a variable flow rate presented in FIG. 11E will be discussed with respect to FIG. 9B. In FIG. 9B, flow sensors 956, 968, 976, and 988 may be implemented when pumping system 950 is operating to produce a high flow rate, and sensors 956, 976, and 994 may be implemented when the pumping system 900 is operating to produce a low flow rate. Further, at a high flow rate, flow sensors 956, 968, 976, and 988 may indicate a portion of the total flow rate of pumping system 950, where the total flow rate is measured at channel output 996. At a low flow rate, flow sensor 994 is implemented and used to operate pumping system 950. Using a method presented in the present application, leaks are detected and compensated for by metering the flow of liquid out of chamber 960, chamber 980, or chamber 960 in combination with chamber 980.

In FIG. 10, flow sensors 1005, 1018, 1043, and/or 1054 may be implemented in pumping system 1000 to measure a high flow rate, and flow sensors 1030, 1032, and 1038 may be implemented when pumping system 1000 is operating to measure a low flow rate. Further, at a high flow rate, flow sensors 1018 and 1054 may represent a portion of the total flow rate of pumping system 1000, where the total flow rate is the flow rate of liquid at output 1034. At a low flow rate, flow sensors 1030, 1032, and/or 1038 are implemented and used to operate pumping system 1000. Using methods presented in the instant application, leaks are detected and compensated for by metering the flow of liquid out of chamber 1008, chamber 1022, chamber 1046, chamber 1058, or any combination of chambers 1008, 1022, 1046, and/or 1058.

Figure 12:
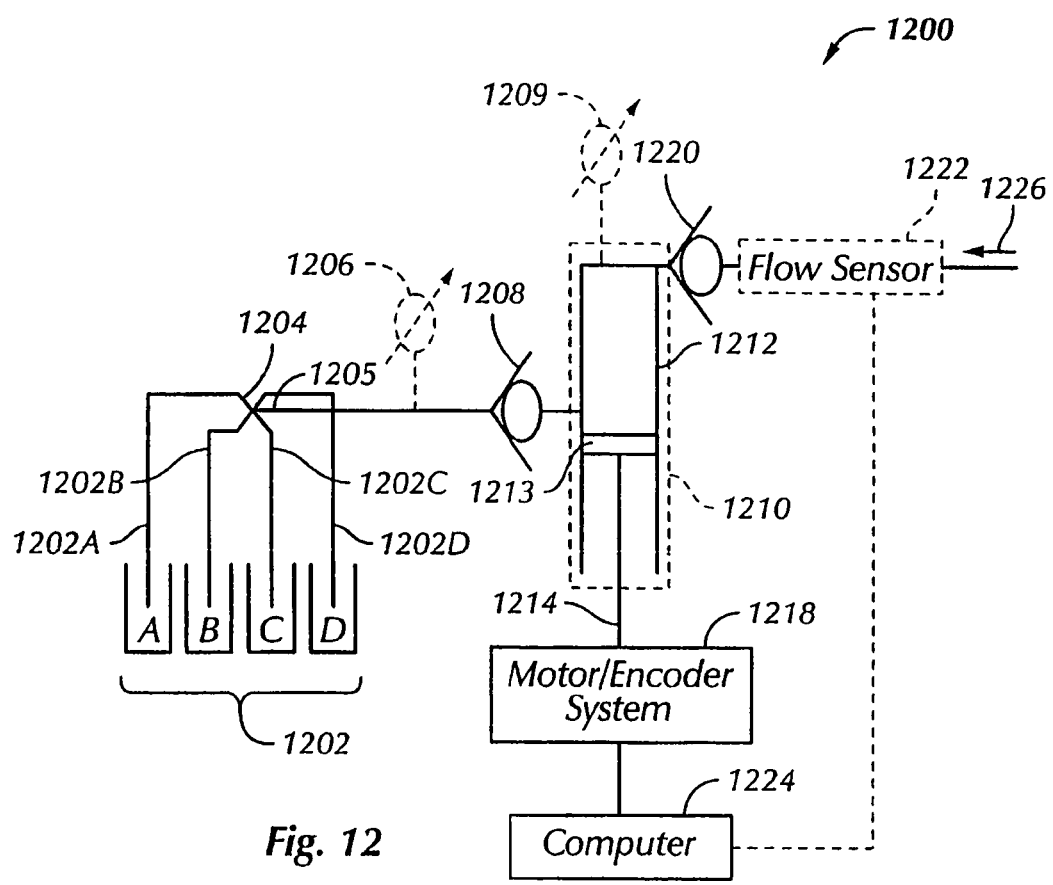
FIG. 12 is a schematic of a pumping unit including a flow sensor and a pressure sensor(s).

FIG. 12 is a schematic of a pumping system that includes pressure sensors. A pumping system 1200 includes a variety of liquids A, B, C, and D. Liquids A, B, C, and D are stored in a reservoir 1202. Each liquid A, B, C and D is conveyed on a conveyance 1202A, 1202B, 1202C, and 1202D, respectively. Liquids A, B, C and D are mixed using a proportioning valve 1204. The liquid (i.e., A, B, C, D) is drawn through an inlet valve 1208 via a conveyance 1205. A pressure sensor 1206 is positioned on conveyance 1205 to sense the pressure between proportioning valve 1204 and inlet valve 1208. A pumping unit 1210 is positioned in series with inlet valve 1208. Pumping unit 1210 includes a chamber 1212, a piston 1214, and a seal 1213. On an intake stroke of piston 1214, liquid fills chamber 1212, and on a delivery stroke of piston 1214, liquid is compressed and forced out of chamber 1212, through an outlet valve 1220. A pressure sensor 1209 is positioned to measure the pressure in the chamber 1212.

A motor/encoder system 1218 and a computer 1224 are used to adjust the intake stroke and the delivery stroke of piston 1214, which meters the flow of liquid through chamber 1212 by adjusting the intake and expulsion of liquid from the chamber 1212. A flow sensor 1222 is positioned in series with outlet valve 1220. Flow sensor 1222 is capable of measuring the flow of liquid out of pumping unit 1210. Flow sensor 1222 reports the measured flow to computer 1224.

A variety of methods for determining and compensating for leaks are presented and implemented with pumping system 1200. In one embodiment, a method of determining leaks in an inlet valve is presented. In a second embodiment, a method of detecting leaks in an outlet valve is presented. In a third embodiment, a method of determining leaks in a seal/piston combination is presented. In a fourth embodiment, a method of determining leaks in a gradient valve is presented.

Figure 12A:
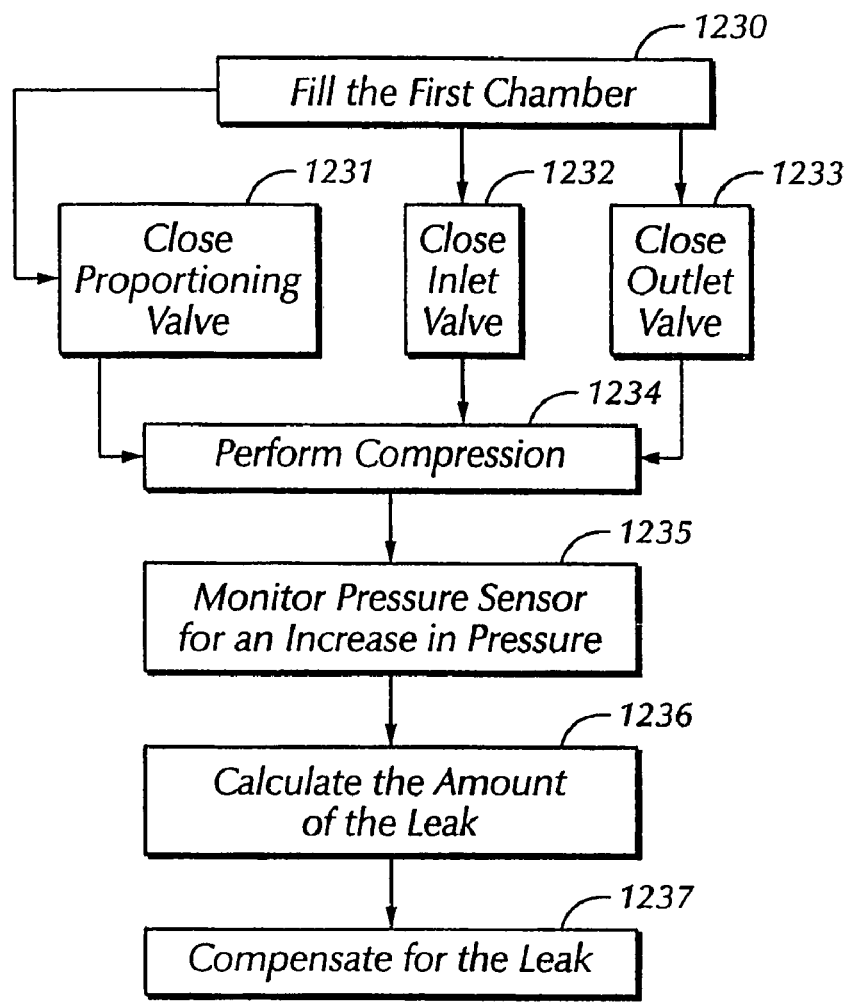
FIG. 12A is a flowchart of a method of identifying and compensating for leaks using a pressure sensor.

FIG. 12A is a flowchart of a method of identifying and compensating for leaks using pressure sensors. FIG. 12A will be discussed in conjunction with FIG. 12. The method commences with step 1230.

At step 1230, a chamber is filled with liquid. For example, chamber 1212 is filled with liquid. To fill chamber 1212 with liquid, outlet valve 1220 is closed, proportioning valve 1204 is opened, and inlet valve 1208 is opened. Liquid is drawn into chamber 1212 as piston 1214 performs an intake stroke. After step 1230, the method progresses to perform each of steps 1231, 1232 and 1233, generally, in parallel with one another.

In step 1231, proportioning valve 1204 is closed. From step 1231 (after the completion of steps 1232 and 1233), the method progresses to step 1234.

In step 1232, inlet valve 1208 is closed. From step 1232 (after the completion of steps 1231 and 1233), the method progresses to step 1234.

In step 1233, outlet valve 1220 is closed. From step 1233 (after the completion of steps 1231 and 1232), the method progresses to step 1234.

In step 1234, with each of proportioning valve 1204, inlet valve 1208, and outlet valve 1220 being closed, compression is performed. During compression, piston 1214 moves upward (i.e., delivery stroke) to compress the liquid in the chamber 1212. Compressing liquid in chamber 1212 increases the pressure in chamber 1212. From step 1234, the method progresses to step 1235.

In step 1235, after pumping system 1200 reaches steady state (i.e., all the components have settled), the pressure is measured. Pressure sensor 1206 is monitored for a change in pressure. If an increase in pressure is determined, the increase in pressure signals a flow of liquid back through inlet valve 1208 as a result of a leak in inlet valve 1208. From step 1235, the method progresses to step 1236.

In step 1236, based on the amount of pressure increase in pressure sensor 1206, the amount of the leak in inlet valve 1208 is calculated. In one embodiment of the present invention, the amount of leak in inlet valve 1206 is calculated using the volume between proportioning valve 1204 and inlet valve 1206, the compressibility factor of the liquid and the pressure increase. From step 1236, the method progresses to step 1237.

In step 1237, once the amount of the leak has been determined, adjustments are made in pumping system 1200 to compensate for the leak. For example, using piston 1214, motor/encoder system 1218, and computer 1224, metering may be performed to compensate for the leak.

Figure 12B:
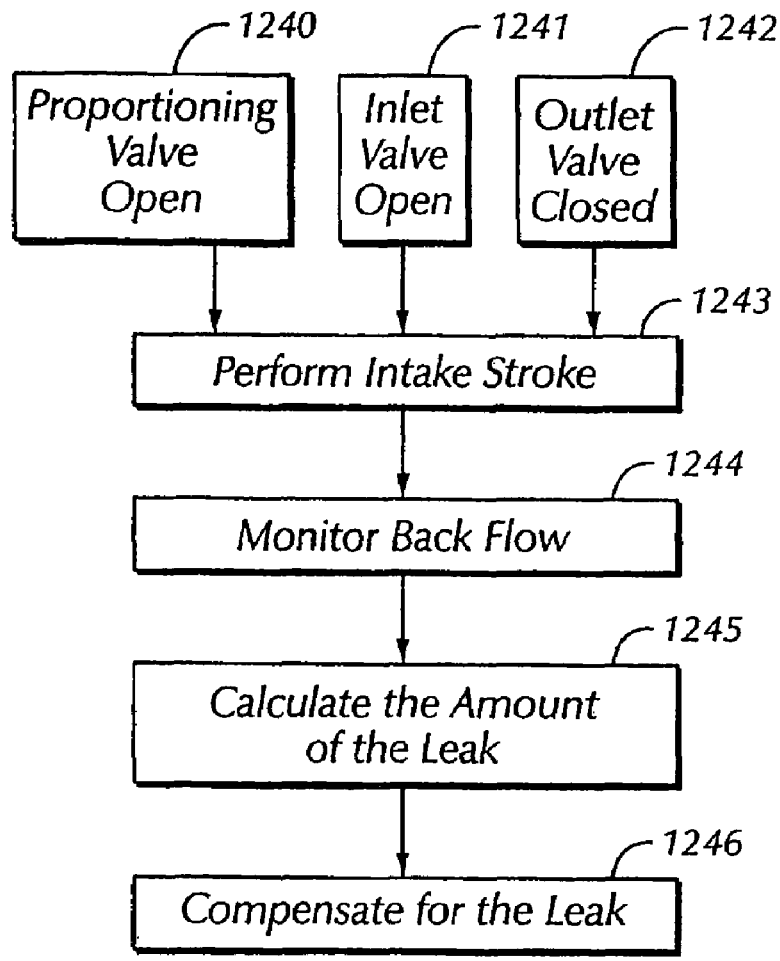
FIG. 12B is a flowchart of a method of identifying and compensating for leaks using a flow sensor.

FIG. 12B is a flowchart of a method of identifying and compensating for leaks using flow sensors. The method commences with steps 1240, 1241 and 1242 being performed, generally, in parallel with one another.

In step 1240, a proportioning valve is opened. From step 1240 (after the completion of steps 1241 and 1242), the method progresses to step 1243.

In step 1241, an inlet valve is opened. From step 1241 (after the completion of steps 1240 and 1242), the method progresses to step 1243.

In step 1242, an outlet valve is closed. From step 1242 (after the completion of steps 1240 and 1241), the method progresses to step 1243.

In step 1243, a first piston in a first pumping unit performs an intake stroke. It should be appreciated that in a second embodiment, the method depicted in FIG. 12B may be performed without performing the intake stroke as stated at step 1243. Opening the proportioning valve as stated at step 1240, opening the inlet valve as stated at step 1241, and closing the outlet valve as stated at step 1242 will result in a backflow of liquid provided that the pressure after the outlet valve is higher than the pressure within the chamber. From step 1243, the method progresses to step 1244.

In step 1244, a flow sensor is used to monitor the backflow. From step 1244, the method progresses to step 1245.

In step 1245, the backflow is used to calculate the amount of a leak. From step 1245, the method progresses to step 1246.

In step 1246, leaks are compensated for, for example, by metering, e.g., with a second piston.

The method depicted in the flow diagram of FIG. 12B will now be discussed with respect to the pumping system depicted in FIG. 12. The method commences with steps 1240, 1241 and 1242 being performed, generally, in parallel with one another.

At steps 1240, 1241, and 1242, proportioning valve 1204 is opened, inlet valve 1208 is opened, and outlet valve 1220 is closed. After the completion of steps 1240, 1241, and 1242, the method progresses to step 1243.

At step 1243, piston 1214 performs an intake stroke. From step 1243, the method progresses to step 1244.

At step 1244, flow sensor 1222 is monitored to detect a backflow 1226. If backflow 1226 is detected by flow sensor 1222, there is a leak in outlet valve 1220. From step 1244, the method progresses to step 1245.

In step 1245, once the leak has been determined, the amount of liquid flowing through flow sensor 1222 may be used to calculate the amount of the leak. In one embodiment, it should be appreciated that the flow sensor is measuring the amount of the leak directly. If a leak occurs, the new-metered flow rate with a piston after the flow sensor (not shown in FIG. 12) is equivalent to the metered flow, which is equal to the nominal flow plus the leak. From step 1245, the method progresses to step 1246.

In step 1246, once the amount of the leak is calculated, metering may be performed to compensate for the leak. Metering may include operating, e.g., a second piston of a serial pumping system, a motor/encoder unit responsible for moving that second pumping piston, and a corresponding computer (not shown in FIG. 12) to compensate for the amount of the leak.

Figure 12C:
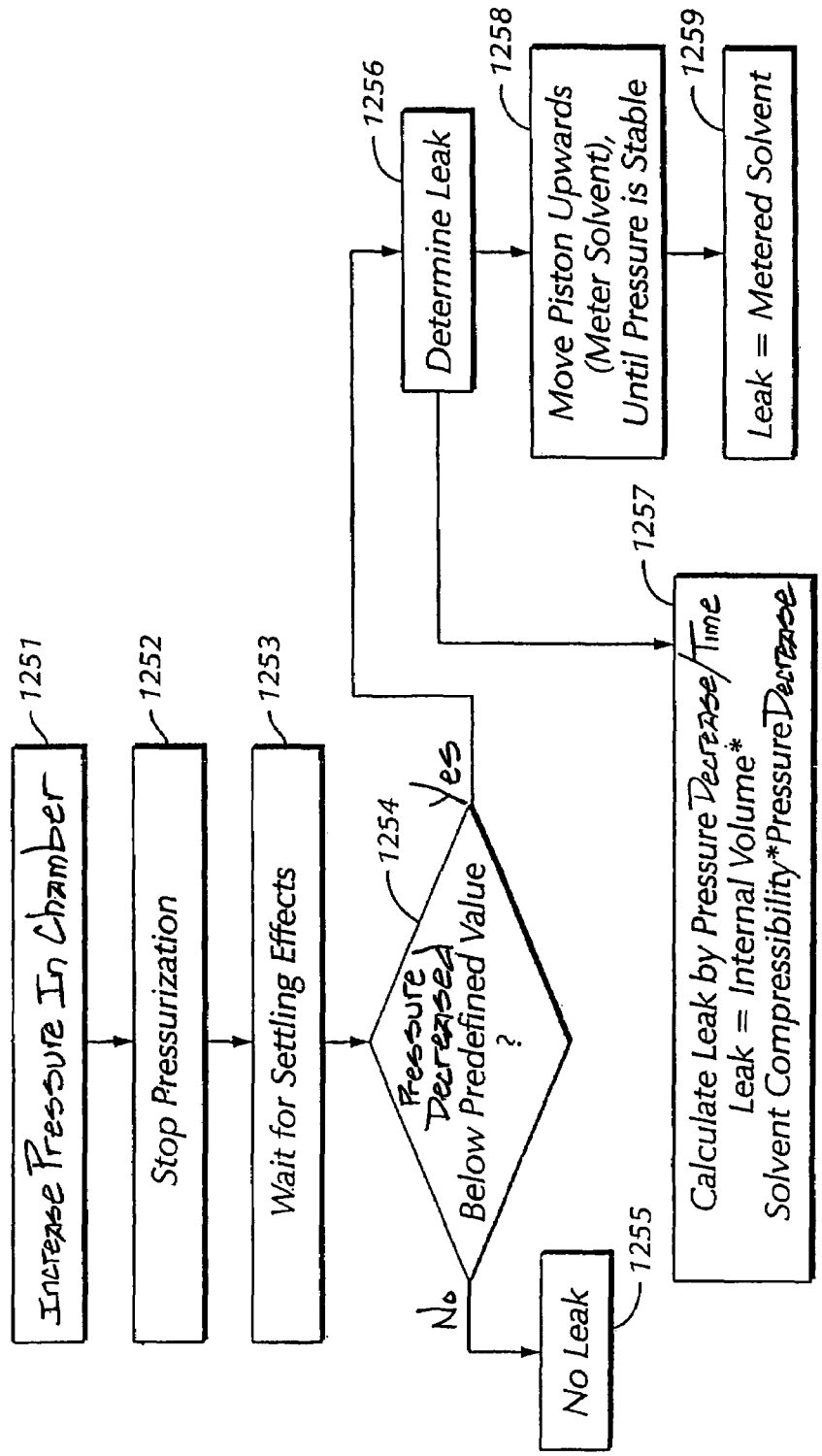
FIG. 12C is a flowchart of a method of identifying and compensating for leaks using a pressure sensor.

FIG. 12C is a flowchart of a method of detecting a leak in a chamber, such as chamber 1212 of FIG. 12. FIG. 12C will be discussed in conjunction with FIG. 12. The method depicted in the flowchart of FIG. 12C may be used to detect leaks in a piston/seal 1214/1213 combination, the leak in an inlet valve 1208, the leak in an outlet valve 1220, a leaky fitting, etc. The method commences with step 1251.

At step 1251, pressure in chamber 1212 is increased to a level above atmospheric pressure. In one embodiment, piston 1214 is moved through a portion of a delivery stroke to pressurize liquid in chamber 1212. From step 1251, the method progresses to step 1252.

At step 1252, stopping the movement of piston 1214 stops the pressurization. From step 1252, the method progresses to step 1253.

At step 1253, time is allotted to wait for the settling effects and pressure is monitored over a period of time. For example, time is allotted to wait for the settling effects of pumping unit 1210. After settling is completed, pressure sensor 1209 is used to monitor the pressure in chamber 1212 over a period of time. Since, in step 1251 pressure in chamber 1212 was increased to a level above atmospheric pressure, if the pressure decreases during step 1253, such a decrease would be indicative of a leak. From step 1253, the method progresses to step 1254.

At step 1254, a determination is made as to whether the pressure has decreased to a value below a predefined value. If the pressure has not decreased to a value below the predefined value, then there is no leak, and the method progresses to step 1255. If the pressure has decreased to a value below the predefined value, then there is a leak, and the method progresses to step 1256.

In step 1255, since the pressure has not decreased to a value below the predetermined value, there is no leak.

At step 1254, since the pressure has decreased to a value below the predefined value, there is a leak. The leak may be determined using two methods. Accordingly, from step 1254, the method progresses to either of step 1257 or step 1258.

In step 1257, a leak is determined by a pressure decrease over time. As a result, the leak equals the internal volume times solvent compressibility times the pressure decrease, where the internal volume is the volume of the liquid in chamber 1212, the solvent compressibility is the compression of liquid in chamber 1212, and the pressure decrease is given by a change in the pressure reading on pressure sensor 1209.

In step 1258, the leak is determined by moving piston 1214 upward until the pressure is stable. Using FIG. 12, this would include moving piston 1214 upward through a portion of a delivery stroke until the pressure registered by pressure sensor 1209 is stable. During the partial delivery stroke, the metered liquid or solvent may be determined using motor/encoder system 1218 and computer 1224. From step 1258, the method progresses to step 1259.

In step 1259, the leak will then equal the metered solvent.

Figure 12D:
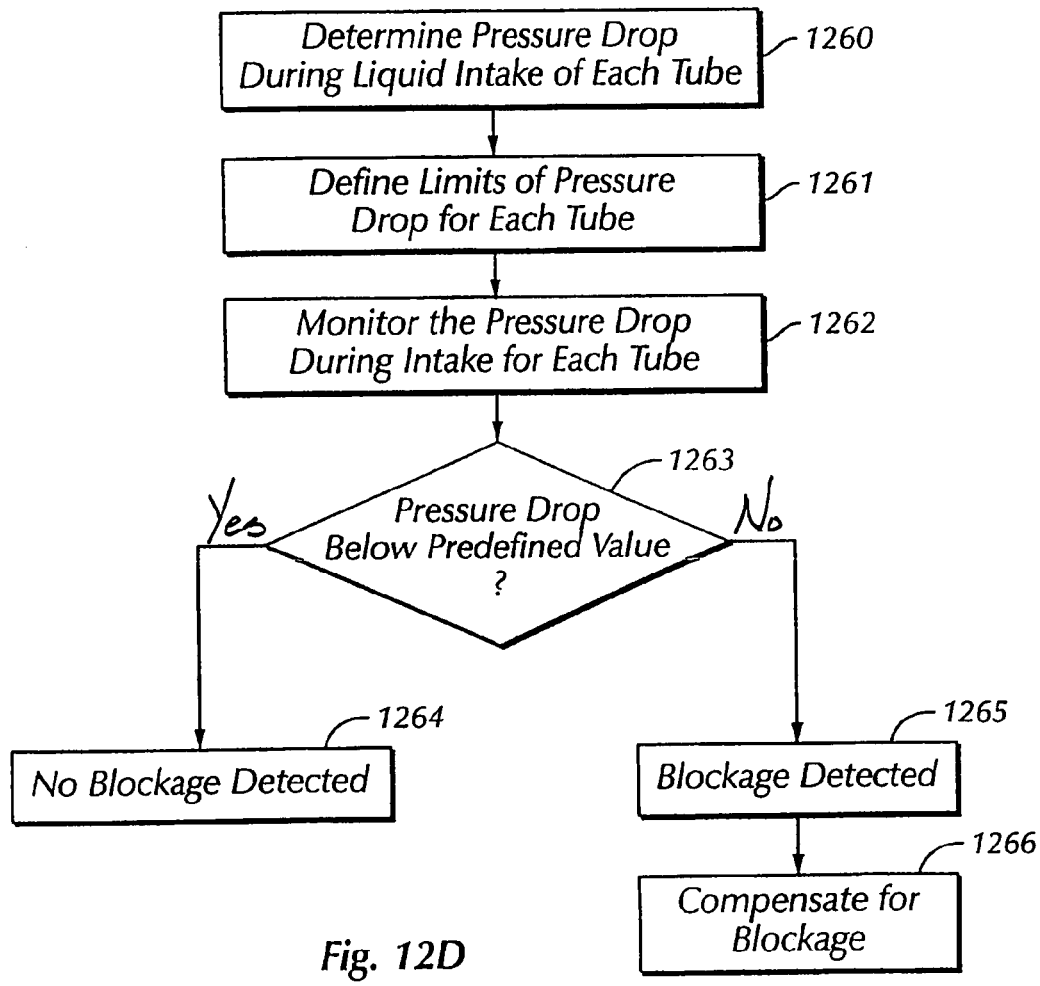
FIG. 12D is a flowchart of a method of identifying a blocked inlet tube.

FIG. 12D is a flowchart of a method of detecting a blocked conveyance (i.e., a blocked filter at a conveyance inlet). FIG. 12D will be discussed in conjunction with FIG. 12. The method commences with step 1260.

At step 1260, a pressure drop across each conveyance 1202A, 1202B, 1202C and 1202D is determined during an intake of liquid through each conveyance 1202A, 1202B, 1202C and 1202D. From step 1260, the method progresses to step 1261.

At step 1261, the limits of the pressure drop are defined for each conveyance. The pressure drop for the individual channels 1202A, 1202B, 1202C and 1202D can be defined individually. From step 1261, the method progresses to step 1262.

At step 1262, the pressure drop is monitored as liquid is conveyed through each conveyance 1202A, 1202B, 1202C and 1202D. From step 1262, the method progresses to step 1263.

In step 1263, the method determines whether the pressure drop across each conveyance 1202A, 1202B, 1202C and 1202D is below a predefined value. If the pressure drop across each conveyance 1202A, 1202B, 1202C and 1202D is below the predefined value, then there is no blockage, and the method progresses to step 1264. If the pressure drop across each conveyance 1202A, 1202B, 1202C and 1202D is not below the predefined value, that is the pressure is greater than the predefined value for one or more of conveyances 1202A, 1202B, 1202C or 1202D, then the method progresses to step 1265.

In step 1264, since the pressure drop across each conveyance 1202A, 1202B, 1202C and 1202D is below the predefined level, no blockage is detected.

In step 1265, since the pressure drop across each conveyance 1202A, 1202B, 1202C and 1202D is not below the predefined level, that is the pressure is greater than the predefined value for one or more of conveyances 1202A, 1202B, 1202C or 1202D, blockage is detected. From step 1265, the method progresses to step 1266.

In step 1266, in one embodiment, an adjustment is made to compensate for the blockage. For example, in the case of a partial blockage, the intake stroke of piston 1214 may be adjusted to draw in liquid with lower speed to compensate for the blockage (e.g., avoid generation of gas bubbles).

The flowchart of FIG. 12D will be discussed in conjunction with pumping system 1200 depicted in FIG. 12. In FIG. 12, pressure sensor 1206 may be used to calibrate the inlet pressure for conveyances 1202A, 1202B, 1202C, and 1202D. To calibrate the inlet pressure for each conveyance 1202A, 1202B, 1202C, and 1202D, as inlet valve 1208 is opened and piston 1214 intakes liquid (i.e., A, B, C, D), pressure is measured as the liquid (i.e., A, B, C, D) is conveyed past pressure sensor 1206. For example, when liquid A flows through conveyance 1202A, via conveyance 1205, to inlet valve 1208, the pressure is measured. When liquid B flows through conveyance 1202B, via conveyance 1205, to inlet valve 1208, the pressure is measured. When liquid C flows through conveyance 1202C, via conveyance 1205, to inlet valve 1208, the pressure is measured. When liquid D flows through conveyance 1202D, via conveyance 1205, to inlet valve 1208, the pressure is measured.

In step 1260, using the aforementioned techniques, a pressure drop across each conveyance 1202A, 1202B, 1202C and 1202D is determined. From step 1260, the method progresses to step 1261.

In step 1261, the limits of the pressure drop are defined. From step 1261, the method progresses to step 1262.

At step 1262, the pressure drop across each conveyance 1202A, 1202B, 1202C and 1202D is monitored during the intake phase of the solvent using pressure sensor 1206. From step 1262, the method progresses to step 1263.

In step 1263, during operation, a test is made to determine if the pressure drop across each conveyance 1202A, 1202B, 1202C and 1202D is below a predefined value (i.e., level). If the pressure drop across each conveyance 1202A, 1202B, 1202C and 1202D is below the predefined value (i.e., Yes), then the method progresses to step 1264. If the pressure drop across at least one conveyance 1202A, 1202B, 1202C or 1202D is not below the predefined value (i.e., No), then the method progresses to step 1265.

In step 1264, since the pressure drop is below the predefined level, no blockage is detected.

In step 1265, since the pressure drop is not below the predefined level, blockage is detected. In one embodiment, the blockage may occur in conveyances 1202A, 1202B, 1202C and/or 1202D. From step 1265, the method progresses to step 1266.

In step 1266, once blockage has been detected, activities may be performed to compensate for a partial blockage. For example, piston 1214 may perform an adjusted intake stroke to ensure the correct volume of liquid is brought in across the conveyance. For example, in one embodiment, the intake stroke speed is reduced to avoid the generation of gas bubbles.

In one embodiment of detecting a leak in a proportioning valve, an on/off valve, such as a proportioning valve 1204, is closed. If more channels or conveyances are connected (e.g., for liquids A, B, C, D), all the channels or conveyance are closed. A piston, such as piston 1214, is moved to intake liquid into chamber 1212. Pressure is measured. For example, pressure sensor 1206 may measure the pressure on conveyance 1205. In one embodiment, when performing an intake stroke with piston 1214 (i.e., inlet valve 1208 opened, and outlet valve 1220 closed), the pressure on conveyance 1205 decreases to a level below atmospheric pressure. Piston 1214 stops and the pressure is monitored. After waiting a time for settling effects, the pressure is constant. In the case of a leak in proportioning valve 1204, the pressure will increase to atmospheric pressure. It should be appreciated that the pumping unit must be tested for tightness before the test described above is performed.

In another embodiment, the tightness of the proportioning valve is tested. First, the pumping unit (i.e., piston/chamber) is tested for tightness as described above. Afterwards, all of the channels (i.e., each conveyance) of the proportioning valve are closed, the inlet valve is opened and the outlet valve is closed. The piston moves upward to increase the pressure in conveyance 1205 to a level above atmospheric pressure. The piston stops, waiting a time for settling effects and monitoring the pressure. If proportioning valve 1204 is tight, the pressure is constant and remains above a predefined level. If leaky, the pressure decreases to atmospheric pressure over time.

In both embodiments presented above, the amount of leak is calculated by the volume of liquid between proportioning valve 1204 and inlet valve 1208, the compressibility factor of the liquid, and the pressure change over time. For example, in one embodiment, the leak is equal to the volume times the compressibility of liquid times the pressure change.

In another embodiment, chamber 1212 is checked for tightness using a pressure sensor 1206 on a conveyance, such as conveyance 1205. Inlet valve 1208 is opened, outlet valve 1220 is closed, proportioning valve 1204 is closed completely (all channels), and conveyance 1205 is pressurized by moving piston 1214 upwards. The pressure is monitored. A pressure level is predefined. Adapting the speed of piston 1214 to keep the pressure constant controls the pressure. The pumped liquid required to keep that pressure constant on conveyance 1205 is equivalent to the amount of the leak.

Figure 12E:
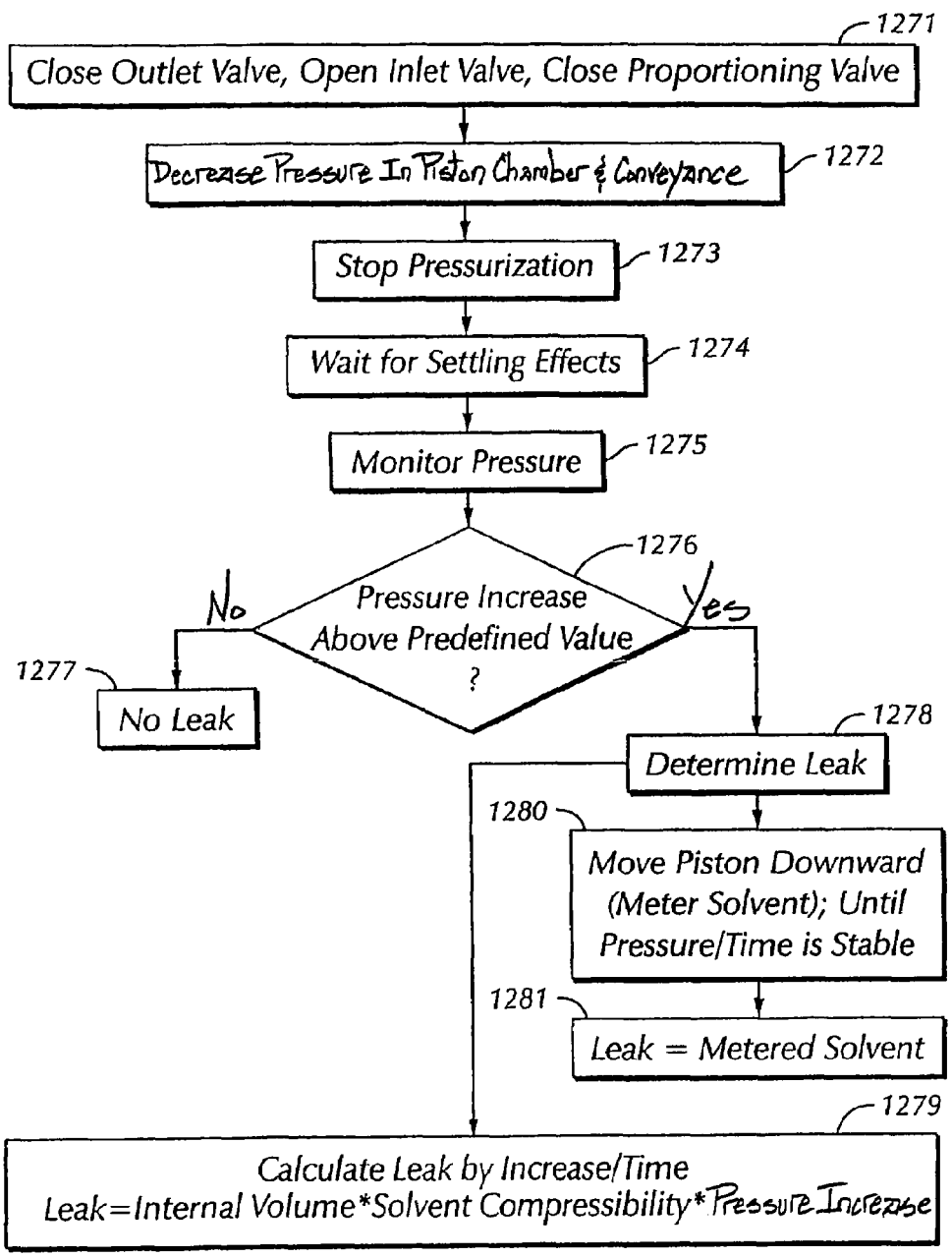
FIG. 12E is a flowchart of a method of identifying and compensating for leaks using a pressure sensor.

FIG. 12E is a flowchart of a method of detecting a leak in a piston chamber including an adapted valve such as an outlet valve or a proportioning valve. FIG. 12E will be discussed in conjunction with FIG. 12. The method depicted in FIG. 12E commences with step 1271.

At step 1271, an outlet valve, such as outlet valve 1220, is closed; an inlet valve, such as inlet valve 1208, is opened; and a valve, such as proportioning valve 1204, is closed. From step 1271, the method progresses to step 1272.

At step 1272, pressure in chamber 1212 is decreased. In one embodiment, decreasing the pressure in chamber 1212 includes moving piston 1214 downward through a partial intake stroke. When piston 1214 moves downward through the partial intake stroke, the pressure on conveyance 1205 decreases to a level below atmospheric pressure.

At step 1273, the piston 1214 is stopped to discontinue the decrease in pressure on the conveyance 1205.

At step 1274, time is allowed to wait for settling effects.

At step 1275, the pressure is monitored on conveyance 1205 using pressure sensor 1206. Since, in step 1272 pressure in chamber 1212 was decreased to a level below atmospheric pressure, if the pressure increases during step 1275, such an increase would be indicative of a leak.

At step 1276, a test is made to determine if the pressure has increased above a predefined value. If the pressure has not increased above the predefined value, then there is no leak, and the method progresses to step 1278. If the pressure has increased above the predefined value, i.e., toward atmospheric pressure, then there is a leak, and the method progresses to step 1278.

In step 1277, since the pressure has not increased above the predefined value, there is no leak.

In step 1278, since the pressure has increased above the predefined value, i.e., toward atmospheric pressure, then a leak in the piston chamber or in an adapted valve such as an outlet valve or a proportioning valve may be determined. The leak may be determined in two ways. Accordingly, from step 1278, the method may progress to either of step 1279 or step 1280.

In step 1279, the leak is calculated by the increase in pressure over time. In this case, the calculated leak equals the internal volume times the solvent compressibility times the pressure increase.

In step 1280, the leak is determined by moving piston 1214 downward until the pressure measured by pressure sensor 1206 is stable. From step 1280, the method progresses to step 1281.

In step 1281, motor/encoder system 1218 and computer 1224 are then used to determine the metered solvent from the downward movement of piston 1214, and the leak is equal to the metered solvent.

Figure 12F:
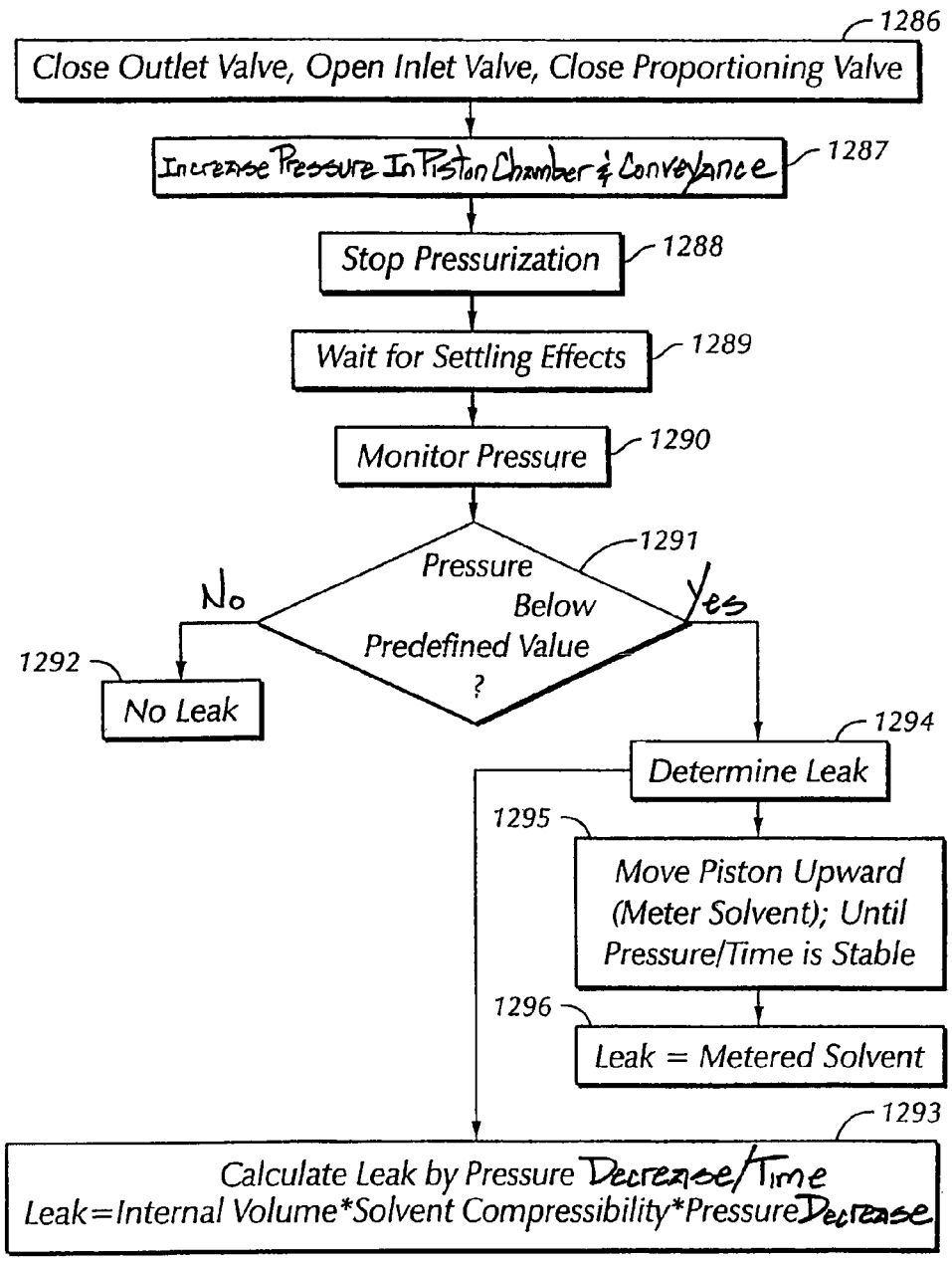
FIG. 12F is a flowchart of a method of detecting a leak in a proportioning valve.

FIG. 12F is a flowchart of a method of testing for a leak in the piston chamber or an adapted valve such as an outlet valve or a proportioning valve. FIG. 12F will be discussed in conjunction with FIG. 12. The method depicted in FIG. 12F commences with step 1286.

At step 1286, an outlet valve, such as outlet valve 1220, is closed; an inlet valve, such as inlet valve 1208, is opened; and a proportioning valve, such as proportioning valve 1204, is closed. From step 1286, the method progresses to step 1287.

At step 1287, pressure in chamber 1212 is increased to a level greater than atmospheric pressure. In addition, since inlet valve 1208 is opened, conveyance 1205 is also pressurized. In one embodiment, increasing pressure in chamber 1212 includes moving piston 1214 upward through a partial delivery stroke. When piston 1214 moves upward through the partial intake stroke, the pressure on conveyance 1205 is increased to a level above atmospheric pressure. From step 1287, the method progresses to step 1288.

At step 1288, piston 1214 is stopped to stop the pressurization of chamber 1212 and conveyance 1205. From step 1288, the method progresses to step 1289.

At step 1289, time is allowed to wait for settling effects. From step 1289, the method progresses to step 1290.

At step 1290, the pressure is monitored on conveyance 1205 using pressure sensor 1206. Since, in step 1287 pressure in chamber 1212 was increased to a level above atmospheric pressure, if the pressure decreases during step 1290, such a decrease would be indicative of a leak. From step 1290, the method progresses to step 1291.

At step 1291, a test is made to determine whether the pressure has decreased to a value below a predefined value. If the pressure has not decreased to a value below the predefined value, then there is no leak, and the method progresses to step 1292. If the pressure has decreased to a value below the predefined value, then there is a leak, and the method progresses to step 1294.

In step 1292, since the pressure has not decreased to a value below the predefined value, there is no leak.

In step 1294, since the pressure has decreased to a value below the predefined value, there is a leak. The leak may be determined in two ways.

Accordingly, from step 1294, the method may progress to either of step 1293 of step 1295.

In step 1293, the leak is calculated by the decrease in pressure over time. In this case, the calculated leak equals the internal volume times the solvent compressibility times the pressure decrease.

In step 1295, the leak is determined by moving piston 1214 upward until the pressure measured by pressure sensor 1206 is stable. From step 1295, the method progresses to step 1296.

In step 1296, motor/encoder system 1218 and computer 1224 are then used to determine the metered solvent from the upward movement of piston 1214, and the leak equals the metered solvent.

Figure 13:
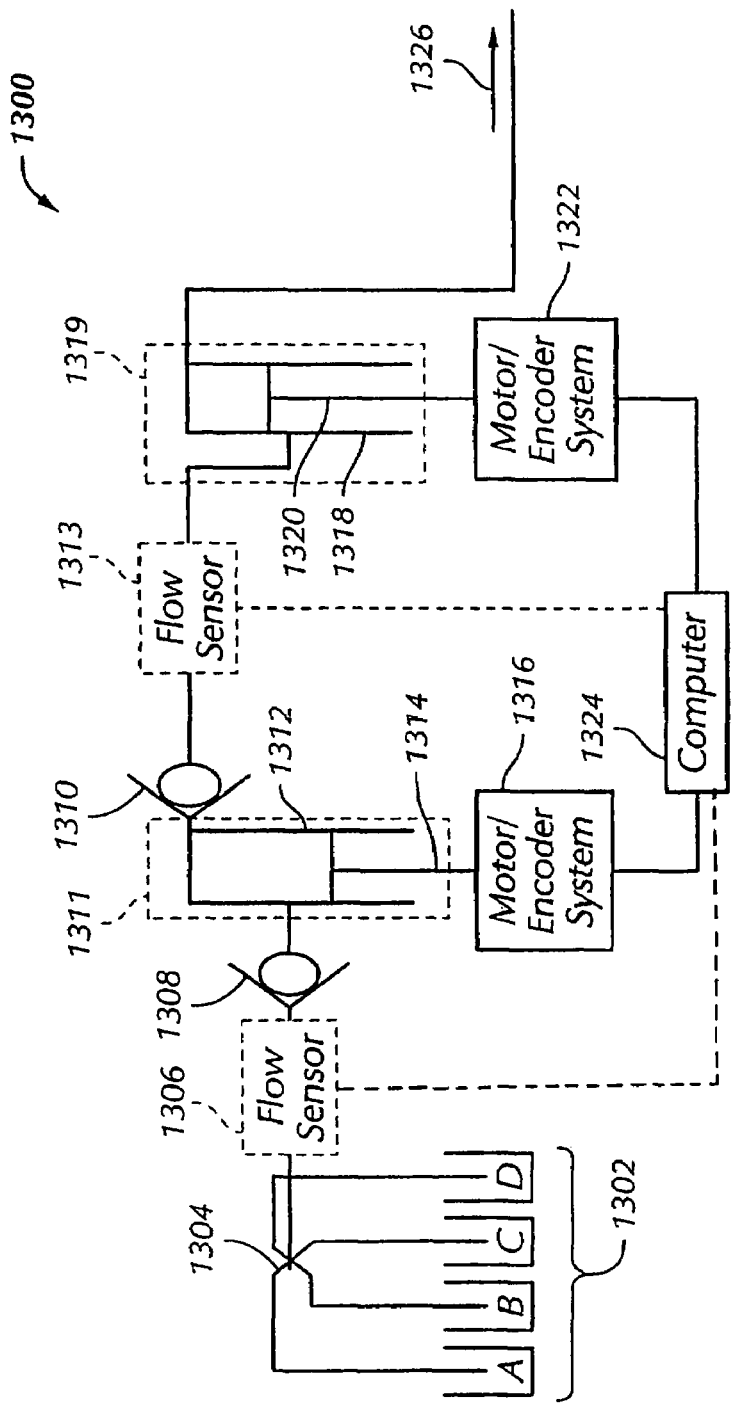
FIG. 13 is a schematic diagram of a single-channel pumping system including flow sensors.

FIG. 13 is a schematic diagram of a single-channel pumping system, i.e., a pumping system 1300, including flow sensors. Pumping system 1300 includes a reservoir 1302 storing a variety of liquids as shown by liquids A, B, C, and D. A switch, such as a proportioning valve 1304, is connected in series with a flow sensor 1306. Flow sensor 1306 is connected in series with an inlet valve 1308. Inlet valve 1308 is in series with a pumping unit 1311. Pumping unit 1311 includes a chamber 1312 and a piston 1314. Pumping unit 1311 is further in series with a pumping unit 1319 that includes a piston 1320 and a chamber 1318. In one embodiment, a flow sensor 1313 is positioned between pumping unit 1311 and pumping unit 1319. Pumping unit 1311 is connected to a motor/encoder system 1316, and pumping unit 1319 is connected and controlled by a motor/encoder system 1322. Both of motor/encoder system 1316 and motor/encoder system 1322 are connected to, and controlled by, a computer 1324.

The liquids (i.e., A, B, C, D) are mixed in proportioning valve 1304 and conveyed through flow sensor 1306 to inlet valve 1308. On the intake stroke of piston 1314, liquid (i.e., A, B, C, D) fills chamber 1312, and on the delivery stroke of piston 1314, liquid (i.e., A, B, C, D) is compressed and forced out of chamber 1312, through outlet valve 1310. Motor/encoder system 1316 and computer 1324 are used to meter the flow of liquid (i.e., A, B, C, D) through pumping unit 1311 by adjusting the upward and intake stroke of piston 1314 to adjust the intake and expulsion of liquid (i.e., A, B, C, D) from chamber 1312. Outlet valve 1310 is positioned to allow liquid (i.e., A, B, C, D) to flow between pumping unit 1311 and pumping unit 1319. Liquid (i.e., A, B, C, D) is received from chamber 1312 into chamber 1318. The flow of liquid (i.e., A, B, C, D) between pumping unit 1311 and pumping unit 1319 is measured by flow sensor 1313. Liquid (i.e., A, B, C, D) fills chamber 1318, and on the delivery stroke of piston 1320, liquid (i.e., A, B, C, D) is forced out of chamber 1318. Motor/encoder system 1322 and computer 1324 are used to adjust the upward and intake stroke of piston 1320 to adjust the intake and expulsion of liquid (i.e., A, B, C, D) from chamber 1318. Lastly, liquid (i.e., A, B, C, D) is delivered, as represented by arrow 1326, to the remainder of the chromatography system (not shown in FIG. 13).

Figures 13A, 13B:
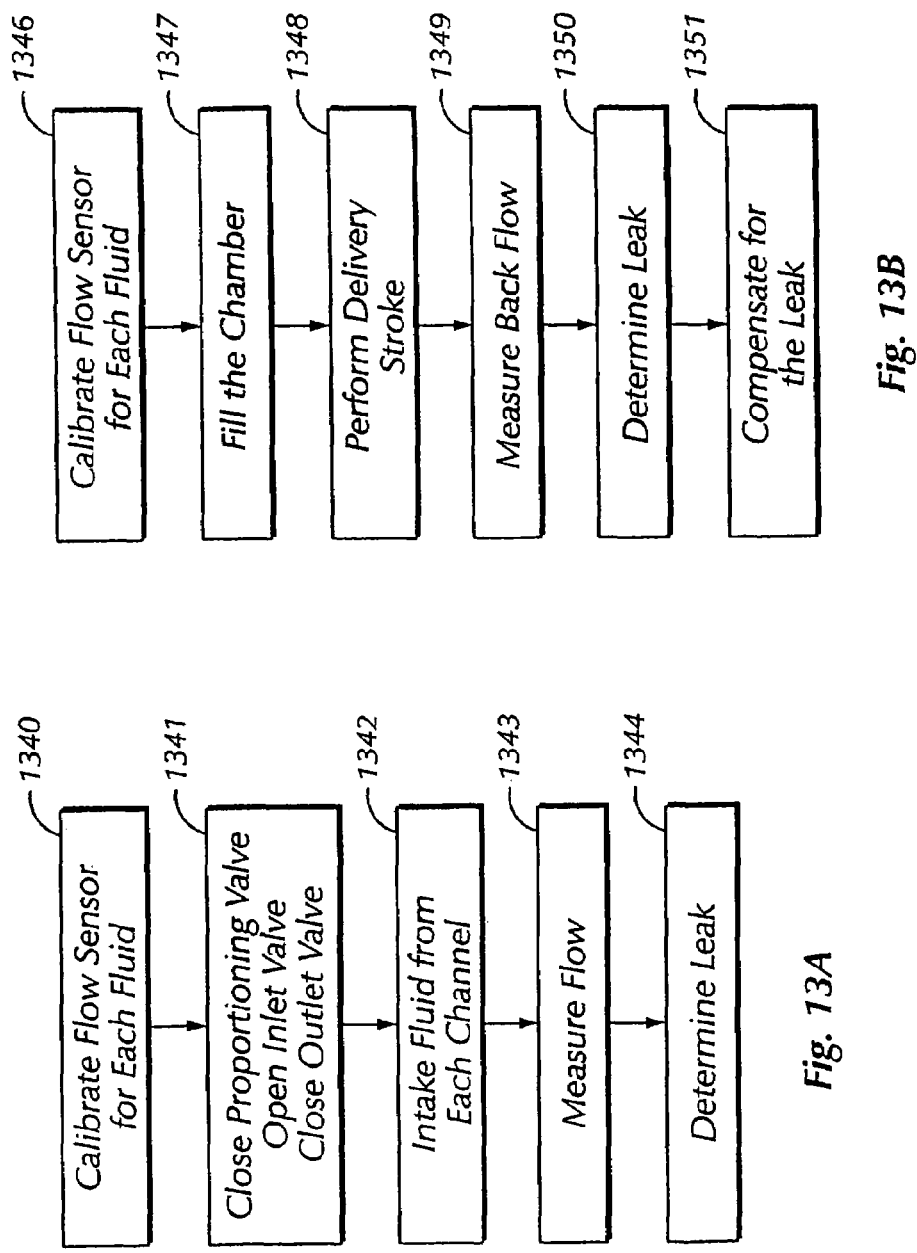
FIG. 13A is a flowchart of a method of detecting a leak in a gradient valve.
FIG. 13B is a flowchart of a method of detecting a leak in an inlet valve.

FIG. 13A is a flowchart of a method of detecting a leak in a gradient valve. FIG. 13A will be discussed in conjunction with FIG. 13. The method depicted in FIG. 13A commences with step 1340.

At step 1340, a flow sensor positioned between proportioning valve 1304 and inlet valve 1308 is calibrated for each liquid (i.e., A, B, C, D) stored in reservoir 1302. For example, flow sensor 1306 is calibrated for each liquid (i.e., A, B, C, D) stored in reservoir 1302.

At step 1341, proportioning valve 1304 is closed, inlet valve 1308 is opened, and outlet valve 1310 is closed.

At step 1342, piston 1314 performs a portion of an intake stroke to attempt to intake liquid (i.e., A, B, C, D) from proportioning valve 1304. If there is no leak, then no fluid should flow.

At 1343, flow sensor 1306 is used to measure the flow of liquid (i.e., A, B, C, D).

In step 1344, if there is a leak in proportioning valve 1304, liquid (i.e., A, B, C, D) flows through flow sensor 1306 (as measured in step 1343), and a leak is determined.

FIG. 13B is a flowchart of a method of detecting a leak in an inlet valve. FIG. 13B will be discussed in conjunction with FIG. 13. The method depicted in FIG. 13B commences with step 1346.

At step 1346, flow sensor 1306 is calibrated for each liquid (i.e., A, B, C, D) stored in reservoir 1302.

At step 1347, chamber 1312 is filled with liquid (i.e., A, B, C, D). To fill chamber 1312 with liquid (i.e., A, B, C, D), proportioning valve 1304 is opened, inlet valve 1308 is opened, and outlet valve 1310 is closed. Piston 1314 then performs an intake stroke to fill chamber 1312. Once chamber 1312 is filled, inlet valve 1308 is closed.

In step 1348, piston 1314 then moves through a delivery stroke to compress the liquid (i.e., A, B, C, D) and pressurize chamber 1312.

At step 1349, an attempt is then made to measure a flow of liquid (i.e., A, B, C, D) in flow sensor 1306. If there is no leak, then no fluid should flow. If a flow of liquid (i.e., A, B, C, D) is measured in flow sensor 1306, the flow of liquid (i.e., A, B, C, D) is an indication that inlet valve 1308 has a leak.

In step 1350, the leak is determined.

In step 1351, after the leak is determined, metering may be performed to compensate for the leak.

In an alternate embodiment, the method depicted in FIG. 13B may be used to determine a leak in outlet valve 1310. FIG. 13B will now be discussed in conjunction with FIG. 13.

At step 1346, flow sensor 1313 is calibrated for each liquid (i.e., A, B, C, D) stored in liquid reservoir 1302. It should be appreciated that flow sensor 1313 may be positioned either before or after outlet valve 1310.

At step 1347, chamber 1318 is filled with liquid (i.e., A, B, C, D). To fill chamber 1318 with liquid (i.e., A, B, C, D), while inlet valve 1308 is closed and outlet valve 1310 is opened, piston 1314 moves upward through a delivery stroke and piston 1320 moves downward through an intake stroke. Performing the intake stroke fills chamber 1318. Once chamber 1318 is filled, outlet valve 1310 is closed. Piston 1320 then moves through a delivery (i.e., upward) stroke.

At step 1349, an attempt is then made to measure liquid (i.e., A, B, C, D) in flow sensor 1313. If there is no leak, then no fluid should flow. If flow is measured in flow sensor 1313, such flow is backflow from chamber 1318, and is an indication that outlet valve 1310 has a leak In step 1350, the leak is determined. It should be appreciated that the leak may be determined using any of the methods presented for determining leaks.

Figure 13C:
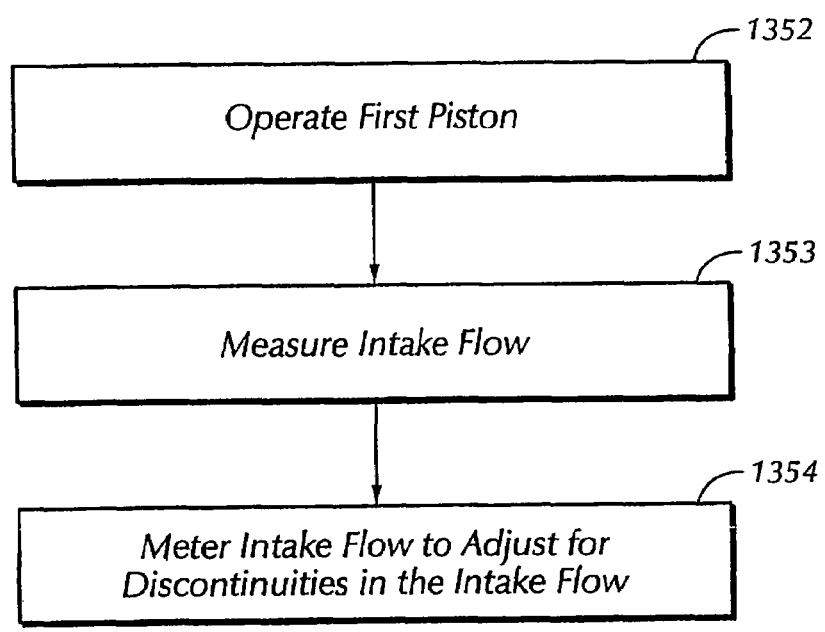
FIG. 13C is a flowchart of a method of performing a smooth intake stroke.

In step 1351, once the leak is determined, metering may be performed to compensate for the leak as stated at step 1351. FIG. 13C is a flowchart of a method of performing a smooth intake stroke. FIG. 13C will be discussed in conjunction with FIG. 13. The method depicted by FIG. 13C commences with step 1352.

At step 1352, pumping system 1300 is operating. During operation, proportioning valve 1304 allows liquid (i.e., A, B, C, D) from reservoir 1302 to be delivered to pumping unit 1311.

At step 1353, a flow sensor, such as flow sensor 1306, positioned between proportioning valve 1304 and pumping unit 1311, is used to measure the intake flow. In another embodiment, the flow sensor is not configured in the system. In one embodiment, the intake flow of liquid is not a continuous flow, and has discontinuities or increases and decreases in volume or flow.

At step 1354, motor/encoder system 1316 is used to meter the intake flow to adjust for any discontinuities in the intake flow. Metering the intake flow includes adjusting the speed and/or timing of piston 1314 using motor/encoder system 1316 in conjunction with computer 1324.

Figure 13D:
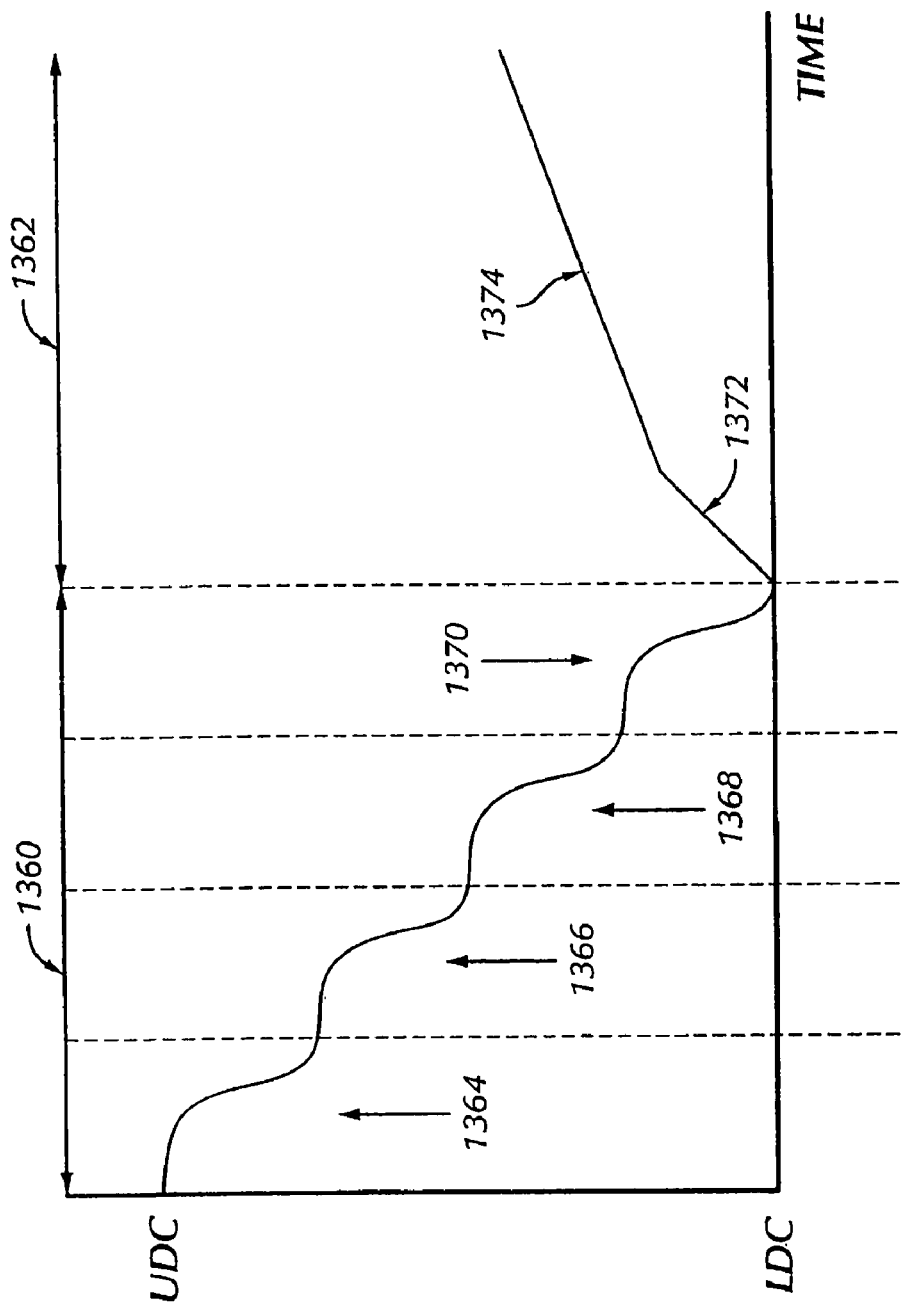
FIG. 13D is a graph relating to a method of metering the intake flow to adjust for discontinuities in the intake flow.

FIG. 13D is a graph relating to a method of metering the intake flow to adjust for discontinuities in the intake flow. As a result of metering, a smooth and highly precise intake flow may be accomplished. The individual liquids (A, B, C, and D) accelerate and facilitate smooth transitions when proportioning valve 1304 is switched. FIG. 13D will be discussed in conjunction with FIG. 13.

FIG. 13D presents a graph of the position of piston 1314 as a function of time. The upper limit of piston movement known as the upper dead center (UDC), and the lower limit of piston movement known as the lower dead center (LDC), are shown on the Y-axis of the graph. The liquid intake period is shown as 1360 and the liquid delivery period is shown as 1362 (i.e., for part of the delivery cycle). The portion of the graph associated with the intake of liquid A is shown as 1364, the portion of the graph associated with the intake of liquid B is shown as 1366, the portion of the graph associated with intake of liquid C is shown as 1368, and the portion of the graph associated with the intake of liquid D is shown as 1370. In addition, the initial compression and the final delivery of liquid, which occurs during the liquid delivery period 1362 is shown as 1372 and 1374, respectively.

As shown in FIG. 13D, piston 1314 is moving in a non-uniform manner to vary intake speed and the position of piston 1314 as shown by the portion of the graph associated with the intake of liquid A shown as 1364, the portion of the graph associated with the intake of liquid B shown as 1366, the portion of the graph associated with the intake of liquid C shown as 1368, and the portion of the graph associated with the intake of liquid D shown as 1370. As a result, no discontinuities in the intake of the liquid (i.e., A, B, C, D) are seen by pumping system 1300 when proportioning valve 1304 switches between liquids in reservoir 1302. Further, more precise metering is accomplished when no liquid or less liquid is drawn by piston 1314 while activating proportioning valve 1304. The corresponding liquids (i.e., A, B, C, D) are accelerated and decelerated very smoothly.

Figure 14:
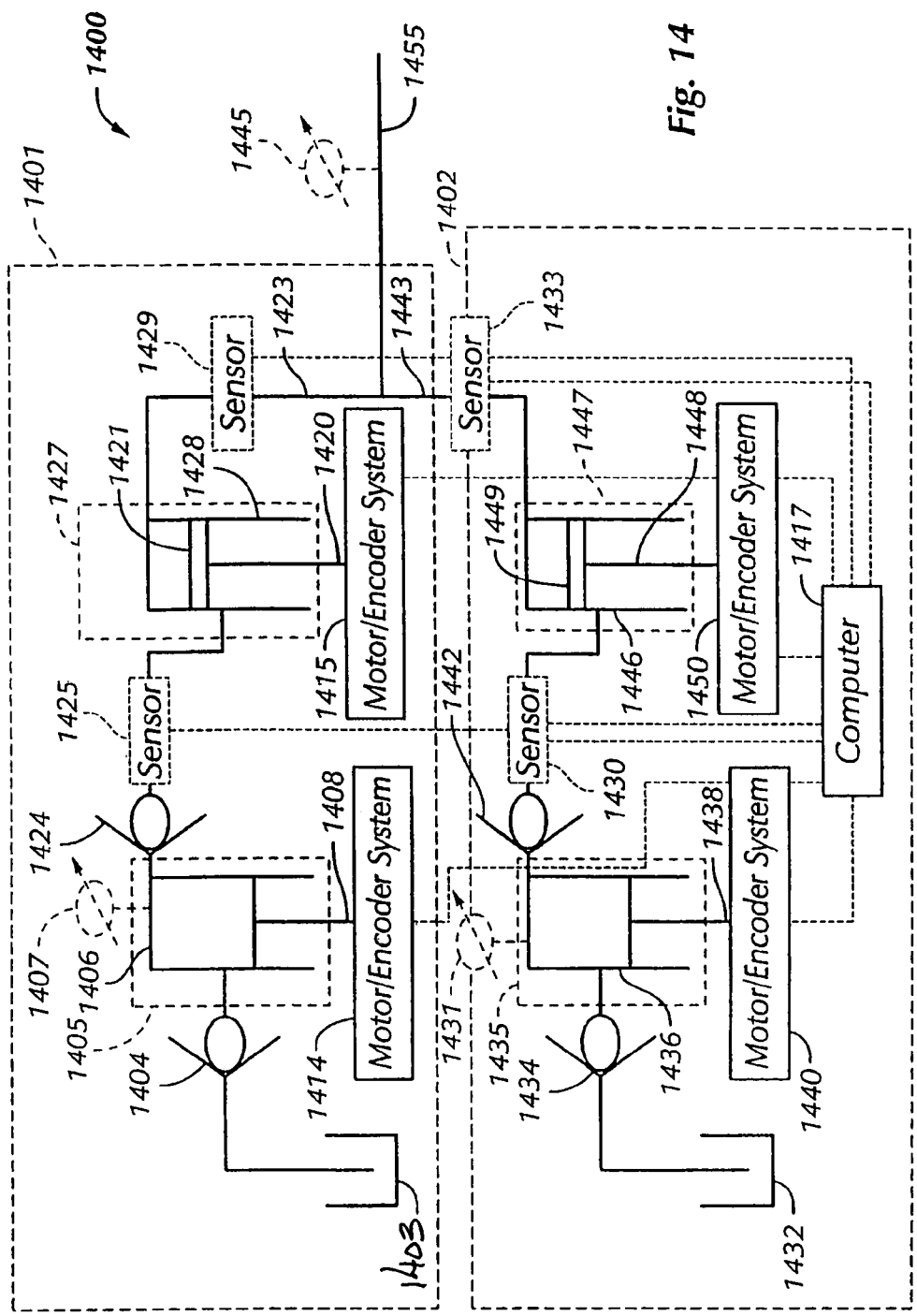
FIG. 14 is a schematic diagram of a dual-channel pumping system including flow sensors.

FIG. 14 is a schematic diagram of a dual-channel pumping system, i.e., a pumping system 1400. A channel 1401 and a channel 1402 are shown in the pumping system 1400. A liquid may be stored in a reservoir 1403. An inlet valve 1404 is positioned in series with a pumping unit 1405. Pumping unit 1405 includes a chamber 1406 and a piston 1408 capable of reciprocating motion within chamber 1406. Pumping unit 1405 may be configured with a pressure sensor 1407, which is positioned in chamber 1406, to detect the pressure in chamber 1406. An outlet valve 1424 is positioned in series with pumping unit 1405 and is positioned on an oppositely disposed side of chamber 1406 from inlet valve 1404. A motor/encoder system 1414 is connected to pumping unit 1405 and controls the reciprocating motion of piston 1408. A computer 1417 controls motor/encoder system 1414.

A pumping unit 1427 is in series with pumping unit 1405. Pumping unit 1427 includes a chamber 1428, and a piston 1420, with a seal 1421, capable of reciprocating motion within chamber 1428. Pumping system 1400 may be configured with a flow sensor 1425 positioned between pumping unit 1405 and pumping unit 1427. It should be appreciated that flow sensor 1425 may be positioned before or after outlet valve 1424. Pumping system 1400 may be configured with a flow sensor 1429 positioned on an output 1423 of channel 1401. A motor/encoder system 1415 is connected to pumping unit 1427 and controls the reciprocating motion of piston 1420. Computer 1417 controls motor/encoder system 1415.

A liquid may be stored in a reservoir 1432. An inlet valve 1434 is positioned in series with a pumping unit 1435. Pumping unit 1435 includes a chamber 1436 and a piston 1438 capable of reciprocating motion within chamber 1436. Pumping system 1400 may be configured with a pressure sensor 1431 positioned in chamber 1436. An outlet valve 1442 is in series with pumping unit 1435 and is positioned on an oppositely disposed side of chamber 1436 from inlet valve 1434. A motor/encoder system 1440 is connected to the pumping unit 1435 and controls the reciprocating motion of piston 1438. Computer 1417 controls motor/encoder system 1440.

A pumping unit 1447 is in series with pumping unit 1435. Pumping system 1400 may include a flow sensor 1430 positioned between pumping unit 1435 and pumping unit 1447. Pumping unit 1447 includes a chamber 1446, and a piston 1448, with a seal 1449, capable of reciprocating motion within chamber 1446. Pumping system 1400 may include a flow sensor 1433 positioned on an output 1443 of channel 1402. A motor/encoder system 1450 is connected to pumping unit 1447 and controls the reciprocating motion of piston 1448. Computer 1417 controls motor/encoder system 1450. Lastly, a pressure sensor 1445 is positioned on an output 1455 of the pumping system 1400.

Figure 14A:
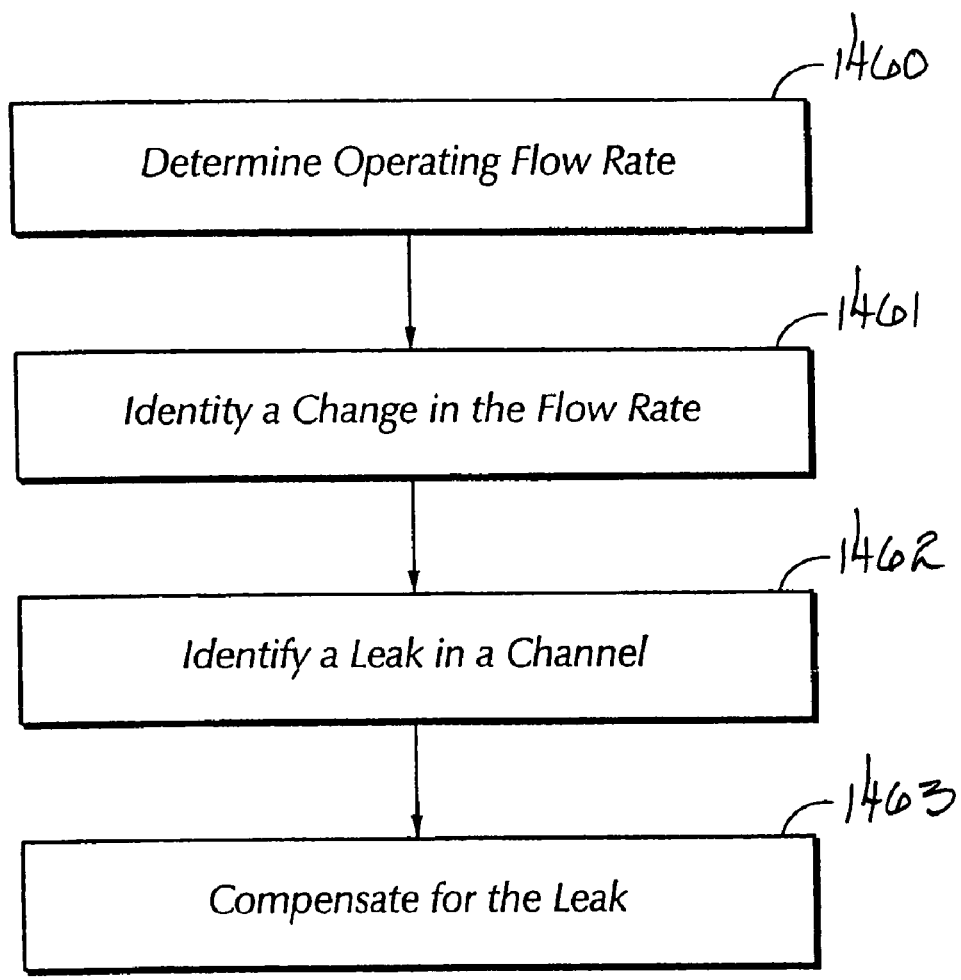
FIG. 14A is a flowchart of a method of operating a pumping system.

FIG. 14A is a flowchart of a method of operating a pumping channel. In addition, alternate embodiments of the method of operating a pumping channel are presented. For example, a method of detecting a leak in a first piston in a channel is presented. A method of detecting a leak in a second piston in a channel is presented. A method of detecting a leak when pumping system 1400 is operating at low flow rates (i.e., within the range of the flow sensor) is presented. A method of detecting a leak when pumping system 1400 is operating outside of the range of the flow sensor (i.e., high flow rates) is presented. FIG. 14A will be discussed in conjunction with FIG. 14.

In addition to the various embodiments, several parameters are defined for discussion purposes. In one embodiment, a nominal flow rate may be defined as a flow rate requested at output 1455. The nominal flow rate may be input by a user into computer 1417, and pumping system 1400 may coordinate between the various pumping units (i.e., 1407, 1427, 1435, and 1447) within pumping system 1400 to produce the nominal flow rate. In one embodiment, the measured flow rate may be defined as the flow rate measured by a flow sensor, such as flow sensors 1425, 1429, 1430, and 1433. Lastly, in one embodiment, a metered flow rate may be defined as a flow rate produced or recorded by motor/encoder system 1414, motor/encoder system 1415, motor/encoder system 1440, or motor/encoder system 1450. In one embodiment of the present invention, a leak is equivalent to the metered flow rate minus the measured flow rate (i.e., leak=metered flow rate−measured flow rate).

A method of determining leaks is presented in FIG. 14A. The method commences with step 1460.

At step 1460, the flow rate of a pumping unit (i.e., 1405, 1427, 1435, 1447) is determined. The flow rate may be determined by measuring, metering, etc. Further, the flow rate may be determined at various positions within pumping system 1400.

At step 1461, a change in the flow rate is determined. In one embodiment, a change in the flow rate is determined by measuring the change with a flow sensor (i.e., 1425, 1429, 1430, 1433).

At step 1462, a leak is identified and calculated in the channel.

At step 1463, compensation is made for the leak.

A method of determining a leak in a pumping unit in a channel when the pumping unit is operating within the range of a flow sensor is presented. The method will be discussed using FIG. 14 in combination with the flow diagram presented in FIG. 14A. First, a constant flow rate is metered (i.e., used) for as the nominal flow rate.

At step 1460 of FIG. 14A, the flow rate is determined. For example, flow sensor 1425 or flow sensor 1430 is used to determine the measured flow rate of pumping unit 1405 or pumping unit 1435, respectively. Since flow sensor 1425 and flow sensor 1430 are connected to computer 1417, computer 1417 is capable of recording the flow rate detected by each flow sensor (i.e., 1425, 1430) over time.

At step 1461, each flow sensor (i.e., 1425, 1430) is monitored to identify a change in the flow rate.

At step 1462, a change in the flow rate signifies a leak in a pumping unit. In one embodiment, this assumes a constant metered flow rate.

At step 1463, compensation is made for the leak in the channel.

In a second embodiment, at step 1460 of FIG. 14A, the flow rate is determined. For example, flow sensor 1425 or flow sensor 1430 is used to determine the measured flow rate of pumping unit 1405 or pumping unit 1435, respectively.

At step 1461, the metered flow rate is determined. For example, motor/encoder system 1414 and motor/encoder system 1440 are each used in combination with computer 1417 to determine a metered flow rate for each pumping unit (i.e., 1405 and 1435, respectively).

At step 1462, a leak is identified and calculated. In one embodiment, the leak equals the metered flow rate minus the measured flow rate (i.e., leak=metered−measured).

At step 1463, once the leak has been calculated, compensation is made for the leak. Compensation for the leak may include operating pumping units 1405 and 1435 to deliver additional liquid, which is equivalent to the amount of the leak.

In another embodiment of the present invention, a method of determining a leak in a channel when the output of the channel is within the operating range of a flow sensor is presented. The method will be discussed using FIG. 14 in combination with the flow diagram presented in FIG. 14A.

At step 1460 of FIG. 14A, the flow rate is determined. For example, flow sensor 1429 and flow sensor 1433 is used to determine the measured flow rate of channels 1401 and 1402, respectively. Since flow sensor 1429 and flow sensor 1433 are connected to computer 1417, computer 1417 is capable of recording the flow rate detected by each flow sensor (i.e., 1429, 1433) over time.

At step 1461, each flow sensor (i.e., 1429, 1433) is monitored to identify a change in the flow rate. In one embodiment, this assumes a constant metered flow rate.

At step 1462, a change in the flow rate signifies a leak in the channel (i.e., 1401, 1402).

At step 1463, compensation is made for the leak in the channel (i.e., 1401, 1402). In one embodiment, compensating for the leak in the channel (i.e., 1401, 1402) may include operating a pumping unit (1405, 1435) in the channel (i.e., 1401, 1402)) to output liquid equal to the amount of the leak. In a second embodiment, compensating for the leak in the channel may include operating a pumping unit (i.e., 1427, 1447) in the channel to output liquid equal to the amount of the leak. In a third embodiment, compensating for the leak in the channel may include operating pumping units (1405, 1435) in the channel in combination with a pumping unit (1427, 1447) in a channel to output liquid equal to the amount of the leak. It should be appreciated that the foregoing method may be extended to any amount of pumping units configured in a channel.

At step 1460 of FIG. 14A, in a second embodiment of determining a leak in a channel when the output of the channel is within the operating range of a flow sensor, the flow rate is determined. For example, flow sensor 1429 or flow sensor 1433 may be used to determine the measured flow rate of channel 1401.

At step 1461, the metered flow rate is determined for each pumping unit (i.e., 1405, 1427, 1435, 1447). For example, motor/encoder system 1414, motor/encoder system 1440, motor/encoder system 1415, and motor/encoder system 1450 are each used in combination with computer 1417 to determine a metered flow rate for each pumping unit (i.e., 1405, 1435, 1427, 1447, respectively).

At step 1462, a leak is identified and calculated. In one embodiment, the leak equals the metered flow rate minus the measured flow rate (i.e., leak=metered−measured).

At step 1463, once the leak has been calculated, compensation is made for the leak. Compensation for the leak may include operating pumping units 1405, 1427, 1435, and 1447 to deliver additional liquid, which is equivalent to the amount of the leak calculated for each channel (i.e., 1401, 1402).

In a number of alternate embodiments, once a leak has been determined, a number of methods are presented for compensating for the leak in pumping system 1400 as stated in step 1463. For example, individual metering methods may be implemented or integrated metering methods may be implemented. With an individual metering method, the flow of liquid through a single pumping unit (i.e., 1405, 1427, 1435, 1447) may be metered to compensate for the leak in the channel (i.e., 1401, 1402). Each pumping unit (i.e., 1405, 1427, 1435, 1447) in a channel (i.e., 1401, 1402) may be individually adjusted to compensate for a leak in the channel (i.e., 1401, 1402). For example, pumping units 1405 and 1427 may be individually adjusted to meter liquid through the pumping unit (i.e., 1405, 1427) and consequently compensate for the leak in channel 1401. In a similar manner, pumping units 1435 and 1447 may be individually adjusted to meter liquid through the pumping unit (i.e., 1435, 1447) and consequently compensate for the leak in channel 1402. In the alternative, integrated metering methods may be implemented. For example, if there is a leak in channel 1401, pumping unit 1405 ande pumping unit 1427 may operate in a coordinated fashion to compensate for the leak.

Figure 15A:
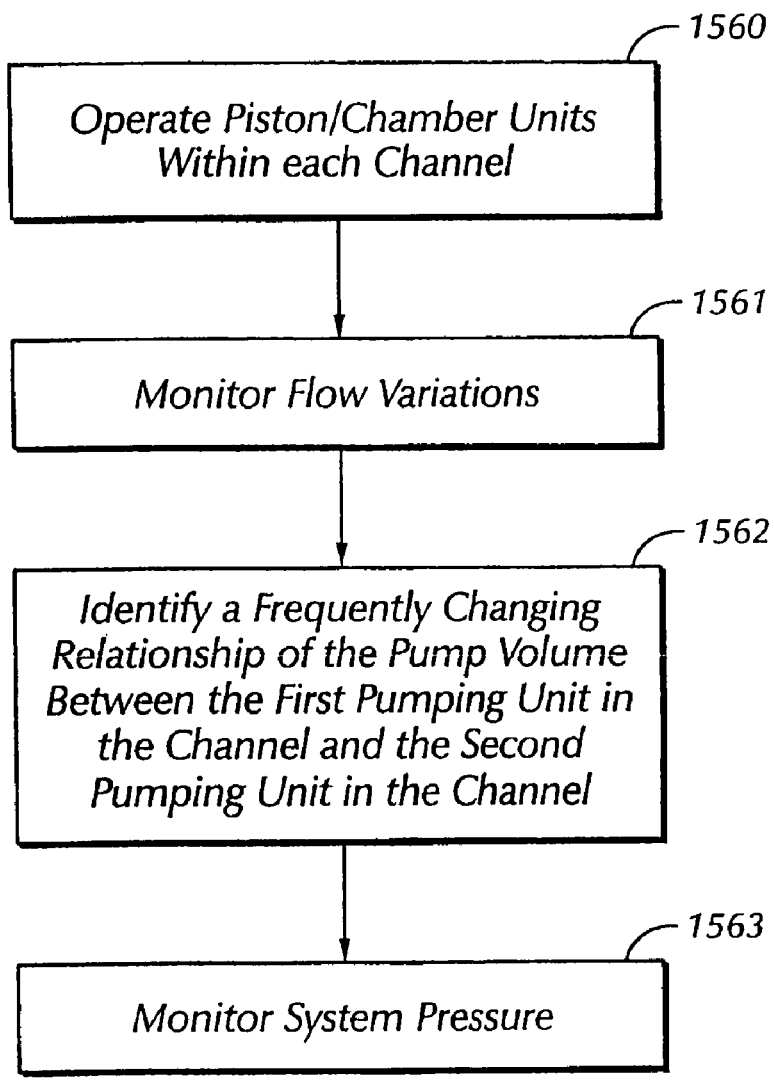
FIG. 15A is a flowchart of a method of determining a leak in a piston.

FIG. 15A is a flowchart of a method of determining a leak in a piston seal with a flow sensor positioned between two pumping units in a channel of a pumping system. FIG. 15A will be discussed in conjunction with FIG. 14 and FIG. 15B.

The flow diagram of FIG. 15A depicts a method of determining a leak in seal 1421 using sensor 1425, and/or determining a leak in seal 1449 using sensor 1430. The method commences with step 1560.

At step 1560, each pumping unit (i.e., 1405, 1427, 1435, 1447) within each channel (i.e., 1401, 1402) is operating.

At step 1561, the flow variations of channel 1401 and channel 1402 are monitored.

In one embodiment, monitoring the flow variations in each channel (i.e., 1401, 1402) includes plotting the flow variations between each pumping unit (i.e., 1405, 1427, 1435, 1447) in a channel (i.e., 1401, 1402). For example, monitoring the flow variation in each channel (i.e., 1401, 1402) includes plotting the flow rate of one pumping unit (i.e., 1405, 1427, 1435, 1447) relative to another pumping unit (i.e., 1405, 1427, 1435, 1447) in the channel (i.e., 1401, 1402). In another embodiment, monitoring the flow variations may include plotting the metering variations of each pumping unit (i.e., 1405, 1427, 1435, 1447) in each channel (i.e., 1401, 1402).

Figure 15B:
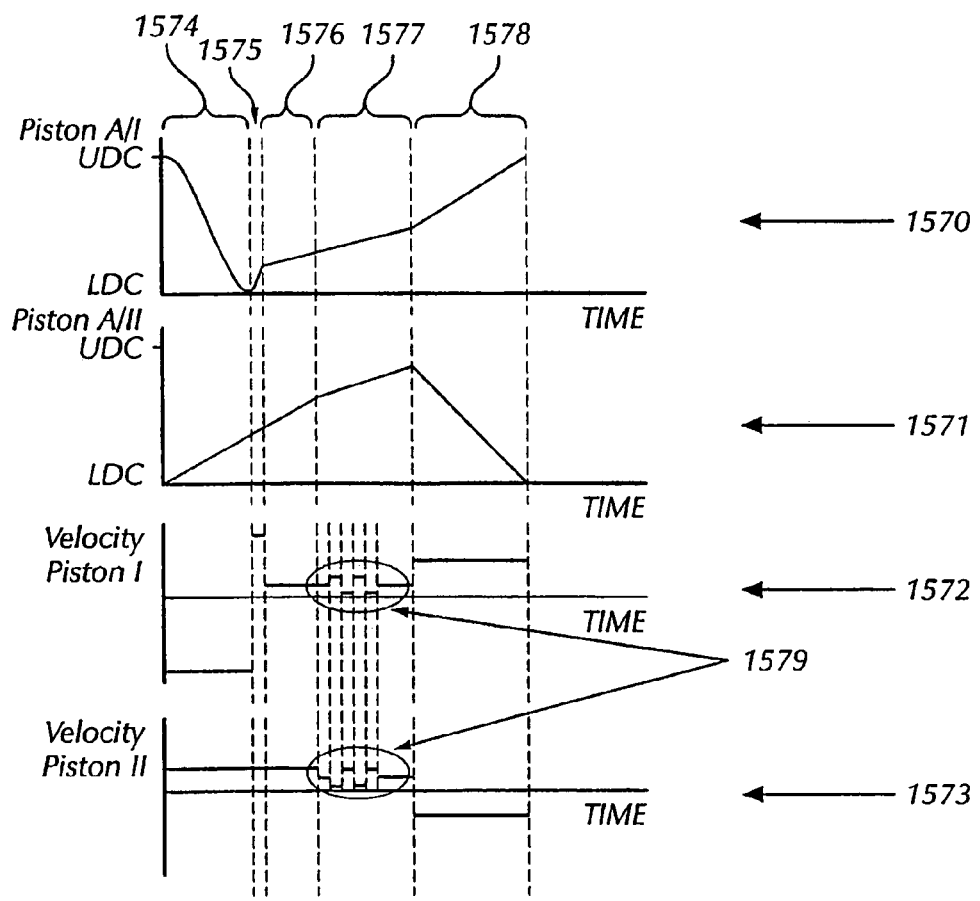
FIG. 15B is a graph depicting flow variations within a channel.

Using FIG. 15B, graphs of the flow variations within a channel (i.e., 1401, 1402) are schematically presented. In one embodiment, the pumping units 1405 and 1427 are positioned in series and pumping units 1435 and 1447 are positioned in series. A graph 1570 represents a piston that is deployed in a pumping unit 1405, 1435, positioned in a channel, and a graph 1571 represents a piston that is deployed in a pumping unit 1427, 1447 positioned in the channel. Both graphs (i.e., 1570 and 1571) display movement of piston versus time as the channel operates. A graph 1572 displays the velocity of a piston (i.e., in a pumping unit 1405, 1435) in a channel versus time. A graph 1573 displays the velocity of a piston in a pumping unit 1427, 1447 in the same channel versus time.

During an interval 1574, there is a liquid intake period into pumping unit 1405, 1435. Interval 1574 is bounded by the vertical axes on each graph and the dashed lines to the right of the vertical axes.

During an interval 1575, there is a fast pre-compression jump of the piston chamber 1406, 1436. Interval 1575 is bounded by vertical dashed lines.

During an interval 1576, there is a final compression of chambers 1406 and 1436.

During an interval 1577, there is a delivering of liquid with the pumping units (i.e., 1405, 1435; 1427, 1447) within a channel. Interval 1577 is bounded by vertical dashed lines.

During an interval 1578, pumping units 1405 and 1435 deliver the liquid into the pumping system, and pumping units 1427 and 1447 are filled by pumping units 1405 and 1435, respectively.

Graph 1570 represents the movement of a piston positioned in a pumping unit in a channel. For example, graph 1570 may represent the movement of piston 1408 or piston 1438.

Graph 1571 represents the movement of a piston positioned in a pumping unit in a channel. For example, graph 1571 may represent the movement of piston 1420 or piston 1448. During the liquid intake period, i.e., interval 1574, the piston (i.e., 1408 or 1438) in the channel moves from upper dead center (UDC) to lower dead center (LDC). In addition, the velocity of the pistons (i.e., 1408 and 1420 or 1438 and 1448) may be shown schematically by graphs 1572 and 1573. The velocity of the piston (i.e., 1408, 1438) within a channel is chosen so that pumping unit 1405 and/or pumping unit 1435 is/are outputting liquid within the operating range of flow sensor 1425 and/or flow sensor 1430. Therefore, flow sensors 1425 and/or 1430 will be able to measure the flow rate. The piston within the channel, such as piston 1420 and/or piston 1448, is then used to deliver the remainder of the requested flow rate (i.e., nominal flow rate). Pressure sensor 1445 is used to measure the pressure drop of pumping system 1400. In addition, pressure sensor 1445 is used to correlate the flow rate on output 1455.

At step 1562 of FIG. 15A, the frequently changing relationship between the pumped volume between two pistons (i.e., 1408 and 1420 and/or 1438 and 1448) within the same channel is identified. In FIG. 15B, this frequently changing relationship is shown as detail 1579. The frequently changing relationship of the pump volume between two pumping units within the same channel in combination with different pressure levels corresponding to the frequently changing piston speeds at the output of the pumping system is an indication of a leak. For example, the changing relationship depicted in detail 1579 is indicative of a dynamic leak in seal 1421 and/or seal 1449, if pressure sensor 1445 indicates a lower pressure on output 1455 when the volume of liquid output from the piston(s) (i.e., 1420 and/or 1448) in the channel is higher than the volume of liquid output by piston 1408 and/or piston 1438 in channel 1401 and/or channel 1402. It should be appreciated that dynamic leaks in piston/seal combinations can be detected. In a second embodiment, only one channel is connected to output 1455.

It should be appreciated that a number of different pumping scenarios may be implemented and still remain in accordance with the teachings of the present invention. It should also be appreciated that individual pumping units may operate at specific times. For example, operating the piston (e.g. 1408 and 1438) within the channel without operating piston 1420 and/or piston 1448 within channel 1401 and/or channel 1402, respectively, is within the scope of the present invention.

Figure 15C:
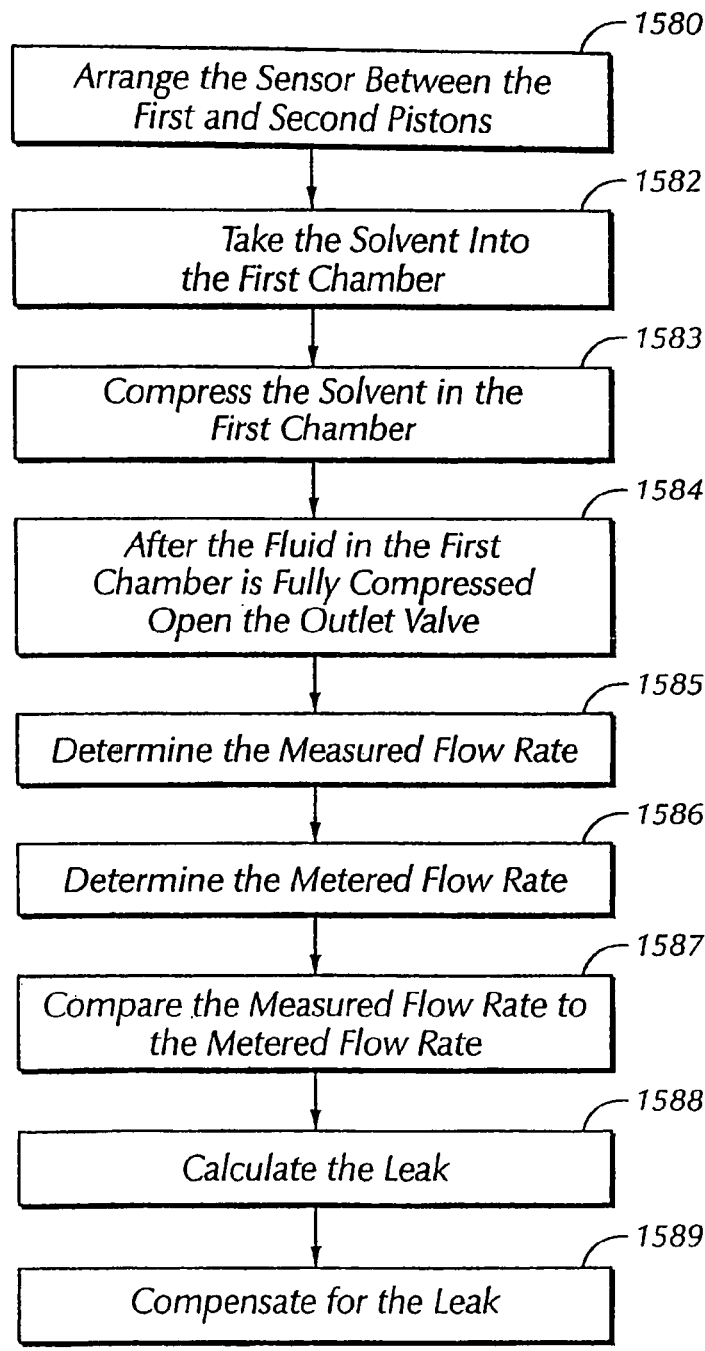
FIG. 15C is a flowchart of a method of determining the piston velocity required to produce the nominal (desired) flow rate.

FIG. 15C is a flowchart of a method of determining a piston velocity required to produce a nominal (desired) flow rate. In one embodiment, a flow sensor is used to determine a leak rate. A nominal flow rate is determined by performing metering as defined by a metered flow rate, determining the delivered flow rate (i.e., measured flow rate), calculating the leak by comparing metered flow rate and measured flow rate, and calculating correction and/or compensation factors. Metering is then performed to operate the pumping system at the nominal rate. For example, using pumping unit 1405, metering is performed using motor/encoder system 1414. The metering outputs liquid from pumping unit 1405 at a metered flow rate. Flow sensor 1425 is then used to measure the flow rate. The measurement produces a measured flow rate. The difference between the metered flow rate and the measured flow rate is then referred to as the leak rate. Motor/encoder system 1414 then adjusts the operation of piston 1408 to compensate for the leak rate. In one embodiment, compensating for the leak rate includes adjusting the operation of piston 1408 to produce an additional amount of liquid from pumping unit 1405 to compensate for the liquid lost as a result of the leak.

FIG. 15C will be discussed in conjunction with FIG. 14. The method depicted in FIG. 15C commences with step 1580.

At step 1580, a flow sensor is implemented between pumping units within a channel. For example, flow sensor 1425 is positioned between pumping unit 1405 and pumping unit 1427. In another embodiment, flow sensor 1430 is positioned between pumping unit 1435 and pumping unit 1447. From step 1580, the method progresses to step 1582.

At step 1582, liquid is taken into chamber 1406 and/or chamber 1436. This requires a downward stroke of piston 1408 and/or piston 1438. In one embodiment of the present invention, the downward stroke is a quick downward stroke. Typically, it is possible to draw in 100 μl liquid within less than 1 second.

At step 1583, after filling chamber 1406 and/or chamber 1436, liquid in chamber 1406 and/or chamber 1436 is compressed. In one embodiment, the liquid is compressed rapidly. For example, in one embodiment compress chamber 1406 and/or chamber 1436 rapidly. In one embodiment, the initial upward stroke of piston 1408 and piston 1438 is performed quickly, within 100 ms.

At step 1584, when the liquid in the chamber is fully compressed, open the outlet valve. For example, after the liquid stored in chamber 1406 and/or chamber 1436 is fully compressed, open outlet valve 1424 and/or outlet valve 1442.

At step 1585, a flow sensor, such as flow sensor 1425 and/or flow sensor 1430 is/are used to detect the measured rate. Once the outlet valve 1424 and/or outlet valve 1442 is/are opened, flow sensor 1425 and/or flow sensor 1430 will detect the flow rate delivered by piston 1408 and/or piston 1438. Since flow sensor 1425 and/or flow sensor 1430 is/are calibrated, the reading attained from flow sensor 1425 and/or flow sensor 1430 is the actual (i.e., measured) flow rate and can be determined by reading flow sensor.

At step 1586, the encoder located in the motor/encoder system is read. The number of steps produced by the motor/encoder system is equal the metered flow rate.

At step 1587, compare the actual flow rate with the metered flow rate.

At step 1588, a comparison of the actual (i.e., measured) flow rate and the metered flow rate is performed to calculate the leak.

In step 1589, once the leak has been calculated, the leak can be compensated for by metering at a new calculated piston velocity, etc.

A second method of determining the piston velocity required to produce the nominal (desired) flow rate is presented. In the second method, a leak is determined in an outlet valve when a second piston is pumping. In one embodiment, the method depicted in the flow diagram of 13B is implemented.

At step 1347, chamber 1428 and/or chamber 1446 is filled. Outlet valve 1424 and/or outlet valve 1442 is closed.

At step 1348, piston 1421 and/or piston 1449 performs a delivery stroke.

At step 1349, flow sensor 1425 and/or flow sensor 1430 is/are used to measure backflow.

At step 1350, since the backflow is equivalent to the amount of the leak; the backflow is used to determine the leak.

At step 1351, piston 1421 and/or piston 1449 is/are adjusted to compensate for the leak. In one embodiment, compensating for the leak includes calculating a new piston velocity required to produce the nominal or desired flow rate at the output.

Using FIG. 14 to discuss the method, chamber 1427 and/or chamber 1447 is/are filled with liquid. Outlet valve 1424 and/or outlet valve 1442 is/are closed. Piston 1421 and/or piston 1448 perform(s) a delivery stroke. Flow sensor 1425 and/or flow sensor 1430 is/are used to measure any flow of liquid. A flow of liquid indicates a leak in outlet valve 1424 and/or outlet valve 1442. The leak is equivalent to the flow of liquid. A new piston velocity may then be determined to compensate for the leak. The new piston velocity may be calculated by computer 1417 and implemented by motor/encoder system 1415 and/or motor/encoder system 1450, respectively. Once the compensation is made, a nominal flow rate will be produced at output 1455.

It should be appreciated that once outlet valve 1424 and/or outlet valve 1442 is/are opened, and chamber 1428 and/or chamber 1446 is/are fully compressed, the creeping effect of pumping system 1400 must be considered when calculating the leak rate. Creeping is a natural function of pumping system 1400, in which the components of pumping system 1400 settle. During creeping, some leakage may occur. However, once creeping effects have terminated, pumping system 1400 should operate in steady state (i.e., with or without leakage).

In one embodiment, a method of determining leaks when the flow rate is higher than the range of the flow sensor is presented. A chamber in a first pumping unit is filled with fluid. At the same time that the chamber in the first pumping unit is being filled with fluid, the second pumping unit is delivering the desired flow rate. After filling the first pumping unit, the piston in the first pumping unit moves upward to compress the liquid in the first chamber at the same time the second piston is delivering the desired flow rate. Once the compression is complete, the outlet valve associated with the first pumping unit is opened. Afterwards, the first pumping unit delivers a portion of total flow rate into the system. The portion of the total flow rate is selected within the range of the flow sensor. A leak is then determined. The difference between the metered flow rate and the measured flow rate defines the leak. At the same time, the second piston delivers the remainder (nominal flow rate−measured flow rate) of the desired flow rate into the system. In the case where the first piston is delivering the total flow rate into the system, the metered flow rate is equivalent to the nominal flow rate plus the leak (i.e., nominal flow rate+the leak).

Using FIG. 14, chamber 1406 and/or chamber 1436 is/are filled with liquid. At the same time, pumping unit 1427 and/or pumping unit 1449 is/are delivering the desired flow rate. After filling chamber 1406 and/or chamber 1436, piston 1408 and/or piston 1438, respectively, move upward to compress the solvent in chamber 1406 and/or chamber 1436 at the same time that piston 1420 and/or piston 1448 is/are delivering the desired flow rate. Once the compression is complete, outlet valve 1424 and/or outlet valve 1442 is/are opened. Afterwards, pumping unit 1405 and/or pumping unit 1435 deliver(s) a portion of total flow rate into the system. The portion of the total flow rate is selected within the range of flow sensor 1425 and/or flow sensor 1430. A leak is then determined. The difference of metered flow rate and measured flow rate defines the leak. At the same time, piston 1420 and/or piston 1448 deliver(s) the remainder (nominal flow rate−measured flow rate) of the desired flow rate into the system. In the case where piston 1408 and/or piston 1438 is/are delivering the total flow rate into the system, the metered flow rate is equivalent to the nominal flow rate plus the leak (i.e., nominal flow rate+the leak).

Figure 15D:
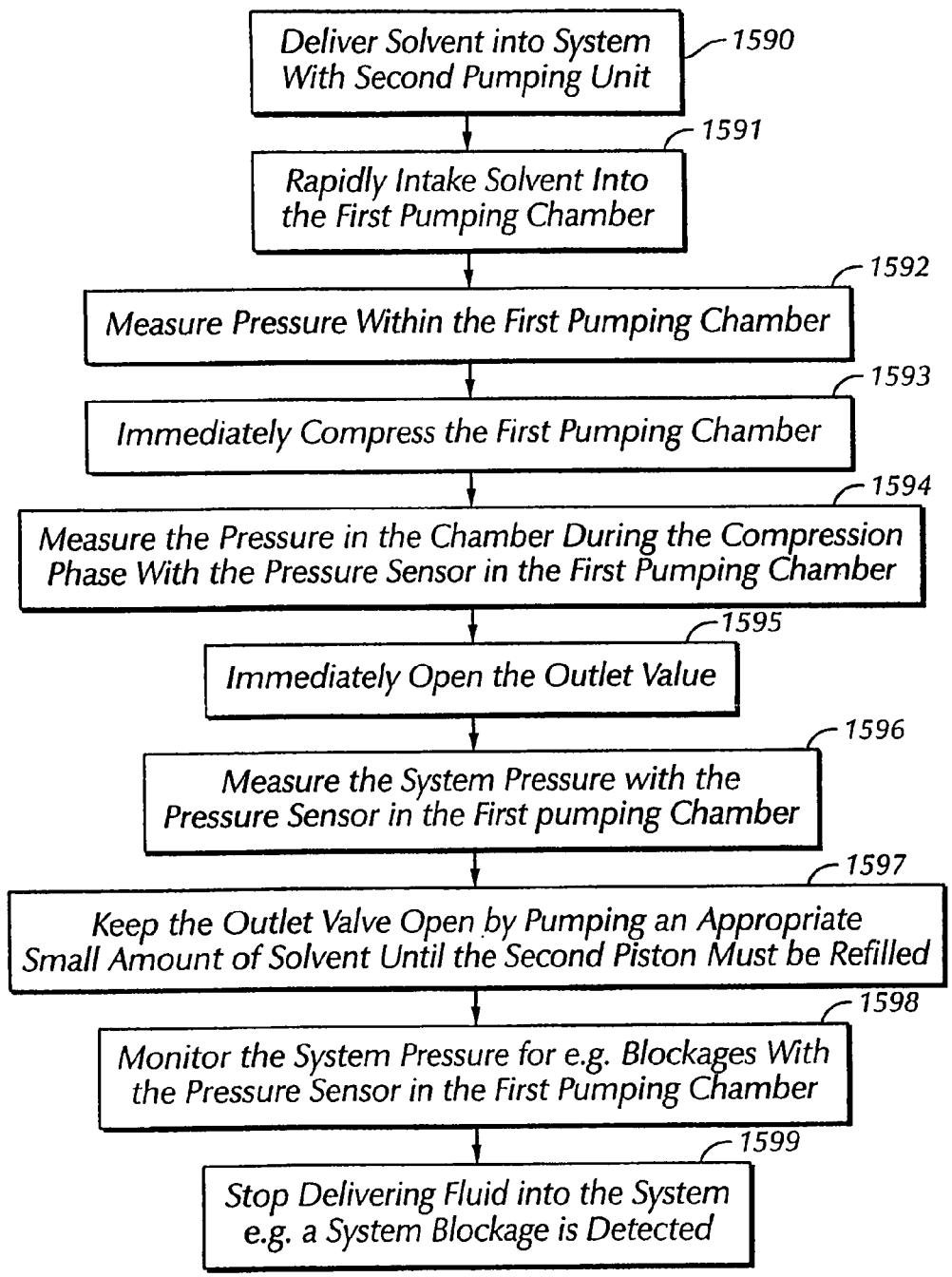
FIG. 15D is a flowchart of a method of monitoring compression phases in a pumping chamber and monitoring the system pressure of a chromatography system.

FIG. 15D is a flowchart of a method of monitoring compression phases in a pumping chamber and monitoring the system pressure of a chromatographic system. In one embodiment, a single pressure sensor, such as pressure sensor 1407 and/or pressure sensor 1431 is/are required to monitor a compression phase of chamber 1406 and/or chamber 1436, and to monitor system pressure of the chromatographic system. FIG. 15D will be described in conjunction with FIG. 14. The method depicted in FIG. 15D commences with step 1590.

At step 1590, solvent (i.e., liquid) is delivered into a pumping system using a second pumping unit.

At step 1591, the first piston is used to rapidly intake liquid into the chamber in the first pumping unit (i.e., first pumping chamber).

At step 1592, pressure is measured within the chamber of the first pumping unit.

At step 1593, the liquid in the first pumping chamber is immediately compressed.

At step 1594, the pressure in the first pumping chamber is measured during the compression phase with the pressure sensor in the first pumping chamber.

At step 1595, the outlet valve associated with the first pumping chamber is immediately opened.

At step 1596, the pressure in the first pumping chamber may be used to measure the system pressure of pumping system 1400.

At step 1597, the outlet valve is kept opened by pumping a small amount of liquid until the second chamber must be refilled.

At step 1598, monitor the system pressure and blockages with the pressure sensor in the first pumping chamber.

At step 1599, delivery of liquid into the system is stopped if a system blockage is detected.

FIG. 14 will be used to demonstrate the method detailed in the flow diagram in FIG. 15D.

At step 1590, solvent (i.e., liquid) is delivered into the system using a second pumping unit. Therefore, pumping unit 1427 and/or pumping unit 1447 is/are used to deliver liquid into the system.

At step 1591, piston 1408 and/or piston 1438 rapidly intake solvent into chamber 1406 and/or chamber 1436. Pumping unit 1405 and/or pumping unit 1435 rapidly intake liquid into chamber 1406 and/or chamber 1436, respectively.

At step 1592, pressure is measured within chamber 1406 and/or chamber 1436. Pressure sensor 1407 is used to measure the pressure of chamber 1406, and/or pressure sensor 1431 is used to measure the pressure of chamber 1436.

At step 1593, the liquid in chamber 1406 and/or chamber 1436 is immediately compressed. Piston 1408 is used to compress liquid such as solvent stored in chamber 1406, and/or piston 1438 is used to compress liquid such as solvent stored in chamber 1436.

At step 1594, the pressure in chamber 1406 and/or chamber 1436 is measured during the compression phase with pressure sensor 1406 and/or pressure sensor 1431. As piston 1408 is compressing the liquid in chamber 1406, pressure sensor 1407 is used to measure the pressure in chamber 1406. As piston 1438 compresses liquid in chamber 1436, pressure sensor 1431 is used to measure the pressure in chamber 1436.

At step 1595, the outlet valve associated with the first pumping chamber is immediately opened. Outlet valve 1424 and/or outlet valve 1442 is/are immediately opened.

At step 1596, the pressure in the first pumping chamber may be used to measure the system pressure of pumping system 1400. After opening outlet valve 1424 and/or outlet valve 1442, pressure sensor 1407 and/or pressure sensor 1431 may be used to measure the system pressure.

At step 1597, the outlet valve is kept opened by pumping a small amount of liquid until the second piston must be refilled. Outlet valve 1424 and/or outlet valve 1442 remain(s) open, and piston 1408 and/or piston 1438 deliver(s) a small amount of liquid until the second pumping unit, i.e., 1427 and/or pumping unit 1447, must be refilled.

At step 1598, monitor the system pressure and blockages with the pressure sensor in the first pumping chamber. Pressure sensor 1407 and/or pressure sensor 1431 is/are used to measure system pressure to detect blockage in pumping system 1400. Changes in pressure measured by pressure sensor 1407 and/or pressure sensor 1431 when pressure sensor 1407 and/or pressure sensor 1431 is/are used to measure system pressure, will signal a blockage in the pumping system.

At step 1599, delivery of liquid into the system is stopped if a system blockage is detected. If a blockage is detected, delivery of solvent with pumping unit 1427 and/or pumping unit 1447 is terminated.

Figure 16:
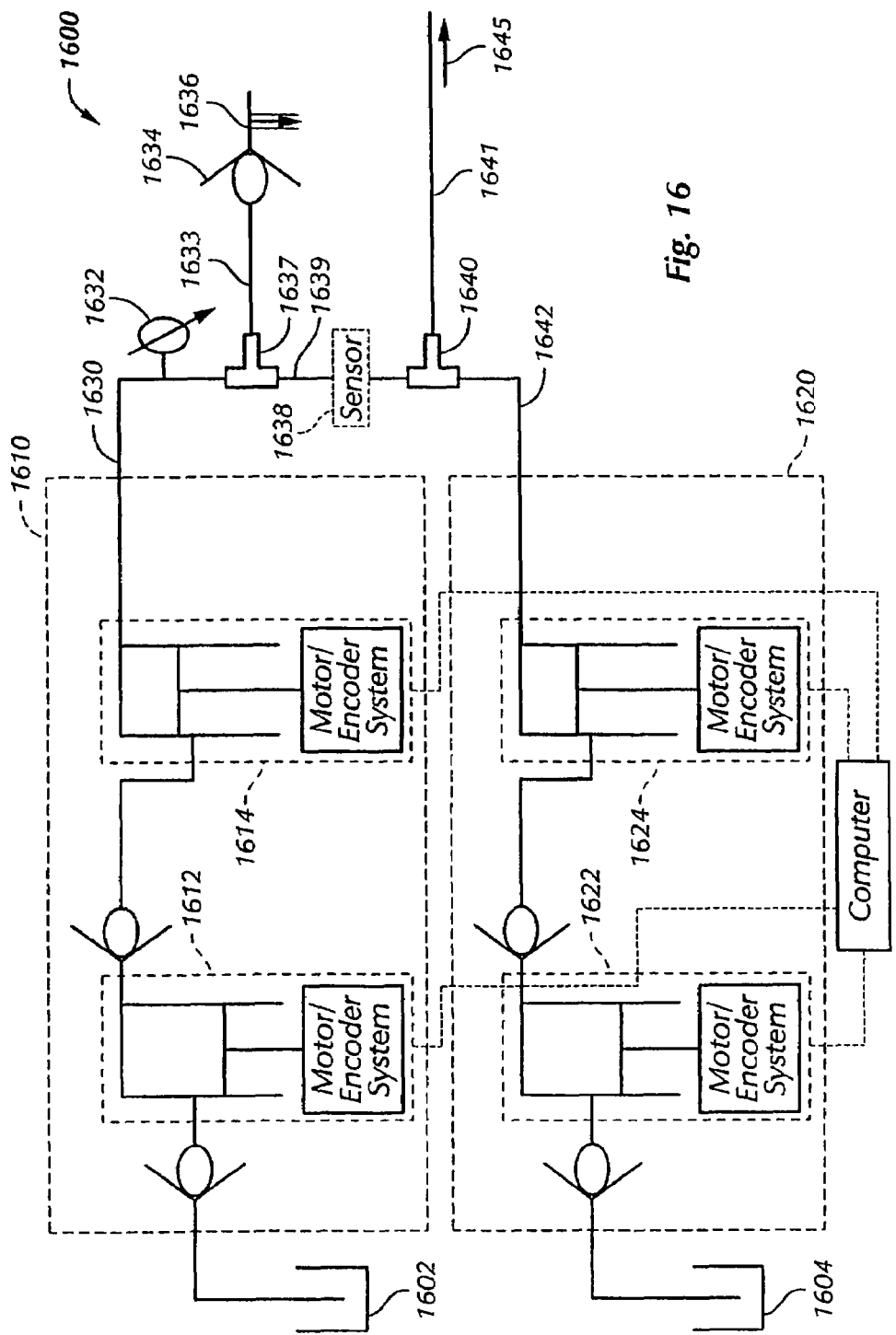
FIG. 16 is a schematic diagram of a dual-channel pumping system including a flow sensor and a pressure sensor.

FIG. 16 is a schematic diagram of a dual-channel pumping system, i.e., a pumping system 1600. Pumping system 1600 includes a channel 1610 and a channel 1620. Channel 1610 includes a pumping unit 1612 in series with a pumping unit 1614. Channel 1620 includes a pumping unit 1622 in series with a pumping unit 1624. A reservoir 1602 stores a first liquid. A reservoir 1604 stores a second liquid. A channel output 1630 is connected to channel 1610. A channel output 1642 is connected to channel 1620. A pressure sensor 1632 is positioned on channel output 1630. Channel output 1630 is connected to a waste output 1633 through a T-junction 1637. A purge valve 1634 is positioned on waste output 1633. A waste exhaust 1636 provides an output for liquid conveyed on waste output 1633.

A T-junction 1640 provides a connection between channel output 1642 and a system output 1641'. System output 1641 provides a pathway to a chromatography system (not shown in FIG. 16). A conveyance 1639 is shown between T-junction 1637 and T-junction 1640. In one embodiment, a flow sensor 1638 is positioned along conveyance 1639. In another embodiment, flow sensor 1638 is not included in pumping system 1600. It should also be appreciated that in an alternate embodiment, T-junction 1637, purge valve 1634, waste output 1633, and waste exhaust 1636 may be positioned in channel output 1642.

During operation, a liquid is pumped through channel 1610 to channel output 1630, and a liquid is pumped through channel 1620 to the channel output 1642. A mixture of channel output 1630 and channel output 1642 is combined at T-junction 1640 and conveyed on system output 1641, as represented by arrow 1645. It should be appreciated that while an embodiment of a specific pumping unit is detailed in each channel (i.e., 1610, 1620), the present invention may be directed to pumping systems with different channel components (i.e., pumping units, valves, etc.). It should also be appreciated that more than two channels may be connected at T-junction 1640. In addition, waste from channel output 1630 and channel output 1642 may travel along waste output 1633, through purge valve 1634, and through waste exhaust 1636.

Figure 16A:
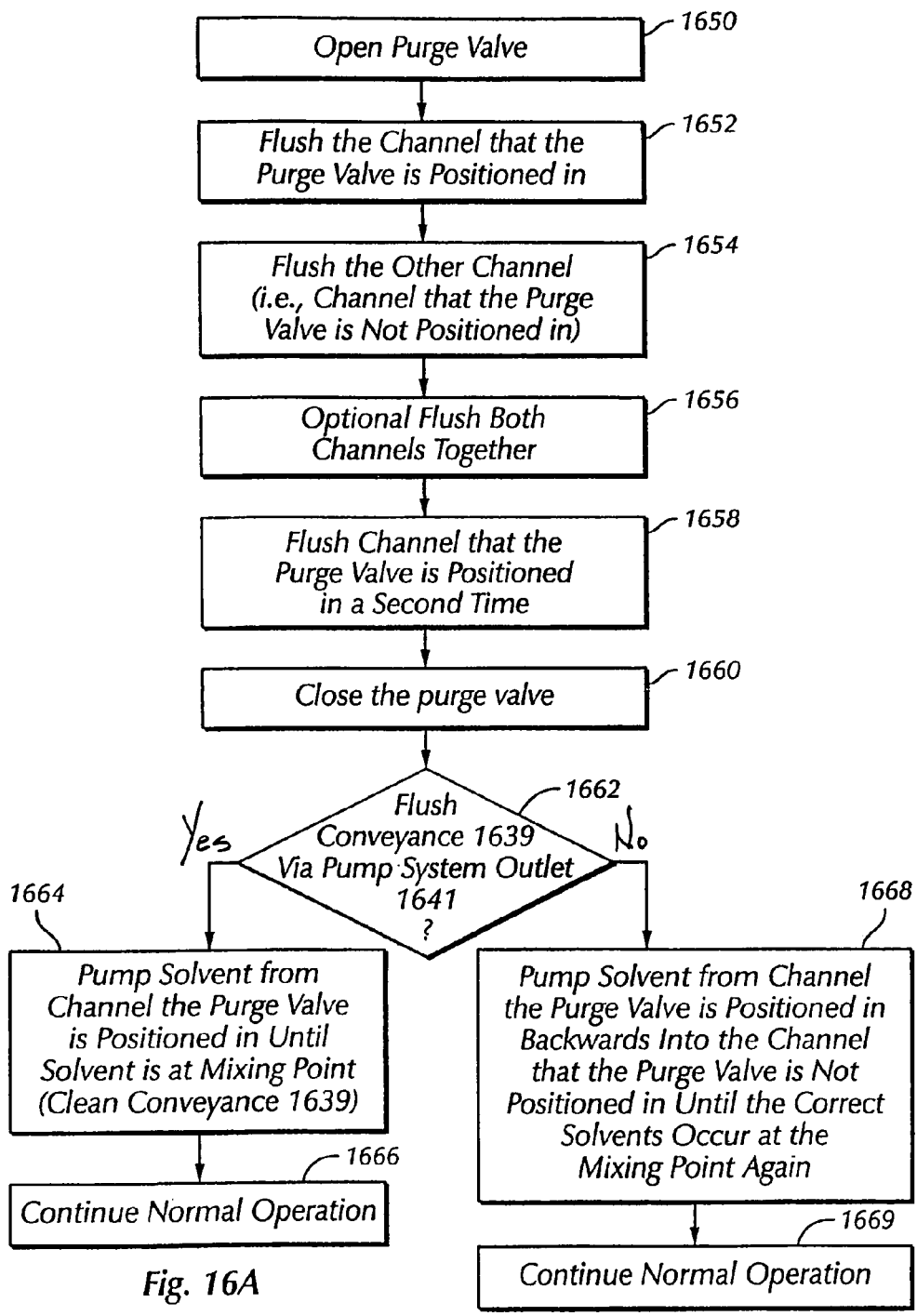
FIG. 16A is a flowchart of a method of flushing a multi-channel pumping system.

FIG. 16A is a flowchart of a method of flushing a pumping system completely. FIG. 16A will be discussed in conjunction with FIG. 16. The method commences with step 1650.

At step 1650, a purge valve, such as purge valve 1634, is opened.

At step 1652, the channel in which purge valve 1634 is positioned is flushed. For example, in system 1600, channel 1610 is flushed. Flushing channel 1610 includes conveying liquid on channel output 1630, through T-junction 1637, through waste output 1633, through purge valve 1634, and through waste exhaust 1636.

At step 1654, a channel that purge valve 1634 is not positioned in is flushed. For example, channel 1620 is flushed. Flushing channel 1620 includes conveying liquid on channel output 1642, through T-junction 1640, through conveyance 1639, through T-junction 1637, through waste output 1633, through purge valve 1634, and through waste exhaust 1636.

Step 1656 is an optional step where both channels 1610 and 1620 may be flushed together.

At step 1658, the channel in which purge valve 1634 is positioned is flushed one more time. For example, channel 1610 is flushed again.

At step 1660, purge valve 1634 is closed.

At step 1662, a decision is made regarding how to flush conveyance 1639, i.e., the conveyance between the two T-junctions (i.e., 1637 and 1640), with liquid from the channel the purge valve 1634 is positioned. For example, this would include flushing conveyance 1639 with liquid flowing through channel output 1630. If the decision is made to flush conveyance 1639 via system output 1641, then the method progresses to step 1664. If the decision is made to not flush conveyance 1639 via pump system outlet 1641, then the method progresses to step 1668.

In step 1664, solvent is pumped from the channel in which purge valve 1639 is positioned until liquid is at the mixing point. This has the effect of cleaning the conveyance between the two T-junctions, of liquid from the second channel. Using FIG. 16 as an example, this would include pumping liquid from channel 1610, through channel output 1630, across T-junction 1637, across conveyance 1639 to a mixing point defined by the location where channel output 1630, channel output 1642, and pumping system output 1641 meet in T-junction 1640. From step 1664, the method progresses to step 1666.

In step 1666, normal operation is continued.

At step 1668, solvent is pumped from the channel in which the purge valve is positioned, backwards to the channel in which the purge valve is not positioned, until the correct solvents occur at a defined mixing point. Using FIG. 16, this would mean pumping liquid from channel 1610 along channel output 1630, past T-junction 1637, along conveyance 1639, past T-junction 1640 backwards into channel output 1642. From step 1668, the method progresses to step 1669.

In step 1669, normal operation is continued.

Figure 16B:
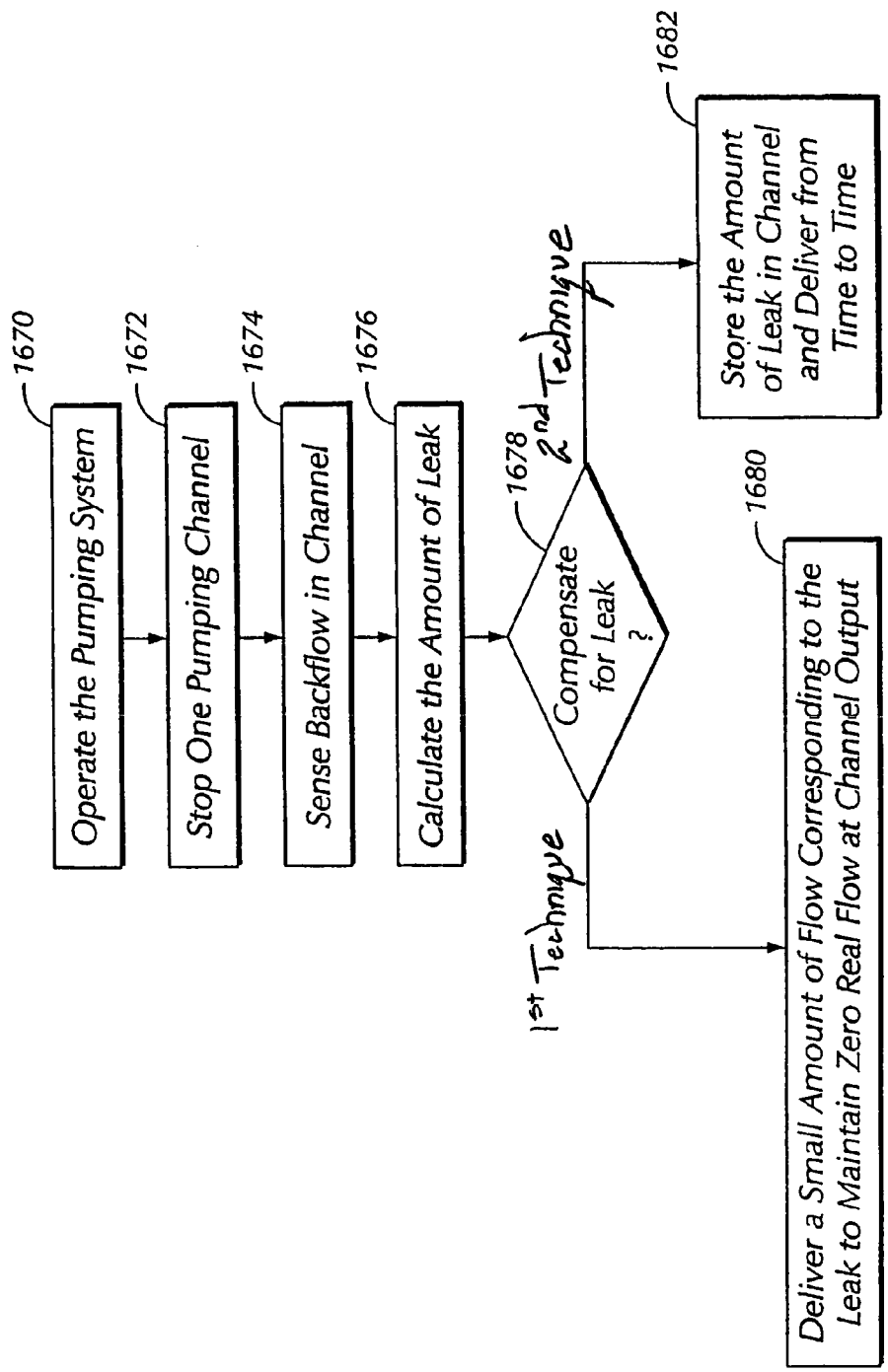
FIG. 16B is a flowchart of a method of eliminating cross-channel flow in a multi-channel pumping system.

FIG. 16B displays a flowchart depicting a method of compensating for a leak in a multi-channel pumping system. FIG. 16B will be discussed in conjunction with FIG. 16. The method commences with step 1670.

At step 1670, a pumping system, such as pumping system 1600, is operating.

At step 1672, the pumping in one channel is stopped.

At step 1674, the backflow into the stopped channel is detected.

At step 1676, the backflow into the stopped channel is used to calculate the amount of the leak.

At step 1678, a technique for compensating for the leak is selected from a first technique and a second technique. If the first technique is selected, the method progresses to step 1680. If the second technique is selected, the method progresses to step 1682.

In step 1680, the first technique for compensating for the leak is employed. In accordance with this first technique, a small amount of flow is delivered to maintain zero flow at the channel output.

In step 1682, the second technique for compensating for the leak is employed. In accordance with this second technique, the leak is stored in the stopped channel output. The channel output itself is cleaned from time to time by delivering the stored leak.

The method depicted by the flowchart of FIG. 16B will now be discussed in conjunction with the pumping system 1600 of FIG. 16.

At step 1670, pumping system 1600 is operating.

At step 1672 one channel, such as channel 1610, is stopped.

At step 1674, the backflow into channel 1610 is sensed. In one embodiment, the backflow into channel 1610 is sensed in flow sensor 1638.

At step 1676, the amount of leak in channel 1610 is calculated. The leak may be calculated using a number of the foregoing techniques presented in the instant application. For example, in one embodiment, the leak equals the measured flow minus the metered flow determined by pumping units 1612 and 1614.

At step 1678, a technique for compensating for the leak is selected from a first technique and a second technique. If the first technique is selected, the method progresses to step 1680. If the second technique is selected, the method progresses to step 1682.

At step 1680, the first technique is employed. A small amount of flow is delivered to maintain a zero flow at the mixing point. For example, an amount of flow equal to the leak may be generated dynamically to maintain a zero flow at the mixing point defined by T-junction 1640. Delivering the flow equal to the leak will include operating channel 1610 to generate an amount equivalent to the leak and a zero flow at T-junction 1640.

At step 1682, the second technique is employed. An amount of liquid equivalent to the amount of leak is stored in channel output 1630. The channel is cleaned from time to time, preferably when the chromatography is not influenced.

Thus, the present invention has been described herein with reference to a particular embodiment for a particular application. Those having ordinary skill in the art and access to the present teachings will recognize additional modifications, applications, and embodiments within the scope thereof.

It is, therefore, intended by the appended claims to cover any and all such applications, modifications, and embodiments within the scope of the present invention.

What is claimed is:

1. A pumping system comprising:
   a first pumping unit and a second pumping unit in a cooperative arrangement to provide a continuous flow of fluid to a channel output, wherein each pumping unit has a piston for reciprocation in a pump working chamber to compress liquid in the pump working chamber to a pressure at which compressibility of the liquid becomes measurable, the first and second pumping units being coupled either:
   in a serial manner, with an outlet of the first pumping unit being coupled to an inlet of the second pumping unit, and an outlet of the second pumping unit providing the channel output of the pumping system, or
   in a parallel manner, with an outlet of the first pumping unit being coupled to an outlet of the second pumping unit, thus providing the channel output of the pumping system,
   wherein the piston of the first pumping unit is synchronized with respect to the piston of the second pumping unit to provide a flow of fluid to the channel output of the pumping system, and
   a flow sensor positioned in series with an output of the first pumping unit, and before the channel output, wherein the flow sensor detects a flow rate of fluid from the first pumping unit, and provides a signal indicative of the flow rate.

2. The pumping system as set forth in claim 1,
   wherein, when the first pumping unit and the second pumping unit are positioned in parallel with one another, fluid from the output of the first pumping unit and fluid from an output of the second pumping unit merge at a junction, and
   the flow sensor is positioned before the junction.

3. The pumping system of claim 1,
   wherein the first reciprocating pump and the second reciprocating pump operate with a phase relationship with respect to one another to provide the flow rate.

4. The pumping system of claim 1, further comprising a processor that receives the signal and renders a determination concerning whether the pumping system has a leak.

5. The pumping system as set forth in claim 1,
   wherein when the first pumping unit and the second pumping unit are positioned in a serial manner, and the flow sensor is positioned between the first pumping unit and the second pumping unit.

6. The pumping system as set forth in claim 1, wherein the flow sensor measures flow independent of flow direction.

7. An analysis system comprising a pumping system according to claim 1, comprising at least one selected from the group consisting of:
   the analysis system is a chromatography system,
   the analysis system is a High Pressure Liquid Chromatography system;
   a column adapted for separating compounds of the fluid;
   a sensor adapted for sensing separated compounds of the fluid;
   a sampler adapted for introducing samples to be separated into the fluid; and a fractionator adapted for outputting separated compounds of the fluid.

8. The pumping system as set forth in claim 1, further comprising:
   a first drive system coupled to the first pumping unit and causing the first pumping unit to pump the fluid; and
   a second drive system coupled to the second pumping unit and causing the second pumping unit to pump the fluid.

9. The pumping system as set forth in claim 8, further comprising a computer coupled the first drive system, for controlling the first drive system.

10. The pumping system as set forth in claim 1, further comprising:
   a first drive system coupled to the first pumping unit and causing the first pumping unit to pump a first fluid at a first flow rate; and
   a second drive system coupled to the second pumping unit and causing the second pumping unit to pump a second fluid at a second flow rate.

11. The pumping system according to claim 10, wherein the first flow rate is substantially similar to the second flow rate.

* * * * *